US008473222B2

(12) United States Patent
Romey et al.

(10) Patent No.: US 8,473,222 B2
(45) Date of Patent: *Jun. 25, 2013

(54) MEASUREMENT DEVICES AND METHODS FOR MEASURING ANALYTE CONCENTRATION INCORPORATING TEMPERATURE AND PH CORRECTION

(75) Inventors: Matthew A. Romey, Newport Beach, CA (US); Soya Gamsey, Huntington Beach, CA (US); Thomas A. Peyser, Menlo Park, CA (US)

(73) Assignee: Glumetrics, Inc., Irvine, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 13/046,571

(22) Filed: Mar. 11, 2011

(65) Prior Publication Data

US 2011/0224516 A1    Sep. 15, 2011

Related U.S. Application Data

(60) Provisional application No. 61/313,066, filed on Mar. 11, 2010.

(51) Int. Cl.
G06F 17/11 (2006.01)
G06F 17/50 (2006.01)
A61B 5/05 (2006.01)

(52) U.S. Cl.
USPC ............... 702/23; 702/19; 600/345; 600/347

(58) Field of Classification Search
None
See application file for complete search history.

(56) References Cited

U.S. PATENT DOCUMENTS

| | | | |
|---|---|---|---|
| 4,810,655 A | 3/1989 | Khalil et al. |
| 5,114,676 A | 5/1992 | Leiner et al. |
| 5,137,033 A | 8/1992 | Norton |
| 5,137,833 A | 8/1992 | Russell |
| 5,156,962 A | 10/1992 | Suzuki et al. |
| 5,503,770 A | 4/1996 | James et al. |
| 5,512,246 A | 4/1996 | Russell et al. |
| 5,618,587 A | 4/1997 | Markle et al. |
| 5,763,238 A | 6/1998 | James et al. |
| 5,810,985 A | 9/1998 | Boa et al. |
| 6,002,954 A | 12/1999 | Van Antwerp et al. |
| 6,011,984 A | 1/2000 | Van Antwerp et al. |
| 6,197,534 B1 | 3/2001 | Lakowicz et al. |
| 6,227,627 B1 | 5/2001 | Goossens |
| 6,304,766 B1 | 10/2001 | Colvin, Jr. |
| 6,319,540 B1 | 11/2001 | Van Antwerp et al. |
| 6,521,447 B2 | 2/2003 | Zou et al. |
| 6,602,702 B1 | 8/2003 | McDevitt et al. |
| 6,627,177 B2 | 9/2003 | Singaram et al. |
| 6,653,141 B2 | 11/2003 | Singaram et al. |
| 6,766,183 B2 | 7/2004 | Walsh et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,855,556 B2 | 2/2005 | Amiss et al. |
| 7,064,103 B2 | 6/2006 | Pitner et al. |
| 7,276,029 B2 | 10/2007 | Goode, Jr. et al. |
| 7,316,909 B2 | 1/2008 | Pitner et al. |
| 7,326,538 B2 | 2/2008 | Pitner et al. |
| 7,345,160 B2 | 3/2008 | Daunert et al. |
| 7,417,164 B2 | 8/2008 | Suri |
| 7,470,420 B2 | 12/2008 | Singaram et al. |
| 7,496,392 B2 | 2/2009 | Alarcon et al. |
| 7,751,863 B2 | 7/2010 | Markle et al. |
| 7,767,846 B2 | 8/2010 | Suri |
| 7,824,918 B2 | 11/2010 | Suri |
| 7,829,341 B2 | 11/2010 | Gamsey et al. |
| 8,088,097 B2 | 1/2012 | Markle et al. |
| 2003/0232383 A1 | 12/2003 | Daunert et al. |
| 2004/0028612 A1 | 2/2004 | Singaram et al. |
| 2005/0059097 A1 | 3/2005 | Daunert et al. |
| 2005/0090014 A1 | 4/2005 | Rao et al. |
| 2005/0130249 A1 | 6/2005 | Parris et al. |
| 2005/0233465 A1 | 10/2005 | Miller |
| 2005/0282225 A1 | 12/2005 | Daunert et al. |
| 2006/0083688 A1 | 4/2006 | Singaram et al. |
| 2006/0189863 A1 | 8/2006 | Peyser et al. |
| 2007/0136825 A1 | 6/2007 | Frommer et al. |
| 2007/0207498 A1 | 9/2007 | Palmieri et al. |
| 2008/0187655 A1 | 8/2008 | Markle et al. |

(Continued)

FOREIGN PATENT DOCUMENTS

WO    WO 03/060464 A2    7/2003
WO    WO/2004/054438 A1    7/2004

(Continued)

OTHER PUBLICATIONS

Liu et al. Anal. Chem. 1997, 69, 2343-2348.*
Ayala et al. Database Caplus, DN 133:189758. (Protein Science (2000), 9(8), 1589-1593).*
Fidaleo et al. Database Caplus, DN 140:249134 (Chemical and Biochemical Engineering Quarterly (2003), 17(4), 311-318).*
PCT International Search Report re PCT/US2010/037502 dated Aug. 6, 2010.
Stokes, et al.: "An optical oxygen sensor and reaction vessel for high-pressure applications", Limnol. Oceanogr., 44(1), 1999, 189-195.
PCT International Preliminary Report on Patentability re PCT/US2010/037502, dated Dec. 6, 2011.

(Continued)

Primary Examiner — Michael Borin
(74) Attorney, Agent, or Firm — Knobbe Martens Olson & Bear, LLP

(57) ABSTRACT

Disclosed herein are methods of estimating an analyte concentration which include generating a signal indicative of the analyte concentration, generating a signal indicative of a temperature, generating a signal indicative of a pH, and transforming the signal indicative of the analyte concentration utilizing an equation of the form of a modified Michaelis-Menten equation depending on Michaelis-Menten parameters, wherein values of the Michaelis-Menten parameters are set based upon data which includes temperature and pH calibration parameters, the signal indicative of a temperature, and the signal indicative of a pH. Also disclosed herein are measurement devices which employ the aforementioned methods.

14 Claims, 23 Drawing Sheets

U.S. PATENT DOCUMENTS

| | | |
|---|---|---|
| 2008/0188722 A1 | 8/2008 | Markle et al. |
| 2008/0188725 A1 | 8/2008 | Markle et al. |
| 2008/0261255 A1 | 10/2008 | Tolosa et al. |
| 2008/0296155 A1 | 12/2008 | Shults et al. |
| 2008/0305009 A1 | 12/2008 | Gamsey et al. |
| 2008/0311675 A1 | 12/2008 | Thomas et al. |
| 2009/0005266 A1 | 1/2009 | Ostermeier et al. |
| 2009/0018418 A1 | 1/2009 | Markle et al. |
| 2009/0018426 A1 | 1/2009 | Markle et al. |
| 2009/0048430 A1 | 2/2009 | Hellinga et al. |
| 2009/0081803 A1 | 3/2009 | Gamsey et al. |
| 2009/0082566 A1 | 3/2009 | Mitra |
| 2009/0088329 A1 | 4/2009 | Brennan et al. |
| 2009/0098052 A1 | 4/2009 | Schilling et al. |
| 2009/0104714 A1 | 4/2009 | Thomas et al. |
| 2009/0264719 A1 | 10/2009 | Markle et al. |
| 2010/0312483 A1 | 12/2010 | Peyser et al. |

FOREIGN PATENT DOCUMENTS

| | | |
|---|---|---|
| WO | WO 2008/072338 A1 | 6/2008 |
| WO | WO 2009/021026 A1 | 2/2009 |
| WO | WO 2009/021039 A1 | 2/2009 |
| WO | WO 2009/021052 A1 | 2/2009 |
| WO | WO 2009/036070 A1 | 3/2009 |
| WO | WO 2010/141888 | 9/2010 |

OTHER PUBLICATIONS

PCT International Search Report and Written Opinion in App. No. PCT/US2011/028222, dated May 6, 2011, in 30 pages.

PCT International Preliminary Report and Written Opinion in App. No. PCT/US2011/028222, dated Sep. 11, 2012, in 19 pages.

Badugu et al., "Boronic acid fluorescent sensors for monosaccharide signaling based on the 6-methoxyquinolinium heterocyclic nucleus: progress toward noninvasive and continuous glucose monitoring", Bioorganic and Medicinal Chemistry, 2005, vol. 13, pp. 113-119.

Badugu et al., "Fluorescence sensors for monosaccharides based on the 6-methylquinolinium nucleus and boronic acid moiety: potential application to ophthalmic diagnostics", Talanta, 2005, vol. 65, pp. 762-768.

* cited by examiner

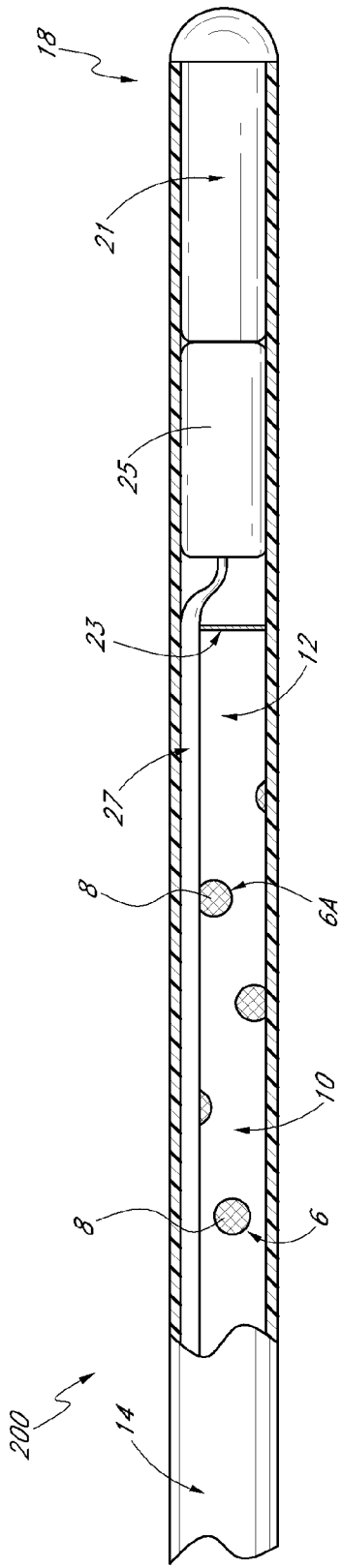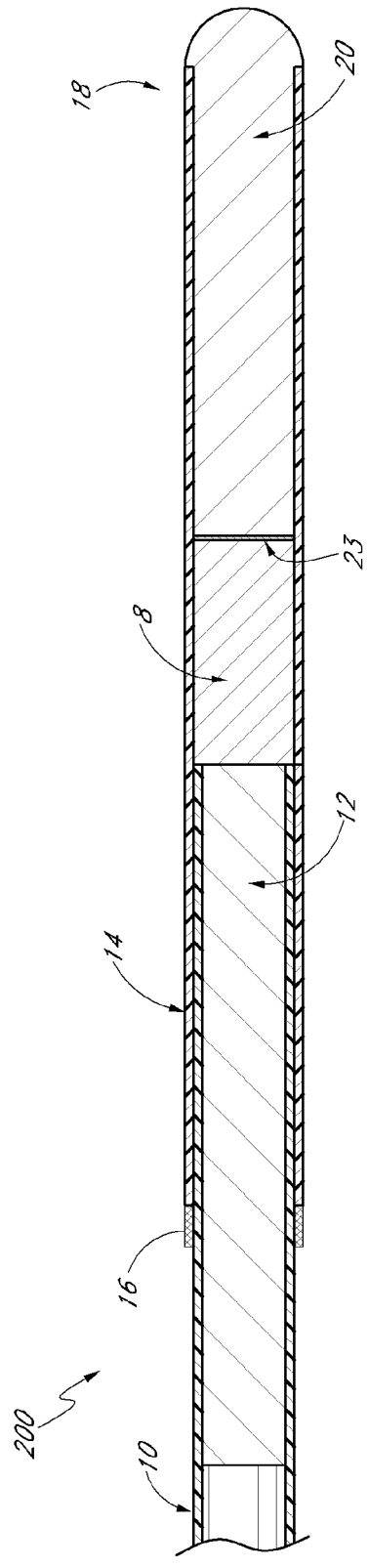

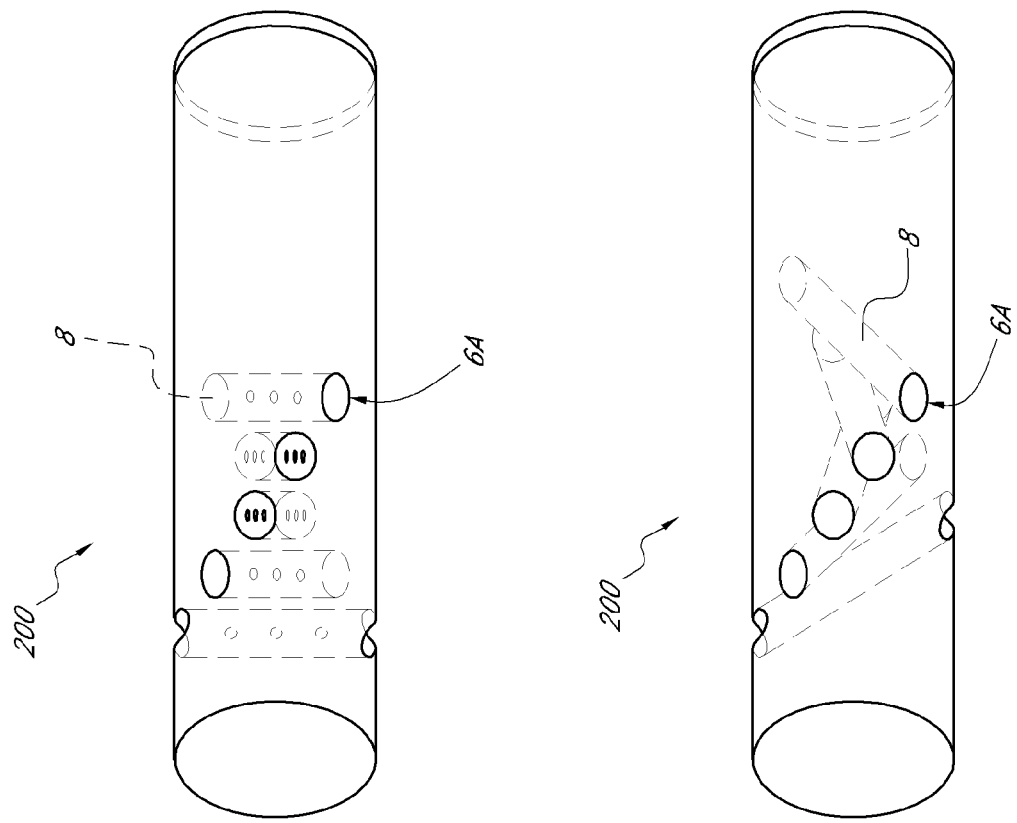

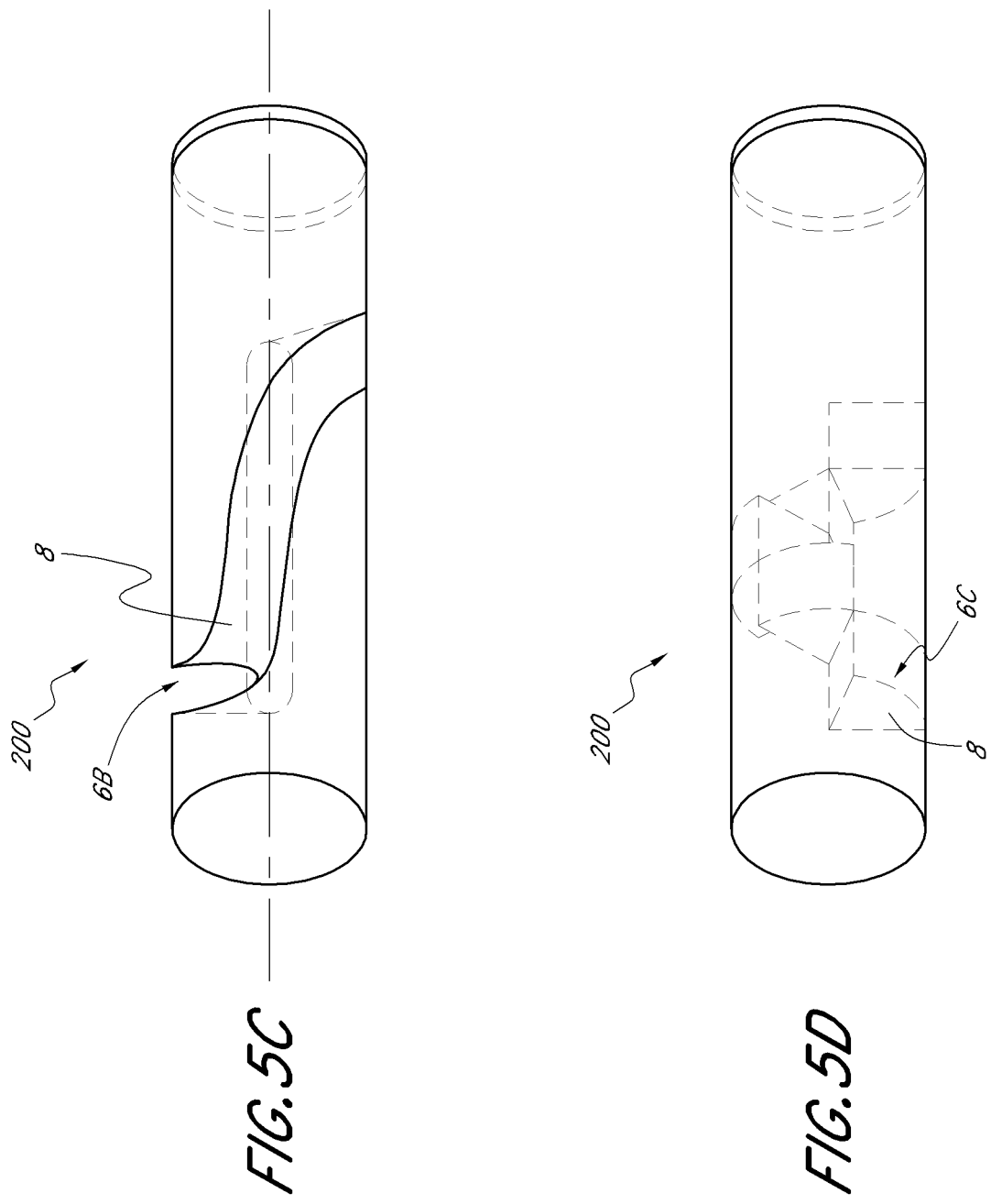

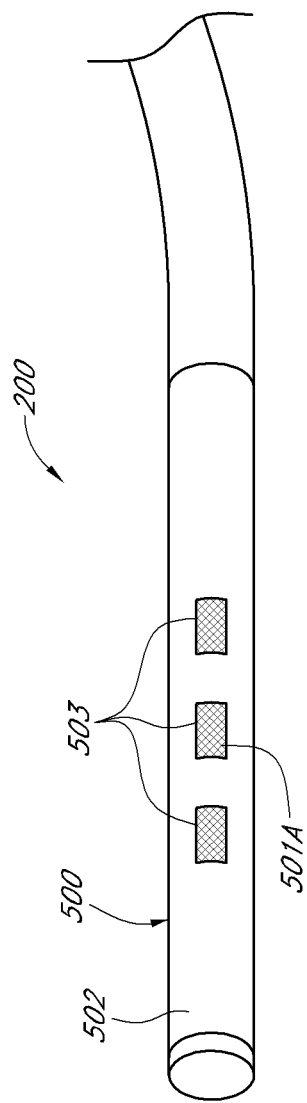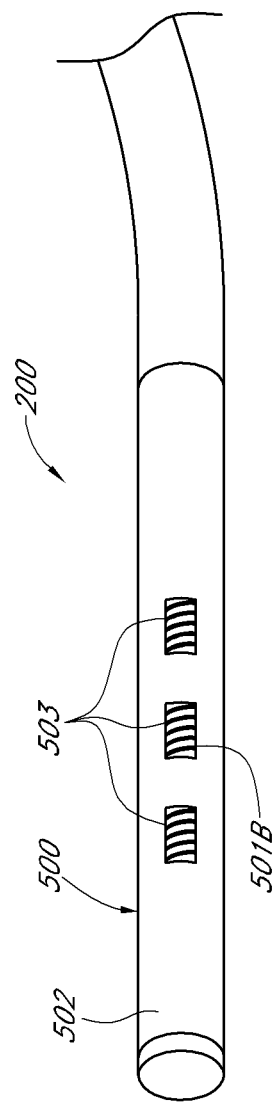

MEASUREMENT DEVICES AND METHODS FOR MEASURING ANALYTE CONCENTRATION INCORPORATING TEMPERATURE AND PH CORRECTION

CROSS-REFERENCE TO RELATED APPLICATIONS

This application claims priority to U.S. Provisional Patent Application No. 61/313,066, filed Mar. 11, 2010 the disclosure of which is hereby expressly incorporated by reference and hereby expressly made a portion of this application. This application is also related to co-pending U.S. patent application Ser. No. 12/794,466, filed Jun. 4, 2010, the disclosure of each of which are hereby expressly incorporated by reference in their entireties and are hereby expressly made a portion of this application.

BACKGROUND OF THE INVENTION

1. Field of the Invention

The present application discloses embodiments which relate to the field of analyte concentration measurement, more specifically, glucose concentration measurement, and, in some embodiments, algorithms and methods of temperature and/or pH correction, and measurement devices which perform temperature and/or pH correction.

2. Description of the Related Art

Types 1 and 2 diabetes are endocrine disorders characterized by abnormalities in the body's ability to regulate glucose metabolism. While the underlying pathology of these two illnesses differ, both are associated with significant complications including diabetic nephropathy, neuropathy, retinopathy, problems with wound healing, as well as an elevated risk of cerebrovascular and cardiovascular disease. While the mechanism of action is uncertain, it is believed that elevated glucose levels are associated with the release of various inflammatory mediators that produce vascular damage ultimately leading to these complications. Abnormally low glucose levels can also be problematic resulting in anxiety, weakness, and in extreme cases coma and death. Researchers and clinicians have increasingly become aware of the importance of maintaining tight control of glucose levels, particularly in acute care settings, so as to prevent these complications from occurring and to facilitate patient recovery.

While clinicians have used insulin for decades to regulate glucose levels in diabetics, determining precise dosages remains a problem. Insulin has the overall effect of reducing circulating glucose levels through a series of complex interactions involving a number of hormones and cell types. While dosage protocols for insulin attempt to replicate the physiologic secretion of the hormone by the pancreas, administering according to fixed times and algorithms based on serum glucose measurements can only crudely approximate the ability of a healthy individual to continuously adjust insulin production in response to glucose levels and the needs of the body. It follows that in order to determine the precise amount of insulin that must be administered to maintain a patient's circulating glucose levels at a normal level, it is necessary to have an extremely accurate measurement of how much glucose is present and available to the patient at any given time.

Unfortunately, existing methods of determining a patient's glucose level leave much to be desired. Clinicians and diabetic patients routinely test glucose levels by testing unprocessed blood. While the results can be available quickly, they can often be inaccurate. Glucose freely diffuses in and out of red blood cells which can cause the result to vary depending on the concentration of such cells in the sample. Furthermore, the diffusion of glucose out of blood cells is often magnified by the requirement that the whole blood be diluted, thus altering the osmotic potential across the membranes of the blood cells.

A more accurate determination of the patient's glucose level can be obtained by measuring plasma glucose. This requires the separation of the plasma from the other components of the blood such as red and white blood cells. There exist a number of analytical methods for measuring plasma glucose concentration. These include the measurement of the current produced by glucose oxidation, the use of the hexokinase reaction, or through the use of mass spectrometry. While the latter represents the "gold standard" for glucose measurement, these methods can be technically complicated, time-consuming, and are frequently not cost-effective for clinical use. For example, for the most accurate readings, lipids should be removed from the plasma and the results should be adjusted for the sodium content, but both are rarely done. Finally, the results can vary depending on how much protein-bound and intercellular glucose has been released into the sample prior to and during processing. While plasma glucose measurements can provide relatively accurate information, transportation and processing times can lead to a significant delay between when the sample is collected and when the results are available to the clinician. Therefore, it is not feasible to use plasma glucose measurements for near-instantaneous, or "real-time" monitoring of a patient's glucose level.

SUMMARY OF THE INVENTION

Disclosed herein are methods of estimating an analyte concentration which may include generating a signal indicative of the analyte concentration, generating a signal indicative of a temperature, and transforming the signal indicative of the analyte concentration utilizing an equation of the form of a modified Michaelis-Menten equation depending on Michaelis-Menten parameters, wherein values of the Michaelis-Menten parameters are set based on data which may include temperature calibration data and the signal indicative of a temperature.

Also disclosed herein are methods of estimating an analyte concentration which may include generating a signal indicative of the analyte concentration, generating a signal indicative of a temperature, and transforming the signal indicative of the analyte concentration utilizing an equation of the form of a modified Michaelis-Menten equation wherein at least one of the Michaelis-Menten parameters has been substituted with a calibration equation functionally depending on a set of one or more temperature calibration parameters and the signal indicative of temperature.

Also disclosed herein are methods of estimating an analyte concentration which may include generating a signal indicative of the analyte concentration, generating a signal indicative of a pH, and transforming the signal indicative of the analyte concentration utilizing an equation of the form of a modified Michaelis-Menten equation depending on Michaelis-Menten parameters, wherein values of the Michaelis-Menten parameters are set based on data which may include pH calibration data, and the signal indicative of a pH.

Also disclosed herein are methods of estimating an analyte concentration which may include generating a signal indicative of the analyte concentration, generating a signal indicative of a pH, and transforming the signal indicative of the analyte concentration utilizing an equation of the form of a modified Michaelis-Menten equation wherein at least one of the Michaelis-Menten parameters has been substituted with a calibration equation functionally depending on a set of one or more pH calibration parameters and the signal indicative of pH.

Also disclosed herein are methods of estimating an analyte concentration which may include generating a signal indicative of the analyte concentration, generating a signal indicative of a temperature, generating a signal indicative of a pH, and transforming the signal indicative of the analyte concentration utilizing an equation of the form of a modified Michaelis-Menten equation depending on Michaelis-Menten parameters, wherein values of the Michaelis-Menten parameters are set based on data which may include temperature and pH calibration parameters, the signal indicative of a temperature, and the signal indicative of a pH.

Also disclosed herein are methods of estimating an analyte concentration of a solution which may include generating a signal indicative of the analyte concentration of the solution, generating a signal indicative of a temperature of the solution, generating a signal indicative of a pH of the solution, and transforming the signal indicative of the analyte concentration utilizing an equation of the form of a modified Michaelis-Menten equation wherein at least one of the Michaelis-Menten parameters has been substituted with a calibration equation functionally depending on a set of one or more temperature and pH calibration parameters, the signal indicative of the temperature, and the signal indicative of the pH.

Also disclosed herein are measurement devices for estimating an analyte concentration of a sample. In some embodiments, the measurement devices may include an analyte sensing element, a temperature sensing element, and a receiving and processing unit. In some embodiments, the analyte sensing element may be configured to generate a first signal, the first signal indicative of the analyte concentration of the sample. In some embodiments, the temperature sensing element may be configured to generate a second signal, the second signal indicative of a temperature of the sample. In some embodiments, the receiving and processing unit may be configured to transform the first signal utilizing an equation of the form of a modified Michaelis-Menten equation depending on Michaelis-Menten parameters, wherein values of the Michaelis-Menten parameters are set based upon data which may include temperature calibration data, and the second signal.

The measurement devices for estimating an analyte concentration of a sample may, in some embodiments, include an analyte sensing element, a pH sensing element, and a receiving and processing unit. In some embodiments, the analyte sensing element may be configured to generate a first signal, the first signal indicative of the analyte concentration of the sample. In some embodiments, the pH sensing element may be configured to generate a second signal, the second signal indicative of a pH of the sample. In some embodiments, the receiving and processing unit may be configured to transform the first signal utilizing an equation of the form of a modified Michaelis-Menten equation depending upon Michaelis-Menten parameters, wherein values of the Michaelis-Menten parameters are set based on data which may include pH calibration data, and the second signal.

The measurement devices for estimating an analyte concentration of a sample, may, in some embodiments, include an analyte sensing element, a temperature sensing element, and a pH sensing element. In some embodiments, the analyte sensing element may be configured to generate a first signal, the first signal indicative of the analyte concentration of the sample. In some embodiments, the temperature sensing element may be configured to generate a second signal, the second signal indicative of a temperature of the sample. In some embodiments, the pH sensing element may be configured to generate a third signal, the third signal indicative of a pH of the sample. In some embodiments, the receiving and processing unit may be configured to transform the first signal utilizing an equation of the form of a modified Michaelis-Menten equation depending on Michaelis-Menten parameters, wherein values of the Michaelis-Menten parameters are set based upon data which may include temperature and pH calibration data, the second signal, and the third signal.

The measurement devices for estimating an analyte concentration of a sample, may, in some embodiments, include an analyte and pH sensing element, and a receiving and processing unit. In some embodiments, the analyte and pH sensing element may be configured to generate a first signal, the first signal indicative of the analyte concentration of the sample and a pH of the sample. In some embodiments, the analyte and pH sensing element may be configured to generate a second signal, the second signal indicative of the analyte concentration of the sample and the pH of the sample. In some embodiments, the receiving and processing unit may be configured to transform a third signal utilizing an equation of the form of a modified Michaelis-Menten equation depending on Michaelis-Menten parameters, wherein values of the Michaelis-Menten parameters are set based upon data which may include pH calibration data and a fourth signal. In some embodiments, the third signal may be indicative of the analyte concentration and may be generated based upon data which may include the first signal and the second signal. In some embodiments, the fourth signal may be indicative of the pH and may be generated based upon data which may include the first signal and the second signal.

The measurement devices for estimating an analyte concentration of a sample may, in some embodiments, include an analyte and pH sensing element, a temperature sensing element, and a receiving and processing unit. In some embodiments, the analyte and pH sensing element may be configured to generate a first signal, the first signal indicative of the analyte concentration of the sample and a pH of the sample, and a second signal, the second signal indicative of the analyte concentration of the sample and the pH of the sample. In some embodiments, the temperature sensing element may be configured to generate a third signal, the third signal indicative of a temperature of the sample. In some embodiments, the receiving and processing unit may be configured to transform a fourth signal utilizing an equation of the form of a modified Michaelis-Menten equation depending on Michaelis-Menten parameters, wherein values of the Michaelis-Menten parameters are set based upon data which may include temperature and pH calibration data, the third signal, and a fifth signal. In some embodiments, the fourth signal may be indicative of the analyte concentration and may be generated based upon data which may include the first signal and the second signal. In some embodiments, the fifth signal may be indicative of the pH and may be generated based upon data which may include the first signal and the second signal.

Also disclosed herein are methods of estimating an analyte concentration from a signal indicative of the analyte concentration. In some embodiments, the methods may include transforming the signal using an equation of the form of a modified Michaelis-Menten equation wherein the values of one or more Michaelis-Menten parameters have been adjusted for temperature. In some embodiments, the values of one or more Michaelis-Menten parameters may also have been adjusted for pH.

BRIEF DESCRIPTION OF THE DRAWINGS

FIG. 3 is a cut-away view of a sensor probe wherein a portion of the porous membrane sheath is cut away to expose the optical fiber and hydrogel beneath the membrane.

FIG. 4 is a cross-sectional view along a longitudinal axis of a sensor probe with a hydrogel disposed in the sensor probe distal to the optical fiber.

FIG. 5A shows a sensor probe having a series of holes that form a helical configuration.

FIG. 5B shows a sensor probe having a series of holes drilled or formed at an angle.

FIG. 5C shows a sensor probe having at least one spiral groove.

FIG. 5D shows a sensor probe having a series of triangular wedge cut-outs.

FIG. 7A shows a sensor probe with a protective housing surrounding an indicator system, the protective housing including a tubular mesh surrounded by a polymeric material with an open window leading to the indicator system.

FIG. 7B shows a sensor probe with a protective housing surrounding an indicator system, the protective housing including a coil surrounded by a polymeric material with an open window leading to the indicator system.

DETAILED DESCRIPTION OF THE PREFERRED EMBODIMENT

Figure 1A:
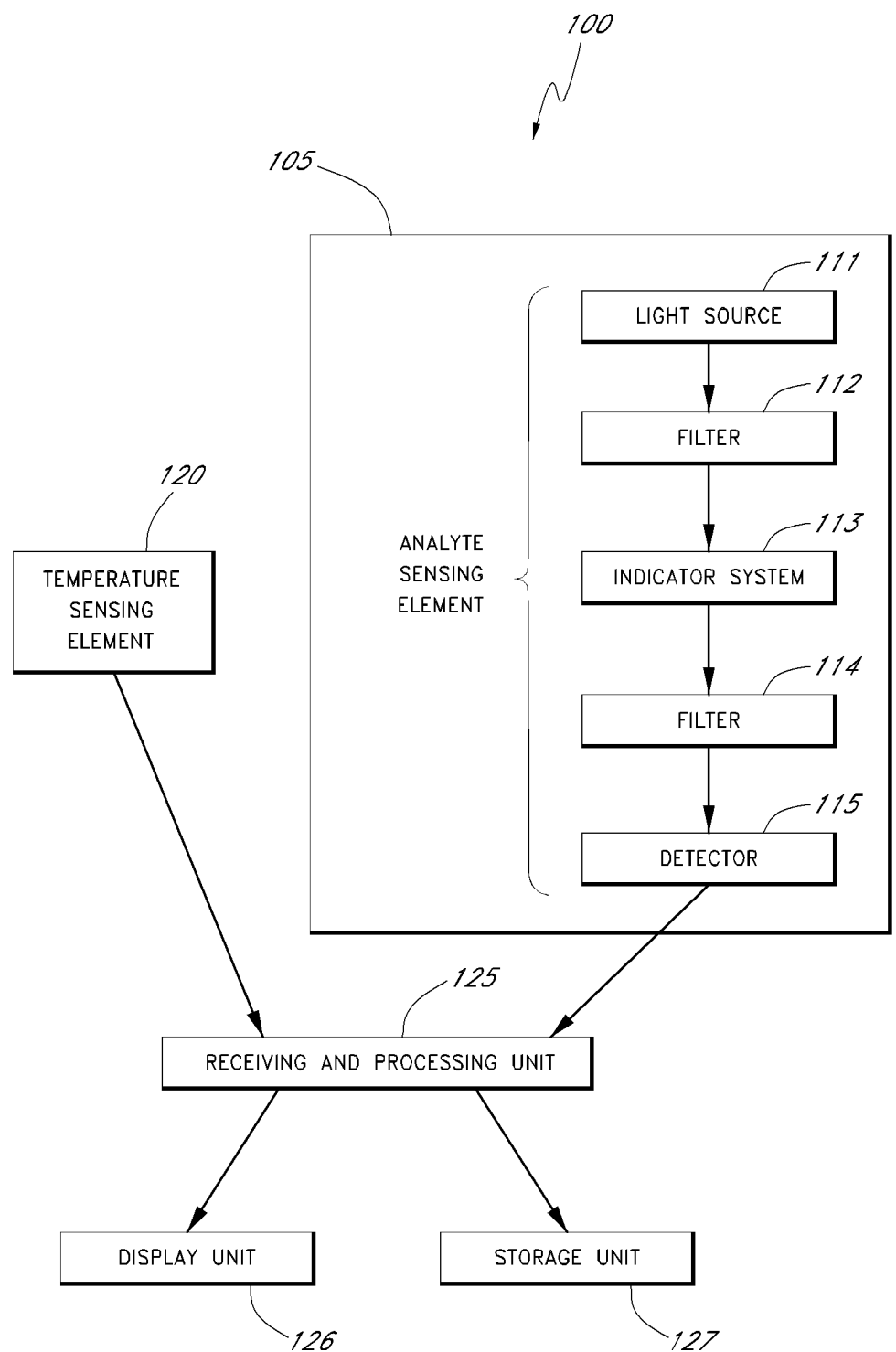
FIG. 1A is a flow chart schematically illustrating the sensing mechanism of one embodiment of the present invention which includes a temperature sensing element and an analyte sensing element.

Whole blood glucose activity is a physiologically significant quantity that may be used to determine proper insulin dosage. Glucose activity represents an estimate of the concentration of bioavailable (or free) glucose in water, blood, or any solution. Hence, a patient's whole blood glucose activity level is a physiologically more appropriate quantity by which to estimate insulin dosage, than estimated total blood glucose concentration as determined by the various methods mentioned above. Typically, glucose activity is measured through the establishment of a reversible, equilibrium-based, affinity-driven binding interaction between glucose and some moiety capable of binding free glucose. Glucose activity is not substantially affected by the presence of red blood cells, protein or lipid concentration, nor oxygenation levels. Accordingly, the time consuming step of extracting plasma from whole blood is not required, and glucose activity measurements can be made available in near "real-time." Furthermore, since glucose activity can be measured on whole blood without dilution, it provides an estimate of bioavailable glucose not polluted by the effects of altering away from biological norms, the osmotic potentials across blood cell membranes.

Fluorescent techniques may be used to efficiently and accurately measure the concentration of glucose (and other polyhydroxyl compounds). Oftentimes, these techniques may also be used to measure the concentration of bioavailable glucose in whole blood, i.e. the glucose activity of whole blood. For instance, several attempts have been made to detect glucose by fluorescence using dyes associated with boronic acid groups. Boronate moieties bind glucose reversibly. When boronic acid functionalized fluorescent dyes bind glucose, the properties of the dye are affected, such that a signal related to the concentration of glucose may be generated and detected. For example, Russell (U.S. Pat. Nos. 5,137, 833 and 5,512,246) used a boronic acid functionalized dye that bound glucose and generated a signal related to the glucose concentration. James et al. (U.S. Pat. No. 5,503,770) employed a similar principle, but combined a fluorescent dye, an amine quenching functionality, and boronic acid in a single complex. The fluorescence emission from the complex varied with the amount of glucose binding. Van Antwerp et al. (U.S. Pat. Nos. 6,002,954 and 6,011,984) combined features of the previously cited references and also disclosed a device purported to be implantable. A. E. Colvin, Jr. (U.S. Pat. No. 6,304,766) also disclosed optical-based sensing devices for in situ sensing in humans that utilize boronate-functionalized dyes. Suri (U.S. Pat. No. 7,417,164) recently disclosed several fluorescent dyes capable of being used to estimate glucose concentration or activity.

Measurement Devices

Various embodiments of the measurement devices disclosed herein comprise an analyte sensing element configured to generate a signal indicative of the analyte concentration of a sample. The analyte sensing element may include at least one light source, an indicator system, and at least one detector. In some embodiments, the indicator system (described more fully below) may include at least one type of fluorophore and at least one type of binding moiety. In some embodiments, the fluorophore emits a fluorescence having an intensity in response to light from the at least one light source. In some embodiments, the binding moiety is capable of binding the analyte and is operably coupled to the fluorophore, such that when the sample contacts the binding moiety the intensity is indicative of the concentration of the analyte. In one embodiment, the binding moiety acts as a quencher in the presence of the analyte such that when the binding moiety binds the analyte it interacts with the fluorophore in such a manner as to quench or reduce the fluorescent emission intensity. In preferred embodiments, the binding moiety associates with the fluorophore in the absence of the analyte thereby quenching the fluorescent emission intensity. Analyte binding by the binding moiety causes disassociation from the fluorophore, such that the fluorescent emission intensity increases with increasing concentration of analyte. In some embodiments, the analyte sensing element includes at least one detector which may be configured to detect the intensity and generate a signal indicative of the analyte concentration in response to the intensity.

Examples of glucose-sensing chemical indicator systems and glucose sensor configurations for intravascular glucose monitoring include the optical sensors disclosed in U.S. Pat. Nos. 5,137,033, 5,512,246, 5,503,770, 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617, 12/424,902 and 61/184,747; each of which is incorporated herein in its entirety by reference thereto.

In some embodiments, the concentration being estimated corresponds to the glucose activity of a sample. In some embodiments, the sample is whole blood. However, the embodiments disclosed herein may also measure the concentrations and/or activities of other analytes. For instance, disclosed measurement devices may, in some embodiments, be configured to measure the concentrations of other polyhydroxyl-containing organic compounds including, but not limited to, carbohydrates, 1,2-diols, 1,3-diols and the like. In some embodiments, the analytes to be measured may include non-carbohydrates. Generally, the measurement devices disclosed herein may be configured to estimate the concentration of any analyte which may be bound by a binding moiety, wherein the binding moiety is operably coupled to a fluorophore which emits a fluorescence indicative of the concentration of the analyte after being excited by light of the appropriate wavelength and intensity. The discussion of the measurement devices that follows will usually refer to the physical quantity to be measured as an "analyte concentration" or simply a "concentration." However, it is to be understood that "concentration" as used below refers to both "analyte concentration" as that phrase would be ordinarily used and also to "activity" (in some cases "glucose activity") as that phrase is described above.

Various measurement devices disclosed herein are configured to provide improved estimates of the analyte concentration of a particular solution by taking the temperature and/or the pH of the particular solution into account. Accordingly, some embodiments of the measurement devices disclosed herein may include a temperature sensing element configured to generate a signal indicative of a temperature of the sample. Likewise, some embodiments of the measurement devices disclosed herein may include a pH sensing element configured to a signal indicative of a pH of the sample. Moreover, some embodiments disclosed herein may include both a temperature sensing element and a pH sensing element.

In some embodiments disclosed herein, a single element may be configured to sense both pH and analyte concentration. In certain embodiments, this analyte and pH sensing element may be configured to generate two signals, both of which are indicative of analyte concentration and pH. Thus, in certain embodiments, an analyte and pH sensing element may generate a first signal indicative of an analyte concentration of a sample and a pH of the sample, and also generate a second signal indicative of the analyte concentration of the sample and the pH of the sample. Moreover, some embodiments including an analyte and pH sensing element may further include a temperature sensing element configured to generate a third signal which is indicative of a temperature of the sample.

In certain embodiments, the measurement devices disclosed herein may further include a receiving and processing unit. In some embodiments, the receiving and processing unity may be configured to transform a signal indicative of analyte concentration, which has been generated by an analyte sensing element. In some embodiments, the receiving and processing unit may transform the signal utilizing an equation of the form of a modified Michaelis-Menten equation depending on Michaelis-Menten parameters, as described in detail below. In some embodiments, the values of the Michaelis-Menten parameters may be set based upon data which may include temperature calibration data and a signal indicative of temperature which has been generated by a temperature sensing element. In some embodiments, the values of the Michaelis-Menten parameters may be set based upon data which may include pH calibration data and a signal indicative of pH which has been generated by a pH sensing element. In some embodiments, the values of the Michaelis-Menten parameters may be set based upon data which may include temperature and pH calibration data, a signal indicative of temperature which has been generated by a temperature sensing element, and a signal indicative of pH which has been generated by a pH sensing element. In some embodiments, the signal indicative of analyte concentration—which is transformed by the receiving and processing unit—has been generated based upon data comprising two signals, each of which was generated by an analyte and pH sensing element, and each of which is indicative of analyte concentration and pH. These two signals may also be utilized to generate a signal indicative of pH which may be used with calibration data to set values of the Michaelis-Menten parameters.

Figure 1B:
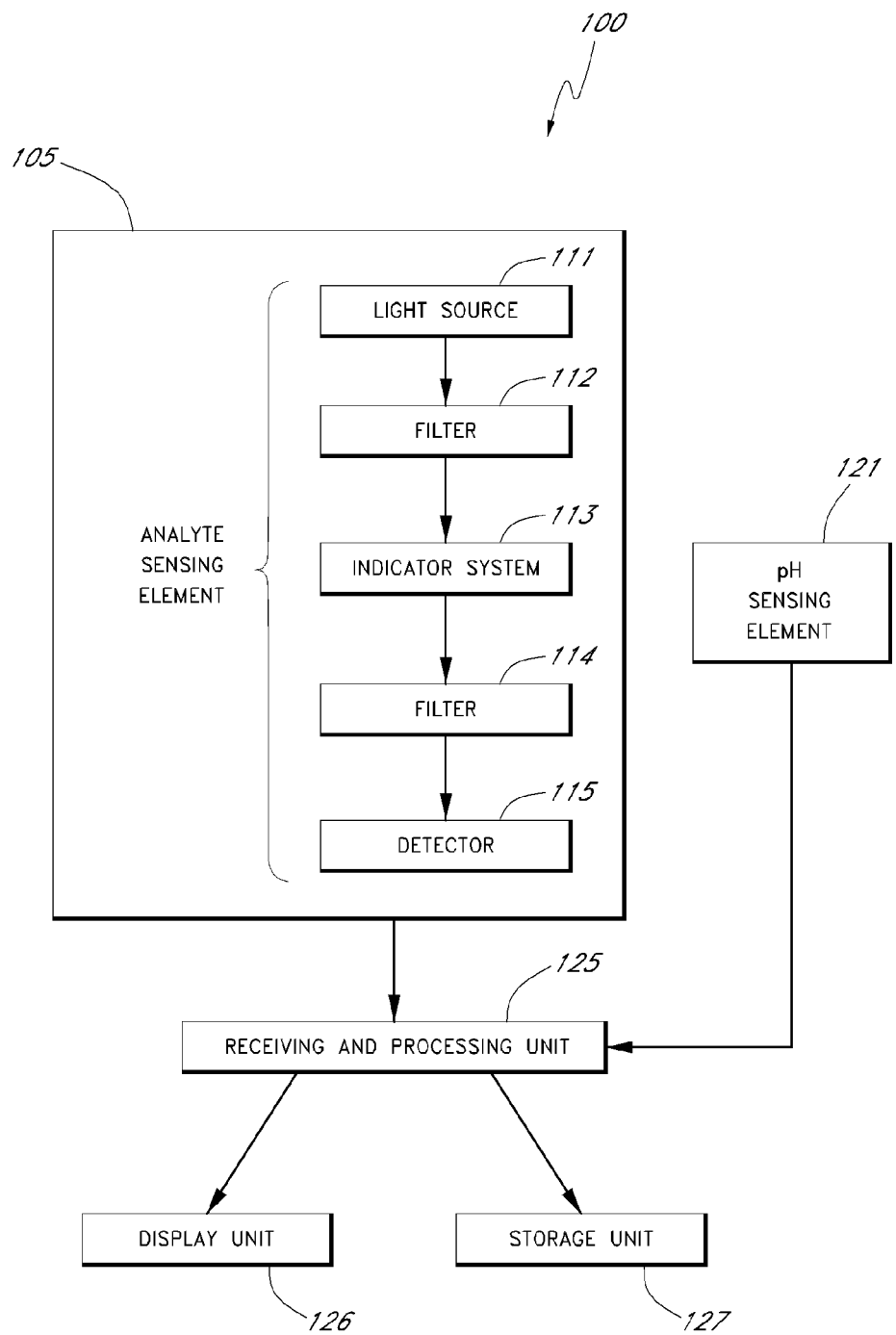
FIG. 1B is a flow chart schematically illustrating the sensing mechanism of one embodiment of the present invention which includes an analyte sensing element and a pH sensing element.
Figure 1C:
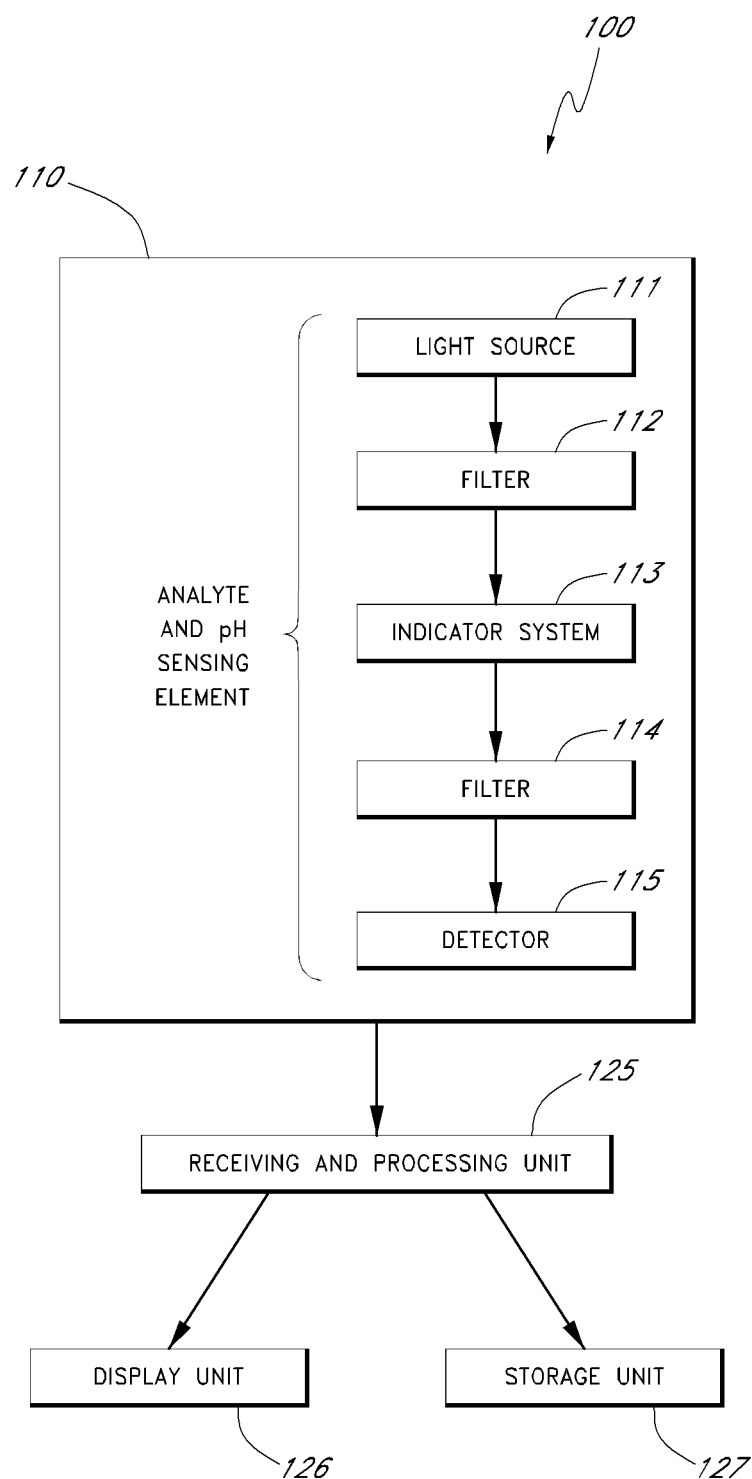
FIG. 1C is a flow chart schematically illustrating the sensing mechanism of one embodiment of the present invention which includes a pH and analyte sensing element.
Figure 1D:
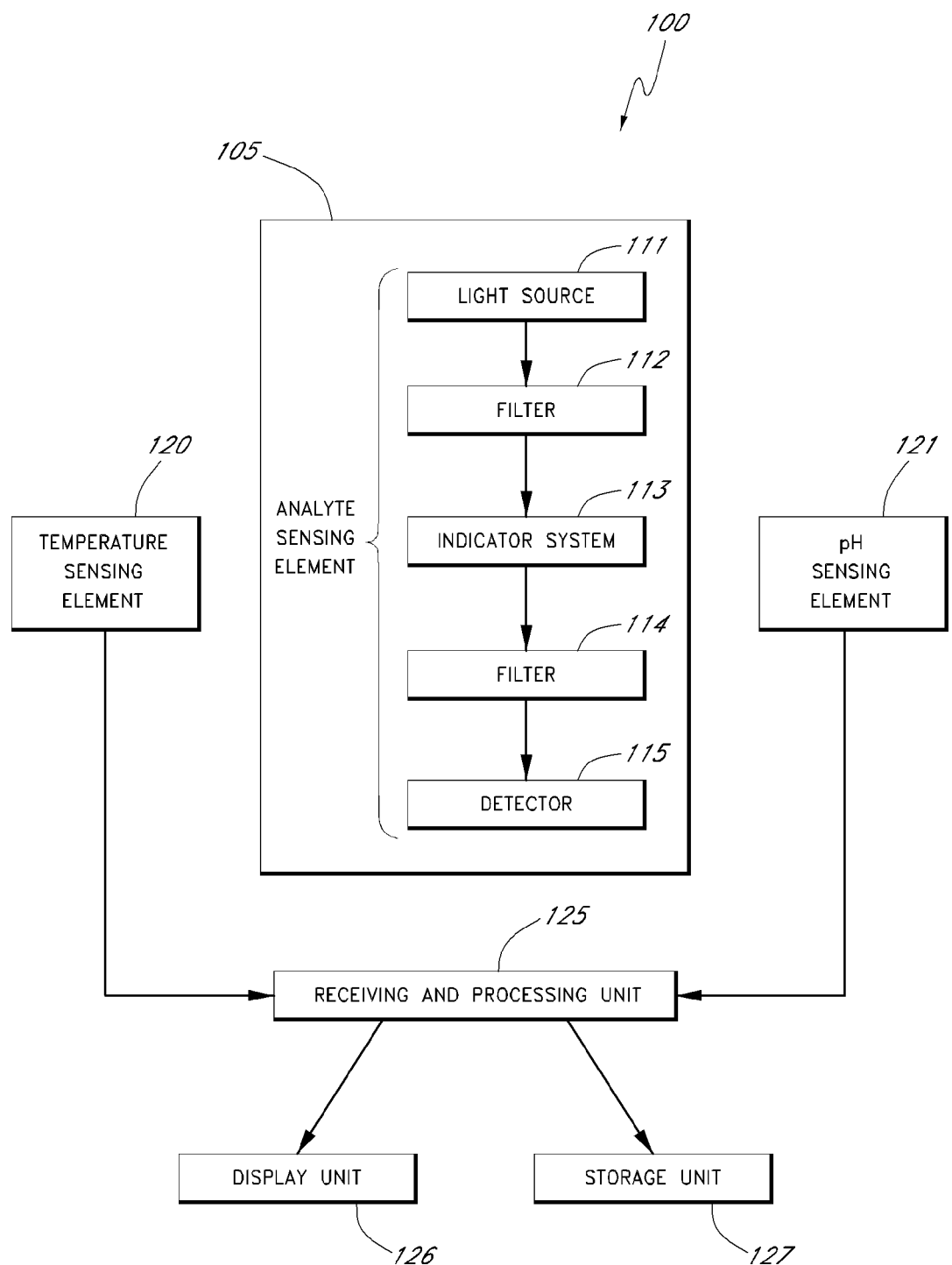
FIG. 1D is a flow chart schematically illustrating the sensing mechanism of one embodiment of the present invention which includes a temperature sensing element, an analyte sensing element, and a pH sensing element.
Figure 1E:
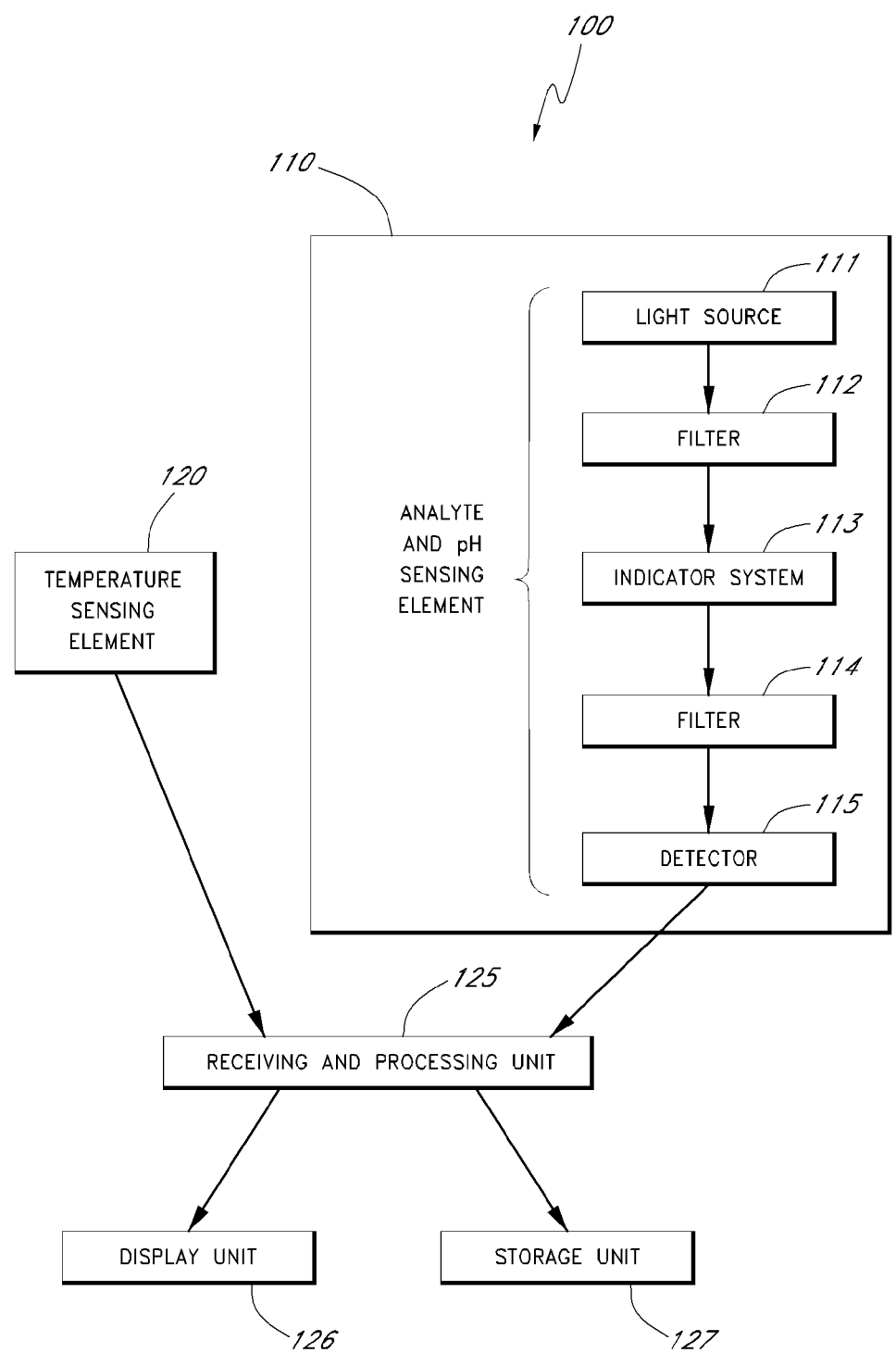
FIG. 1E is a flow chart schematically illustrating the sensing mechanism of one embodiment of the present invention which includes a temperature sensing element and a pH and analyte sensing element.

FIGS. 1A through 1E are flow charts illustrating the sensing mechanism corresponding to some embodiments of the measurement devices 100 disclosed herein. These flow charts may correspond to the sensing mechanism of an in vitro measurement device for use on the laboratory bench top, or they may correspond to the sensing mechanism of a device used for in vivo analyte sensing. As schematically illustrated in FIG. 1A, some embodiments of the measurement devices disclosed herein include at least one analyte sensing element 105, and may include at least one temperature sensing element 120. Other configurations of measurement devices, differing from the configuration illustrated in FIG. 1A, are schematically illustrated in FIGS. 1B through 1E. FIG. 1B, for instance, schematically illustrates a measurement device 100 having an analyte sensing element 105 and a pH sensing element 121, but lacking the temperature sensing element 120 of the configuration illustrated in FIG. 1A. FIG. 1C schematically illustrates a measurement device 100 having a combination analyte and pH sensing element 110, instead of the distinct analyte and pH sensing elements as shown in FIG. 1B. FIG. 1D schematically illustrates a configuration having an analyte sensing element 105, a temperature sensing element 120, and a pH sensing element 121. FIG. 1E schematically illustrates a configuration having the combination analyte and pH sensing element 110 of FIG. 1C along with a temperature sensing element 120. The analyte sensing element 105 may include at least one light source 111, at least one detector 115, and an indicator system 113. The indicator system 113 includes the sensing moieties—including at least one fluorophore and at least one binding moiety. In some embodiments, when the sensing moieties contact a sample containing the analyte of interest, a reversible, equilibrium-based, affinity-driven binding interaction between the analyte and the at least one binding moiety is established. This binding interaction alters the binding moiety's relationship with the fluorophore, such that when the fluorophore is excited by light from the at least one light source 111, its fluorescent emission is different depending on the extent to which analyte has been bound by the binding moiety. Thus, emission from the fluorophore is indicative of the concentration of analyte in the sample. In some embodiments, emission from the fluorophore may also be indicative of the pH of the sample. If this is the case, fluorescent emissions may be used to determine pH and analyte concentration as described in U.S. application Ser. No. 11/671,880, entitled "Optical Determination of pH and Glucose," filed Feb. 6, 2007, hereby incorporated by reference herein in its entirety. Whether indicative of analyte concentration, pH, or both, the fluorescent emission generated by the fluorophore (and modulated by the binding moiety) is detected by the detector 115 which generates a signal indicative of the emission (and thus also the analyte concentration and/or the pH) which is passed to the receiving and processing unit 125. The receiving and processing unit 125 is configured to estimate the concentration of the analyte in the sample based on one or more signals indicative of analyte concentration—such as the intensities of the fluorescent emissions. In some embodiments, the receiving and processing unit 125 may be further configured to generate temperature and/or pH corrected estimates of analyte concentration. The receiving and processing unit 125 may correct for temperature by receiving and taking into account one or more signals indicative of temperature generated by the temperature sensing element 120, as schematically illustrated in FIGS. 1A, 1D, and 1E. The receiving and processing unit 125 may correct for pH by receiving and taking into account one or more signals indicative of pH generated either by the pH sensing element 121, as schematically illustrated in FIGS. 1B and 1D, or by the analyte and pH sensing element 110. The receiving and processing unit 125 may employ various methods and algorithms of adjusting the estimated concentration based on the signal indicative of temperature, or the signal indicative of pH, or both, as described in further detail below. Estimated concentrations may be displayed in a display unit 126 and/or stored in a storage unit 127, as schematically illustrated in FIGS. 1A through 1E. Depending on the embodiment, any quantity related to analyte concentration (such as quantities derived in whole or in part from measurements of optical intensity) may be displayed in the display unit 126 and/or stored in the storage unit 127, including, but not limited to the measured fluorescent intensities emitted by the fluorophores, the temperature of the sample, and the pH of the sample. In addition, as schematically illustrated in FIGS. 1A through 1E, some embodiments of the measurement device 100 include one or more filters 112 located between the light source 111 and indicator system 113, and/or one or more filters 114 located between the indicator system 113 and the detector 115. The filter 112 may serve to select particular wavelengths of light for excitation of the fluorophore, while the filter 114 may serve to select particular wavelengths of light for detection. Other optical components may also be utilized (that are not shown in FIGS. 1A through 1E) including, but not limited to, mirrors, collimating and/or focusing lenses, beam splitters, etc. (See, e.g., FIGS. 2A, 2B, and 2C below.)

In some embodiments, the measurement device 100 may include a controller unit (not shown in FIGS. 1A through 1E) which controls various operations of the measurement device 100 including, but not limited to, control of the light sources, control of detectors, and responding to operator input or actions. The controller unit can be any type known in the art and capable of controlling the measuring device including, but not limited to, a microprocessor, an embedded processor, a multiprocessor, a general purpose computer, a special purpose processor, a microcontroller, a programmable gate array or any combination thereof.

Analyte Sensing Elements, pH Sensing Elements, and Analyte and pH Sensing Elements Various measurement devices disclosed herein include an analyte sensing element or an element capable of sensing both analyte concentration and pH—referred to herein as an analyte and pH sensing element. The latter dual purpose elements are schematically illustrated, for example, in FIGS. 1C and 1E. However, as indicated by FIGS. 1B and 1D, various embodiments of the measurement devices 100 disclosed herein may include an analyte sensing element 105, and a pH sensing element 121 separate from the analyte sensing element 105. When the pH sensing element 121 is distinct from the analyte sensing element 105, it may consist of any of a number of standard pH sensing devices which are known in the art so long as the device is properly sized and is capable of generating a signal indicative of pH which exhibits sufficient accuracy and precision to serve as a basis for applying pH correction to a signal indicative of analyte concentration. Of course, in measurement devices 100 that do not implement pH correction, such as those corresponding to the schematic illustration of FIG. 1A, a pH sensing element is not needed for this purpose and may be omitted.

An analyte sensing element may be configured to generate a signal indicative of the analyte concentration of a sample and may include at least one light source, an indicator system, and at least one detector. In some embodiments, the indicator system (described more fully below) may include at least one type of fluorophore and at least one type of binding moiety (each described in greater detail below), and in some embodiments, an immobilizing medium whose presence may prevent some of the fluorophores and/or some of the binding moieties from freely diffusing through the sample (as described in greater detail below). In some embodiments, the fluorophore emits a fluorescence having an intensity in response to light from the at least one light source. In some embodiments, the binding moiety is capable of binding the analyte and is operably coupled to the fluorophore, such that when the sample contacts the binding moiety the intensity is indicative of the concentration of the analyte. In some embodiments, the analyte sensing element includes at least one detector which may be configured to detect the intensity and generate a signal indicative of the analyte concentration of the sample in response to the intensity.

Likewise, a dual purpose, analyte and pH sensing element may be configured to generate one or more signals indicative of the analyte concentration of a sample and the pH of the sample. In some embodiments, an analyte and pH sensing element may include at least one light source, an indicator system, and at least one detector, similarly to the analyte sensing elements described in the preceding paragraph. Thus, in some embodiments, the indicator system (described more fully below) may include at least one type of fluorophore and at least one type of binding moiety (each described in greater detail below), and in some embodiments, an immobilizing medium whose presence may prevent some of the fluorophores and/or some of the binding moieties from freely diffusing through the sample (as described in greater detail below). In some embodiments, the fluorophore emits a fluorescence having an intensity in response to light from the at least one light source. In some embodiments, the binding moiety is capable of binding the analyte and is operably coupled to the fluorophore, such that when the sample contacts the binding moiety the intensity is indicative of the concentration of analyte in the sample and the pH of the sample. In some embodiments, the analyte and pH sensing element includes at least one detector which may be configured to detect the intensity and generate one or more signals indicative of the analyte concentration of the sample and the pH of the sample in response to the intensity.

Some of the measurement devices disclosed herein, only employ a single type of fluorophore and a single light source. However, it should be understood that some embodiments of the measurement devices disclosed herein employ more than one type of fluorophore. Furthermore, some embodiments of measurement devices employing multiple types of fluorophores may also employ more than one light source. Similarly, embodiments employing more than one type of fluorophore may also employ more than one detector. In certain such embodiments, the single detector may be a spectrometer.

However, dual light source and dual detector configurations are not necessarily limited to configurations utilizing multiple fluorophores, as these dual light source/detector configurations may offer other advantages. For instance, a dual light source configuration might advantageously allow one light source to serve as a reference for the other, or a dual light source configuration might be useful for measurement devices employing ratiometric pH determination as disclosed in U.S. Pat. No. 7,751,863, entitled "Optical Determination of pH and Glucose," which is hereby incorporated herein by reference in its entirety. Methods and/or algorithms for determining pH based on the ratio of two fluorescent emission signals are discussed below, as well as described in the aforementioned patent. In some embodiments, these methods may be implemented in a measurement device employing a combination analyte and pH sensing element which utilizes a dual light source configuration, as described below with reference to FIGS. 2A through 2C.

Figure 2A:
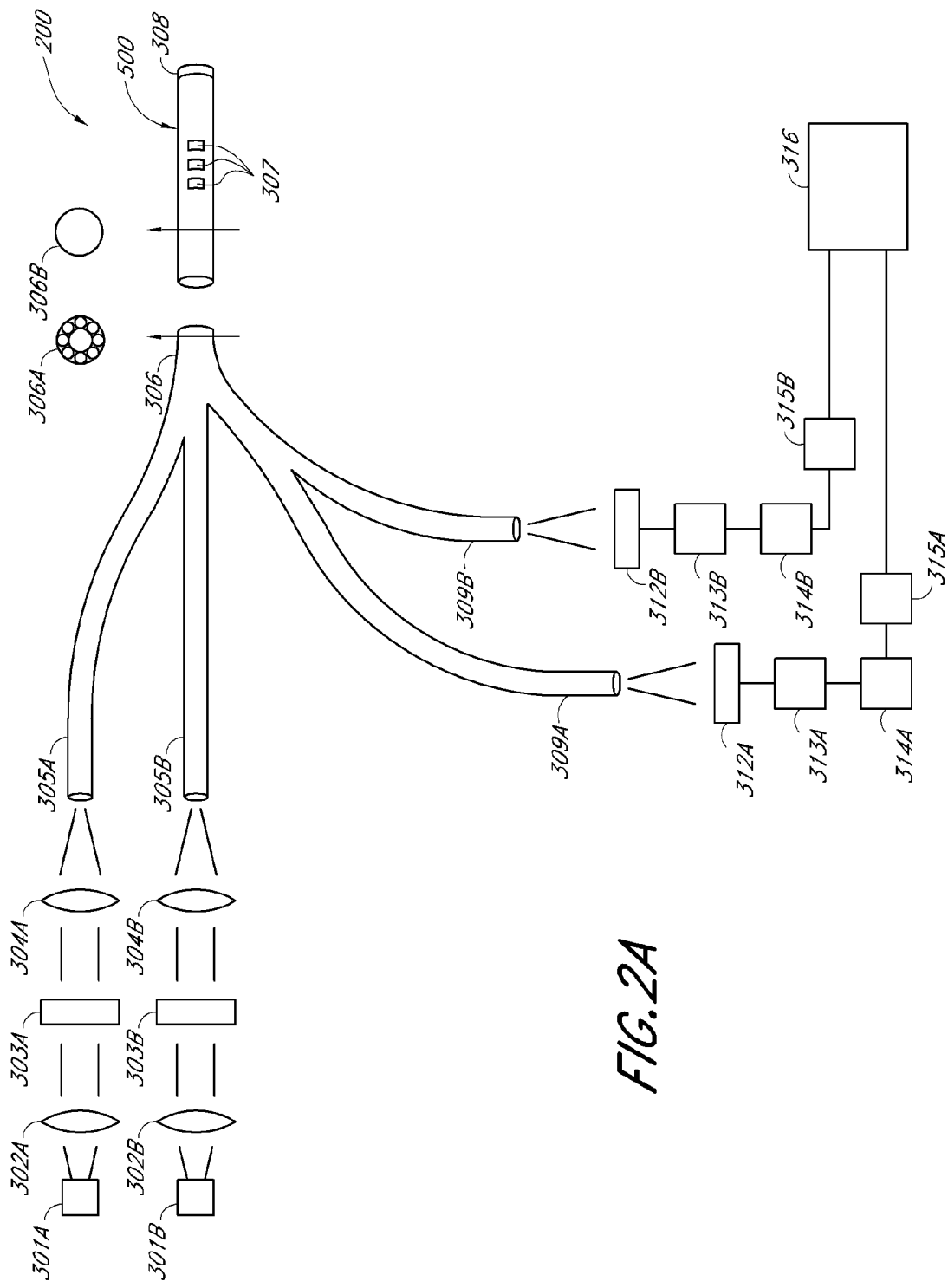
FIG. 2A schematically illustrates a dual light source, dual detector measurement device in accordance with certain embodiments disclosed herein.

Accordingly, embodiments of the measurement devices disclosed herein may configure light sources, detectors, and one or more fluorophores and binding moieties in a variety of ways. For example, FIG. 2A schematically illustrates a two light source measurement device in accordance with certain preferred embodiments of the present invention. With reference to FIG. 2A, the two light sources, 301A and 301B, each generate excitation light. In some embodiments, each of the two light sources 301A and 301B generates excitation light over a different range of wavelengths. In certain such embodiments, the excitation light generated by light source 301A falls within a wavelength range appropriate to cause an emission of a first type, and the excitation light generated by light source 301B falls within a wavelength range appropriate to cause an emission of a second type. In some embodiments, the ranges are partially overlapping, while in other embodiments, the ranges are fully non-overlapping.

The excitation light generated by light sources 301A and 301B may be transmitted (as illustrated) through collimator lenses 302A and 302B. The collimator lenses 302A and 302B may be aspheric lenses, but other types of collimator lenses may also be employed.

In certain embodiments, light exiting from the collimator lenses 302A and 302B may be transmitted (as illustrated) to interference filters 303A and 303B. In some embodiments, each interference filter 303A and 303B may attenuate or block a portion of the wavelength ranges generated by light sources other than the corresponding light source 301A and 301B. For instance, in certain such embodiments, interference filter 303A may pass light generated by light source 301A, but may severely attenuate light generated by light source 301B. Interference filter 303B may function analogously. In certain embodiments, each interference filter 303A and 303B blocks the wavelength range that overlaps with the wavelength range corresponding to emission by the one or more types of fluorophores. For example, if a measurement system employs a blue excitation light to produce a green emission, then an interference filter may in some embodiments preferably be used to narrow the band of blue excitation, because the blue excitation light may comprise both blue and green light. An unfiltered excitation blue that comprises green light can produce inaccurate green emission signal because the green light from the excitation light will add to the green emission signal of the fluorophore to produce a green light of greater intensity.

The interference filters 303A and 303B can be short or long pass filters that block all wavelengths beyond a certain maximum or minimum wavelength. The interference filters 303A and 303B can be band pass filters that only allow a particular band of wavelengths to pass through the filters. In certain embodiments, the measurement device employs interference filters 303A and 303B that are band pass filters because, in certain embodiments, the light sources 301A and 301B generate light of overlapping wavelength ranges. Thus, the use of non-overlapping band pass filters 303A and 303B may allow the measurement device to generate excitation light in distinct bands such that light generated by the light source 301A selectively creates only excitation of a first type, and light generated by 301B selectively creates only excitation of a second type. In this manner, in some embodiments, each light source may be tailored to create a particular type of emission.

In certain embodiments, light exiting from interference filters 303A and 303B may be focused (as illustrated) by focusing lenses 304A and 304B into fiber optic lines 305A and 305B. The fiber optic lines 305A and 305B carry the filtered excitation light to the indicator system 307, which is contained within a sensor probe 200. In some embodiments, the sensor probe 200 includes a protective housing 500 which serves to protect the indicator system 307 contained within the sensor probe 200. In some embodiments, the indicator system is immobilized in an immobilizing medium within the sensor probe 200, as described herein. In some embodiments, the fiber optic lines 305A and 305B merge into a single fiber 306 that is continuous with the sensor probe 200. In other embodiments, the fiber optic lines 305A and 305B remain distinct (although not shown in FIG. 2A). In certain embodiments employing two types of fluorophores, the fiber optic lines 305A and 305B may remain distinct and be configured so as to keep the two types of fluorophores spatially distinct/separated so that each type of fluorophore may only interact with light traveling to the indicator system down a single optical fiber (that is light generated from one of the light sources). In certain other embodiments, the fiber optic lines 305A and 305B may be kept distinct so that one line may be configured so that light traveling down the line never interacts with any fluorophore—in this manner creating a reference signal and keeping it free from optical contamination by the optically emitting fluorophore interacting with light travelling down the other fiber optic line. The cross-sections of the fibers may vary (as illustrated) from a bundle of fibers surrounding a central optical fiber 306A to a single fiber 306B.

The indicator system 307 contained within the sensor probe 200 responds to the excitation light by emitting light (as described in detail herein). In certain embodiments (as illustrated in FIG. 2A), the emission light signals generated by the indicator system 307 as well as the excitation light signals are transmitted back out of the sensor probe 200 into the fiber optic outlet lines 309A and 309B. In some embodiments, each fiber optic outlet line 309A and 309B substantially carries light corresponding to one type of fluorescent emission. For example, outlet line 309A carries light away from the sensor probe 200 substantially consisting of a first type of fluorescent emission, and outlet line 309B carries light away from the sensor probe 200 substantially consisting of a second type of fluorescent emission. In measuring devices configured with a mirror 308 beyond the indicator system 307 at the far end of the sensor probe 200 (such as shown in FIG. 2A), a portion of the light transmitted back out of the sensor probe 200 into the fiber optic outlet lines 309A and 309B is light that has been reflected by the mirror 308. However, other embodiments may lack a mirror.

In the measurement device schematically illustrated in FIG. 2A, the fiber optic outlet lines 309A and 309B are augmented by including two interference filters 312A and 312B; and two detectors 313A and 313B. In certain embodiments, the interference filter 312A is configured to substantially block the excitation light generated by light source 301A (and, in some embodiments, additionally block the excitation and emission/fluorescence wavelengths corresponding to light source 301B) and substantially pass the fluorescence emitted and generated by the indicator system in response to irradiation by light source 301A. As a result, this fluorescence passes to detector 313A where it is detected. The detector 313A may be any device capable of measuring fluorescent intensity at an appropriate wavelength or over an appropriate range of wavelengths, including, but not limited to, detectors consisting of one or more photodiodes. In certain embodiments, the detector 313A produces a signal that is amplified by the amplifier 314A and converted into a digital signal by analog-to-digital converter 315A and transmitted to a receiving and processing unit 316. The receiving and processing unit 316 may comprise a data processing device of any type known in the art, for example, a microprocessor, an embedded processor, a multiprocessor, a general purpose computer, a special purpose processor, any computational device, a digital signal processor, a microcontroller, a programmable gate array or any combination thereof.

The interference filter 312B, detector 313B, amplifier 314B, and analog-to-digital converter 315B may function in a similar manner with respect to fluorescence emitted and generated by the indicator system 307 in response to irradiation by light source 301B. In some embodiments, the receiving and processing unit 316, after receiving digital signals from the analog-to-digital converters 315A and 315B may employ various calculation schemes disclosed herein to estimate an analyte concentration, and in some embodiments, the glucose concentration of a sample. In some embodiments, the receiving and processing unit 316 may employ a temperature correction and/or pH correction method or algorithm such as those described in detail below. In addition, in some embodiments, the receiving and processing unit 316 may transmit data and/or results to a storage unit which may store the data and/or results (e.g. on an optical or magnetic disc or other digital medium). In some embodiments, the receiving and processing unit 316 may transmit data and/or results to a display unit which may display the data and/or results (e.g. on a print-out or display screen).

Figure 2B:
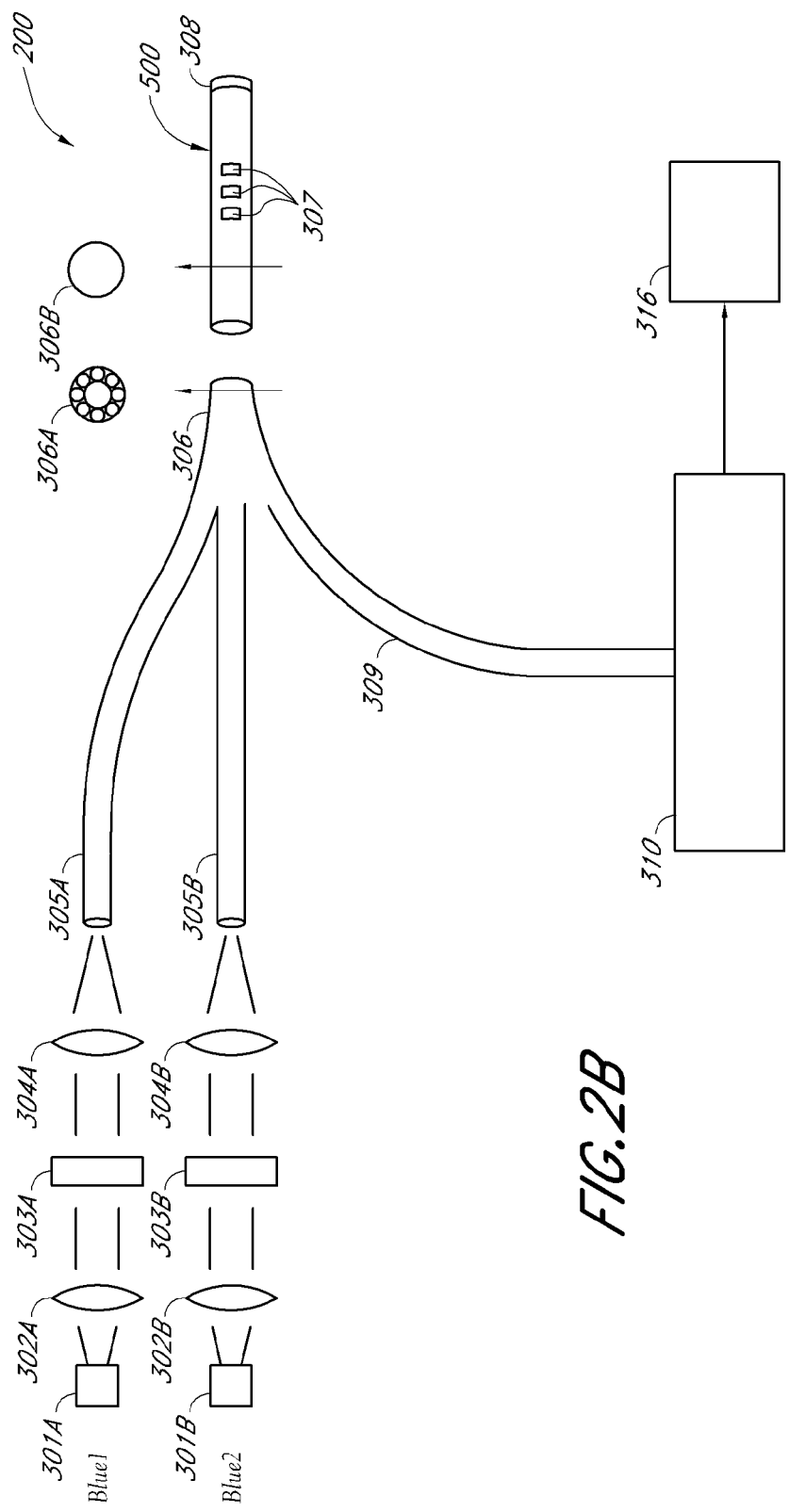
FIG. 2B schematically illustrates a dual light source measurement device incorporating a microspectrometer and/or spectrometer in accordance with certain embodiments disclosed herein.

Another embodiment of an measurement device is schematically illustrated in FIG. 2B. Like the device schematically illustrated in FIG. 2A, the device depicted in FIG. 2B is a two light source measurement device. However, the device depicted in FIG. 2B differs from that depicted in FIG. 2A in that it utilizes a spectrophotometer 310 instead of the multiple detectors 312A and 312B shown in FIG. 2A. In some embodiments, the spectrophotometer may be a ultraviolet/visible microspectrometer such as those manufactured by Boehringer Ingelheim or Ocean Optic Inc. However, in principle, any spectrophotometer which measures optical intensity over the appropriate wavelength range(s) may be used.

As schematically illustrated in FIG. 2B, the spectrophotometer 310 receives light from the indicator system 307 via a single fiber optic outlet line 309. In some embodiments, a spectrophotometer 310 such as that depicted in FIG. 2B is capable of measuring optical intensity over a broader range of wavelengths than the detectors 312A and 312B. Accordingly, in some embodiments, one spectrophotometer 310 fed by a single optical fiber 309 may provide the detection functionality of multiple detectors and in some embodiments much more flexibility. However, in some embodiments there are other device design tradeoffs such as, for example, potential cost, complexity, size, and power requirements.

Also absent from the measurement device depicted in FIG. 2B are the filters 312A and 312B; the amplifiers 314A and 314B; and the analog-to-digital converters 315A and 315B exhibited by the device schematically illustrated in FIG. 2A. Similar functionality is provided, in some embodiments, by the spectrophotometer 310 itself. The spectrophotometer 310 transmits data and/or results to a receiving and processing unit 316 as was described in reference to FIG. 2A. The receiving and processing units 316 of FIGS. 2A and 2B may function similarly, as described above, depending on the embodiment.

Figure 2C:
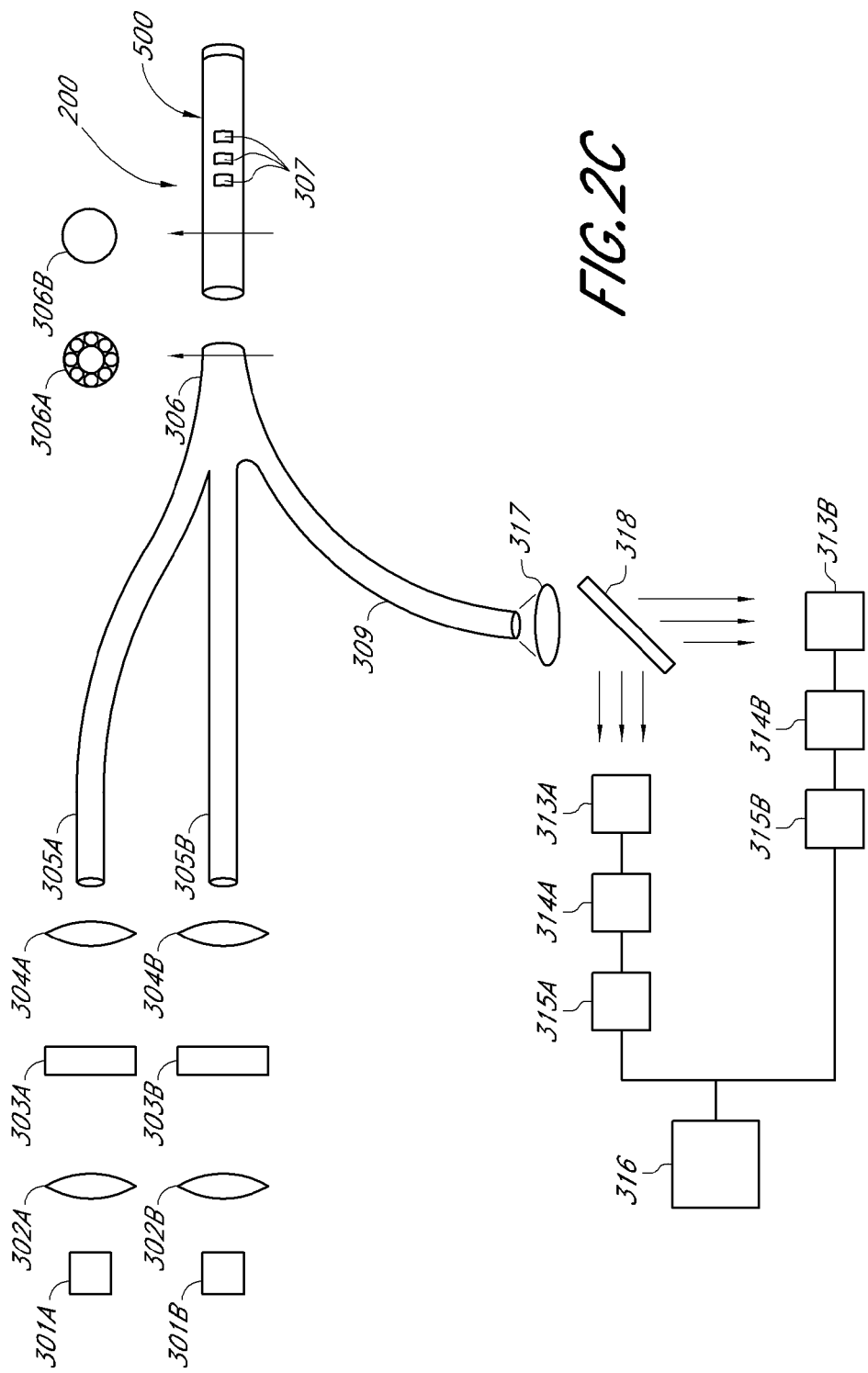
FIG. 2C schematically illustrates a dual light source, dual detector measurement system incorporating a beam splitter in accordance with certain embodiments disclosed herein.

Yet another embodiment of an analyte measuring device is schematically illustrated in FIG. 2C. Like the devices schematically illustrated in FIGS. 2A, and 2B, the device depicted in FIG. 2C is a two light source measurement device. However, the device depicted in FIG. 2C utilizes a single fiber optic outlet line 309 which transmits light to a single collimator lens 317 and then on to beam splitters 318. In some embodiments, the beam splitter 318 substantially reflects light generated by a first type of fluorescent emission, and substantially transmits light generated by a second type of fluorescent emission. The reflected light is transmitted to a detector 313A, which generates an analogue signal indicative of the intensity of the reflected light. The signal is amplified by the amplifier 314A and transmitted to the analog-to-digital converter 315A where it is digitized. The digital signal is then transmitted to the receiving and processing unit 316. Light transmitted by the beam splitter 318 is detected by the detector 313B, amplified by the amplifier 314B, digitized by the analog-to-digital converter 315B, and transmitted to the receiving and processing unit 316 in parallel fashion to the light reflected by the beam splitter 318. As described above, the receiving and processing unit 316 may be a data processing device of any type known in the art, for example, a microprocessor, an embedded processor, a multiprocessor, a general purpose computer, a special purpose processor, any computational device, a digital signal processor, a microcontroller, a programmable gate array or any combination thereof.

The beam splitter 318 may be an interference filter designed to work at a substantially forty-five degree angle, as shown in FIG. 2C. In certain embodiments, the beam splitter 318 comprises a glass surface with a coating that reflects light having a certain wavelength and transmits all other light. The beam splitter 318 can be positioned at a substantially forty-five degree angle relative the direction of the light traveling from the collimator lens 317. As described above, in some embodiments, the beam splitter 318 is configured in such a way that light generated by different types of fluorescent emission are detected separately by a dedicated detector 313A and 313B.

Notably absent from the embodiment schematically depicted in FIG. 2C versus that depicted in FIG. 2B are the filters 312A and 312B. In certain embodiments employing a beam splitter 318 renders additional filtering by the dedicated filters 312A and 312B unnecessary. Multiple fiber optic outlets lines may also be superfluous when a beam splitter is employed as is apparent from comparing the embodiments schematically illustrated in FIG. 2A (utilizing fiber optic outlet lines 309A and 309B) and FIG. 2C (utilizing a single line 309). However, there are design trade-offs between the embodiments schematically illustrated in all three FIGS. 2A, 2B, and 2C as appreciated by one skilled in the art. Moreover, the embodiments illustrated in FIGS. 2A, 2B, and 2C are merely illustrative of the types of device configurations which are possible. These example embodiments are not meant to be exhaustive and the particular design chosen is not necessarily critical to the working of the various measurement devices disclosed herein.

Temperature Sensing Elements

In addition to an analyte sensing element, a pH sensing element, or a combination analyte and pH sensing element, the measurement device may contain a temperature sensing element, such as, for example, a thermistor or a thermocouple, located within the sensor probe 200. In some embodiments, the temperature sensing element is located at or near the analyte sensing chemistry (i.e. the indicator system) such that the temperature being measured is characteristic of the temperature of the analyte solution where the concentration is being measured. In some embodiments, the temperature sensing element may be co-located with the indicator system within a distal tip of the sensor probe. A suitable temperature sensing element is preferably small enough such that the sensor probe 200 does not have to be increased in size substantially to accommodate it.

The temperature sensing element is particularly important when the analyte sensing chemistry, such as a fluorophore system, is affected by temperature change. As described above and in greater detail below, in some embodiments, the fluorescence intensity emitted by the fluorophore system is dependent on the temperature of the fluorophore system. By measuring the temperature of the fluorophore system, temperature induced variations in fluorophore fluorescence intensity can be accounted for, allowing for more accurate determination of analyte concentration, as more fully described below. For example, a fluorophore based glucose sensing chemistry may generate signals indicative of glucose concentration which are effected by the temperature at which the sensing is performed, and knowledge of the effect of temperature on these signals may be used to generate estimates of glucose concentration which are corrected for temperature.

Sensor Probe

FIG. 3 illustrates in greater detail a sensor probe 200 in accordance with an embodiment of the present invention. The sensor probe 200 comprises an optical fiber 10 with a distal end 12 disposed in a porous membrane sheath 14. The optical fiber 10 has cavities, such as holes 6A, in the fiber optic wall that can be formed by, for example, mechanical means such as drilling or cutting. The holes 6A in the optical fiber 10 can be filled with a suitable compound, such as a polymer. In some embodiments, the polymer is a hydrogel 8. In other embodiments of the sensor probe 200 as shown in FIG. 4, the optical fiber 10 does not have holes 6A, and instead, the hydrogel 8 is disposed in a space distal to the distal end 12 of the optical fiber 10 and proximal to the mirror 23. In some embodiments, the sensor probe 200 is configured to generate a signal indicative of glucose concentration. In some embodiments, the sensor probe 200 is configured for intravascular deployment.

In some embodiments, the porous membrane sheath 14 can be made from a polymeric material such as polyethylene, polycarbonate, polysulfone or polypropylene. Other materials can also be used to make the porous membrane sheath 14 such as zeolites, ceramics, metals, or combinations of these materials. In some embodiments, the porous membrane sheath 14 may be nanoporous. In other embodiments, the porous membrane sheath 14 may be microporous. In still other embodiments, the porous membrane sheath 14 may be mesoporous.

In some embodiments as shown in FIG. 4, the porous membrane sheath 14 is attached to the optical fiber 10 by a connector 16. For example, the connector 16 can be an elastic collar that holds the porous membrane sheath 14 in place by exerting a compressive force on the optical fiber 10, as shown in FIG. 4. In other embodiments, the connector 16 is an adhesive or a thermal weld.

In some embodiments, such as that shown in FIG. 3, a mirror 23 and a temperature sensing element such as a thermistor 25 may be placed within the porous membrane sheath 14 distal the distal end 12 of the optical fiber 10. Thermistor leads 27 can be made to run in a space between the optical fiber 10 and porous membrane sheath 14. Although a thermistor 25 is shown, other devices such as a thermocouple, pressure transducer, an oxygen sensor, a carbon dioxide sensor or a pH sensor for example can be used instead.

In some embodiments as shown in FIG. 4, the distal end 18 of the porous membrane sheath 14 is open and can be sealed with, for example, an adhesive 20. In some embodiments, the adhesive 20 can comprise a polymerizable material that can fill the distal end 18 and then be polymerized into a plug. Alternatively, in other embodiments the distal end 18 can be thermally welded by melting a portion of the polymeric material on the distal end 18, closing the opening and allowing the melted polymeric material to resolidify. In other embodiments as shown in FIG. 3, a polymeric plug 21 can be inserted into the distal end 18 and thermally heated to weld the plug to the porous membrane sheath 14. Thermoplastic polymeric materials such as polyethylene, polypropylene, polycarbonate and polysulfone are particularly suited for thermal welding. In other embodiments, the distal end 18 of the porous membrane sheath 14 can be sealed against the optical fiber 10.

After the porous membrane sheath 14 is attached to the optical fiber 10 and the distal end 18 of the porous membrane sheath 14 is sealed, the sensor probe 200 can be vacuum filled with a first solution comprising a monomer, a crosslinker and a first initiator. Vacuum filling of a polymerizable solution through a porous membrane and into a cavity in a sensor is described in detail in U.S. Pat. No. 5,618,587 to Markle et al.; incorporated herein in its entirety by reference thereto. The first solution is allowed to fill the cavity 6 within the optical fiber 10.

In some embodiments, the first solution is aqueous and the monomer, the crosslinker and the first initiator are soluble in water. For example, in some embodiments, the monomer is acrylamide, the crosslinker is bisacrylamide and the first initiator is ammonium persulfate. In other embodiments, the monomer is dimethylacrylamide or N-hydroxymethylacrylamide. By increasing the concentrations of the monomer and/or crosslinker, the porosity of the resulting gel can be decreased. Conversely, by decreasing the concentrations of the monomer and/or crosslinker, the porosity of the resulting gel can be increased. Other types of monomers and crosslinkers are also contemplated. In other embodiments, the first solution further comprises an analyte indicator system comprising a fluorophore and an analyte binding moiety that functions to quench the fluorescent emission of the fluorophore by an amount related to the concentration of the analyte. In some embodiments, the fluorophore and analyte binding moiety are immobilized during polymerization, such that the fluorophore and analyte binding moiety are operably coupled. In other embodiments, the fluorophore and analyte binding moiety are covalently linked. The indicator system chemistry may also be covalently linked to the polymeric matrix.

In some embodiments, after the sensor probe 200 is filled with the first solution, the optical fiber 10 and the first solution filled porous membrane sheath 14 and cavity 6 are transferred to and immersed into a second solution comprising a second initiator. In some embodiments, the second solution is aqueous and the second initiator is tetramethylethylenediamine (TEMED). In some embodiments, the second solution further comprises the same fluorescent dye and/or quencher found in the first solution and in substantially the same concentrations.

By having the fluorescent dye and quencher in both the first solution and the second solution, diffusion of fluorescent dye and quencher out of the first solution and into the second solution can be reduced. In some embodiments where a second solution is used, the second solution further comprises monomer in substantially the same concentration as in the first solution. This reduces diffusion of monomer out of the first solution by reducing the monomer gradient between the first solution and the second solution.

In some embodiments, at or approximately at the interface between the first and second solutions, the first initiator and the second initiator can react together to generate a radical. In some embodiments, the first initiator and the second initiator react together in a redox reaction. In other embodiments, the radical can be generated by thermal decomposition, photolytic initiation or initiation by ionizing radiation. In these other embodiments, the radical may be generated anywhere in the first solution. Once the radical is generated, the radical can then initiate polymerization of the monomer and crosslinker in the first solution.

When the radical is generated via a redox reaction as described herein, the polymerization proceeds generally from the interface between the first and second solutions to the interior of the porous membrane sheath 14 and towards the cavity in the optical fiber 10. Rapid initiation of polymerization can help reduce the amount of first initiator that can diffuse from the first solution and into the second solution. Reducing the amount of first initiator that diffuses out of the first solution helps reduce polymerization of monomer outside the porous membrane sheath 14 which helps in forming a smooth external surface. Polymerization of the monomer and crosslinker results in a hydrogel 8 that in some embodiments substantially immobilizes the indicator system, forming the sensor probe 200. Further variations on polymerization methodologies are disclosed in U.S. Patent Publ. No. 2008/0187655; incorporated herein in its entirety by reference thereto.

With reference to FIG. 5A, in certain embodiments, the sensor probe 200 is a solid optical fiber with a series holes 6A drilled straight through the sides of the optical fiber. In certain embodiments, the holes 6A are filled with the hydrogels 8. In certain embodiments, the series of holes 6A that are drilled through the sensor probe 200 are evenly spaced horizontally and evenly rotated around the sides of the sensor probe 200 to form a spiral or helical configuration. In certain embodiments, the series of holes 6A are drilled through the diameter of the sensor probe 200. With reference to FIG. 5B, in certain embodiments, the sensor probe 200 is a solid optical fiber with a series of holes 6A drilled through the sides of the fiber at an angle. In certain embodiments, the series of holes 6A drilled at an angle, which are filled with hydrogel 8, are evenly spaced horizontally and evenly rotated around the sides the sensor probe 200. With reference to FIG. 5C, in certain embodiments, the optical fiber comprises a groove 6B along the length of the optical fiber, wherein the groove 6B is filled with hydrogel 8. In certain embodiments, the depth of the groove 6B extends to the center of the optical fiber. In certain embodiments, the groove 6B spirals around the optical fiber. In certain embodiments, the groove 6B spirals around the optical fiber to complete at least one rotation. In certain embodiments, the groove spirals 6B around the optical fiber to complete multiple rotations around the optical fiber.

With reference to FIG. 5D, in certain embodiments, the sensor probe 200 is a solid optical fiber with triangular wedges 6C cut from the fiber. In certain embodiments, the triangular wedge areas 6C are filled with hydrogel 8. In certain embodiments, the triangular wedges cut-outs 6C are evenly spaced horizontally and around the sides of the sensor probe 200. In certain embodiments, all light traveling in the sensor probe 200 is transmitted through at least one hole 6A or groove 6B filled with hydrogel 8.

Figure 6:
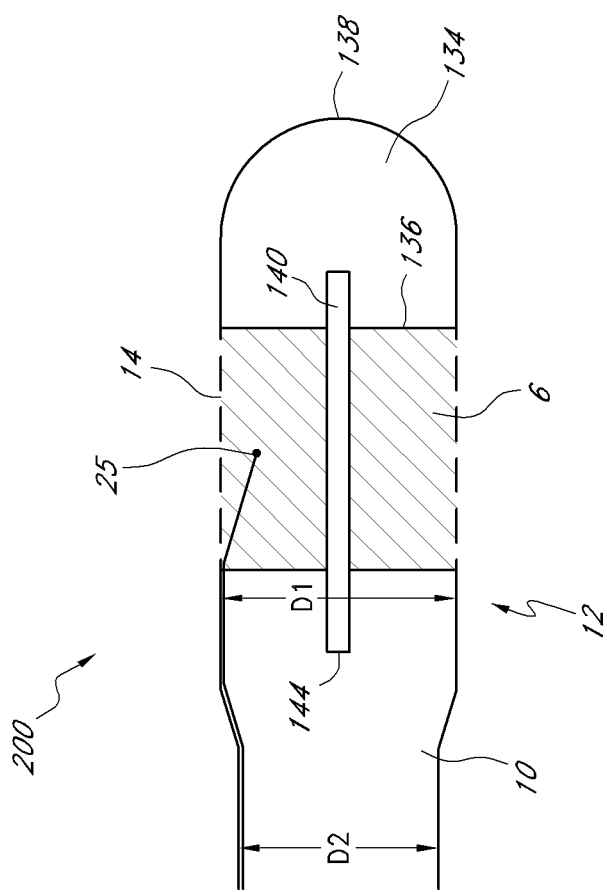
FIG. 6 shows a cross-sectional view of one embodiment of a sensor probe having a cavity in the distal portion of the sensor probe.

In certain embodiments, as illustrated in FIG. 6, the sensor probe 200 comprises an optical fiber 10 having a distal end 12, an atraumatic tip portion 134 having a proximal end 136 and a distal end 138, a cavity 6 between the distal end 12 of the optical fiber 10 and the proximal end 136 of the atraumatic tip portion 134, and a rod 140 connecting the distal end 12 of the optical fiber 10 to the proximal end 136 of the atraumatic tip portion 134. A hydrogel 8 containing the sensing chemistry, for example a fluorophore and quencher, fills the cavity 6. Also present within the cavity 6 is a temperature sensing element 25, such as thermocouple or thermistor. Covering the hydrogel filled cavity 6 is a selectively permeable membrane 14 that allows passage of the analyte being detected/sensed into and out of the hydrogel 8. It should, of course, be understood that the sensor probe 200 may be modified to generate signals indicative of the analyte concentration of various analytes by selecting, for example, an appropriate sensing chemistry, and if necessary, choosing an appropriate selectively permeable membrane 14.

The proximal portion of the sensor probe 200 comprises the proximal portion of the optical fiber 10. In some embodiments, the diameter, D1, of the distal portion of the sensor 2 is greater than the diameter, D2, of the proximal portion of the sensor 2. For example, the diameter D1 of the distal portion of the sensor probe 200 can be between about 0.0080 inches and 0.020 inches, while the diameter D2 of the proximal portion of the sensor probe 200 can be between about 0.005 inches to 0.015 inches. In some embodiments, the diameter D1 of the distal portion of the sensor probe 200 is about 0.012 inches, while the diameter D2 of the proximal portion of the sensor probe 200 is about 0.010 inches.

Indicator Systems

The indicator system includes the sensing moieties—including, in some embodiments, at least one type of fluorophore and at least one type of binding moiety. In some embodiments, when the sensing moieties contact a sample containing the analyte of interest, a reversible, equilibrium-based, affinity-driven binding interaction between the analyte and the at least one type of binding moiety is established. This binding interaction alters the binding moieties' relationship with the fluorophores, such that when the fluorophores are excited by light from the at least one light source, their fluorescent emission varies with the extent to which analyte has been bound by the binding moieties. Thus, emission from the one or more types of fluorophores is indicative of the concentration of analyte in the sample.

Accordingly, in some embodiments the indicator system includes at least one type of fluorophore which emits a fluorescence having an intensity in response to light from at least one light source. In certain such embodiments, the intensity is detectable by at least one detector. The indicator system further includes at least one type of binding moiety capable of binding the analyte. The at least one type of binding moiety is typically operably coupled to the at least one type of fluorophore such that when the sample contacts the at least one type of binding moiety the intensity (emitted in response to light from the at least one light source, as described above) is indicative of the concentration of the analyte. For example, a glucose binding moiety such as 3,3'-oBBV (described in detail below) that is coupled to a fluorescent dye such as HPTS-triLysMA (described in detail below) will quench the emission intensity of the fluorescent dye, wherein the extent of quenching is reduced upon glucose binding resulting in an increase in emission intensity related to glucose concentration. In some embodiments, the indicator system may include an immobilizing medium configured to prevent some of the fluorophores and/or some of the binding moieties from freely diffusing through the sample.

Fluorophores

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 Daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2$NH—), amide —(C=O)N—, ester —(C=O)—O—, ether. —O—, sulfide —S—, sulfone phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through the sulfonamide functional groups.

In some embodiments, useful dyes include pyranine derivatives (e.g. hydroxypyrene trisulfonamide derivatives and the like), which have the following formula:

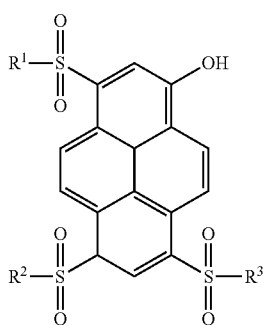

wherein $R^1$, $R^2$, $R^3$ are each —NHR$^4$, $R^4$ is —CH$_2$CH$_2$(—OCH$_2$CH$_2$—)$_n$X$^1$; wherein X$^1$ is —OH, —OCH$_3$COOH, —CONH$_2$, —SO$_3$H, —NH$_2$, or OMe; and n is between about 70 and 10,000. In one embodiment, the dyes may be bonded to a polymer through the sulfonamide functional groups. In other embodiments, the dye may be one of the polymeric derivatives of hydroxypyrene trisulfonic acid. In some embodiments, the fluorescent dye may be 8-hydroxypyrene-1,3,6-trisulfonate (HPTS). The counter-ions can be H$^+$, Na$^+$, or any other cation. HPTS has a molecular weight of less than 500 Daltons, so it will not stay within the polymer matrix, but it can be used with an anion exclusion membrane. The dyes may be used with a quencher comprising boronic acid, such as 3,3'-oBBV.

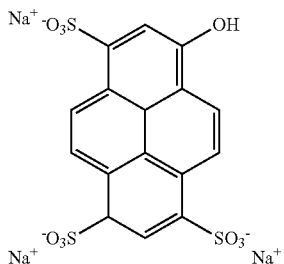

(the Na$^+$ salt of HPTS—"pyranine")

In some embodiments, dyes of the following generic structure may serve as suitable fluorophores:

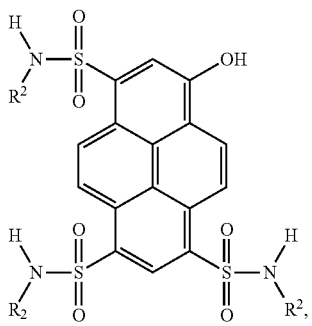

wherein:
R$^2$ is

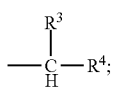

R$^3$ is —(CH$_2$)$_n$-A$^-$M$^+$,
  wherein n is 1-4,
    wherein A$^-$ is an anionic group selected from the group consisting of SO$_3^-$, HPO$_3^-$, CO$_2^-$ and

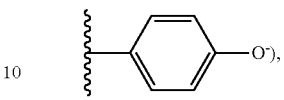

and
  wherein M$^+$ is a cationic group selected from the group consisting of H$^+$, an alkali metal ion, Li$^+$, Na$^+$, K$^+$, R$^+$, Cs$^+$, Fr$^+$, an onium ion and NR$_4^+$, wherein R is selected from the group consisting of alkyl, alkylaryl and aromatic groups);

R$^4$ is

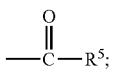

R$^5$ is selected from the group consisting of $$Y—(CH_2)_n—R^6 \text{ and } Y—[(CH_2)_{n'}—O]_n—[CH_2]_n—R^6,$$

wherein n is equal to 1-10, n' is equal to 2-4 and Y is selected from the group consisting of NH and O;

R$^6$ is selected from the group consisting of NHR$^7$, OR$^7$ and CO$_2$H; and

R$^7$ is H or an ethylenically unsaturated group selected from the group consisting of methacryloyl, acryloyl, styryl, acrylamide and methacrylamido.

In some embodiments, dyes of the following generic structure may serve as suitable fluorophores:

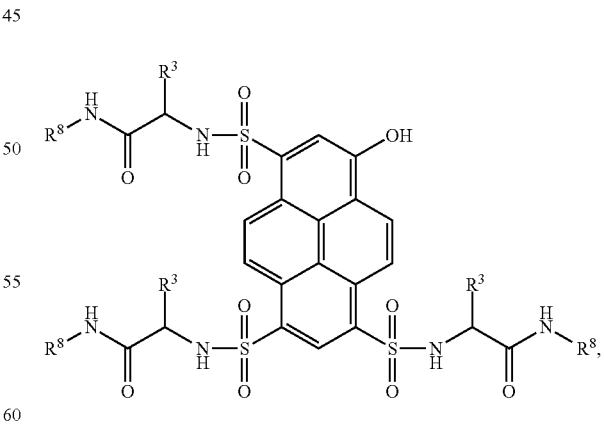

where:
R$^3$ is —(CH$_2$)$_n$-A$^-$M$^+$,
  wherein n is 1-4,
    wherein A$^-$ is an anionic group selected from the group consisting of SO$_3^-$, HPO$_3^-$, CO$_2^-$ and

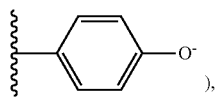

and wherein $M^+$ is a cationic group selected from the group consisting of $H^+$, an alkali metal ion, $Li^+$, $Na^+$, $K^+$, $Rb^+$, $Cs^+$, $Fr^+$, an onium ion and $NR_4^+$, wherein R is selected from the group consisting of alkyl, alkylaryl and aromatic groups);

$R^4$ is

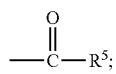

$R^8$ is selected from the group consisting of

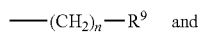

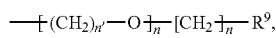

wherein n is equal to 1-10, n' is equal to 2-4;
$R^9$ is selected from the group consisting of $NHR^{10}$, $OR^{10}$ and $CO_2H$; and
$R^{10}$ is H or an ethylenically unsaturated group selected from the group consisting of methacryloyl, acryloyl, styryl, acrylamido and methacrylamido.

In another embodiment, the fluorescent dye may be polymers of 8-acetoxy-pyrene-1,3,6-N,N',N"-tris-(methacrylpropylamidosulfonamide) (acetoxy-HPTS-MA):

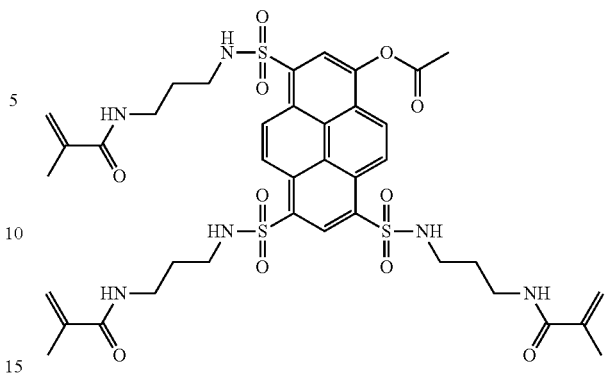

It is noted that dyes such as acetoxy-HPTS-MA (above) having no anionic groups, may not give very strong glucose response when operably coupled to a viologen quencher, particularly a viologen quencher having only a single boronic acid moiety.

In another embodiment, the fluorescent dye may be 8-hydroxy-pyrene-1,3,6-N,N',N"-tris-(carboxypropylsulfonamide) (HPTS-$CO_2$):

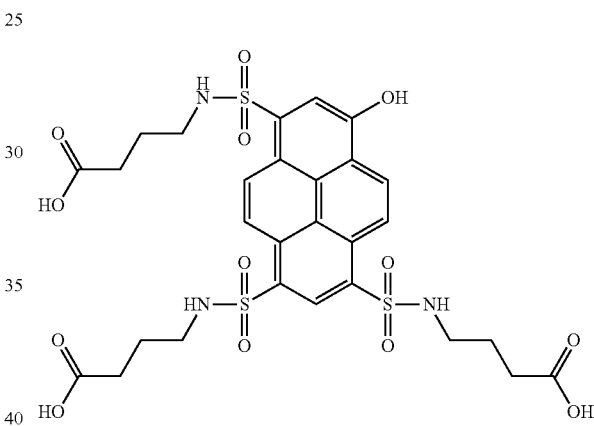

In another embodiment, the fluorescent dye may be 8-hydroxy-pyrene-1,3,6-N,N',N"-tris-(methoxypolyethoxyethyl (~125) sulfonamide) (HPTS-PEG):

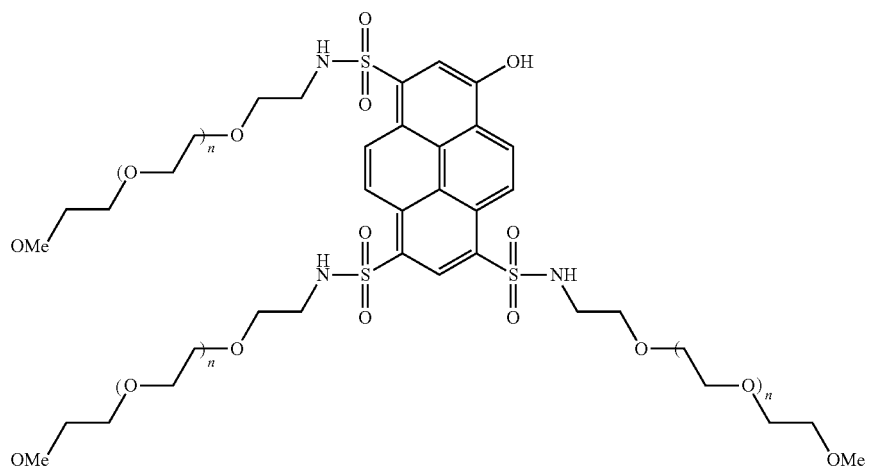 [SMILES: COCCOCCOCCNS(=O)(=O)c1cc(O)c2ccc3c(S(=O)(=O)NCCOCCOCCOC)cc(S(=O)(=O)NCCOCCOCCOC)c4ccc1c2c34]

It is noted that dyes such as HPTS-PEG (above) having no anionic groups, may not provide a very strong glucose response when operably coupled to a viologen quencher, particularly a viologen quencher having only a single boronic acid moiety.

Representative dyes as discrete compounds are the tris adducts formed by reacting 8-acetoxypyrene-1,3,6-trisulfonylchloride (HPTS-Cl) with an amino acid, such as amino butyric acid. Hydroxypyrene trisulfonamide dyes bonded to a polymer and bearing one or more anionic groups are most preferred, such as copolymers of 8-hydroxypyrene-1-N-(methacrylamidopropylsulfonamido)-N',N"-3,6-bis(carboxypropylsulfonamide) HPTS-CO$_2$-MA with HEMA, PEGMA, and the like.

In another embodiment, the fluorescent dye may be HPTS-TriCys-MA:

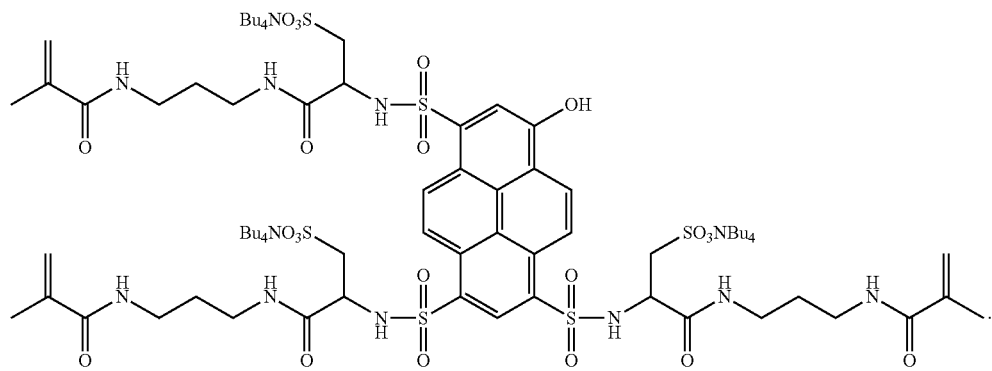

This dye is also referred to as just HPTS-Cys-MA. The dye may be used with a quencher comprising boronic acid, such as 3,3'-oBBV.

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counter-ions besides NBu$_4^+$ may be used, including positively charged metals, e.g., Na$^+$. In other variations, the sulfonic acid groups may be replaced with e.g., phosphoric, carboxylic, etc. functional groups.

Another suitable dye is HPTS-LysMA, which is pictured below as follows:

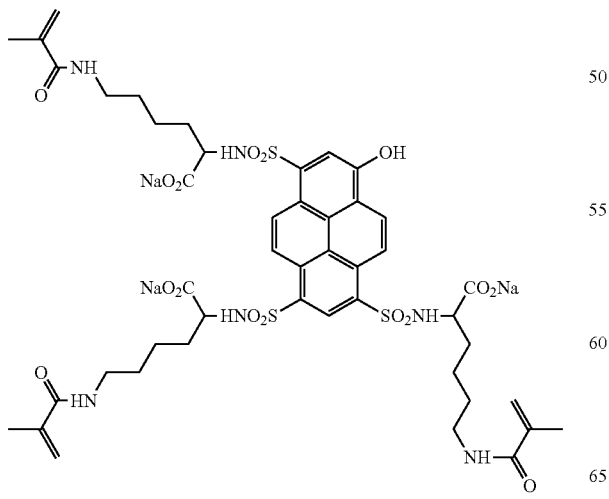

HPTS-LysMA

Other examples include soluble copolymers of 8-acetoxypyrene-1,3,6-N,N', N"-tris(methacrylamidopropylsulfonamide) with HEMA, PEGMA, or other hydrophilic comonomers. The phenolic substituent in the dye is protected during polymerization by a blocking group that can be removed by hydrolysis after completion of polymerization. Such suitable blocking groups, as for example, acetoxy, trifluoroacetoxy, and the like, are well known in the art.

Fluorescent dyes, including HPTS and its derivatives are known and many have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 11/296,898, 60/833,081, and 11/671,880; each of which is incorporated herein in its entirety by reference thereto.

The SNARF and SNAFL dyes from Molecular Probes may also be useful fluorophores in accordance with aspects of the present invention. The structures of SNARF-1 and SNAFL-1 are shown below.

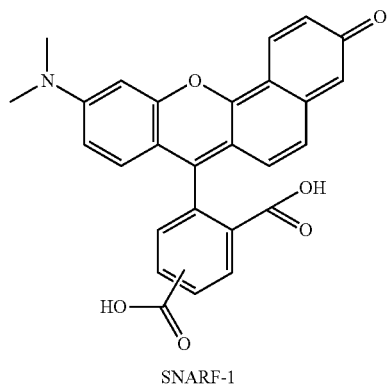

SNARF-1

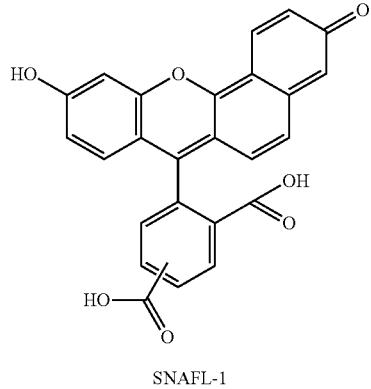

SNAFL-1

Additionally, a set of isomeric water-soluble fluorescent probes based on both the 6-aminoquinolinium and boronic acid moieties which show spectral shifts and intensity changes with pH, in a wavelength-ratiometric and colorimetric manner may be useful in accordance with some embodiments of the present invention (See e.g., Badugu, R. et al. 2005 Talanta 65 (3):762-768; and Badugu, R. et al. 2005 Bioorg. Med. Chem. 13 (1):113-119); incorporated herein in its entirety by reference.

Another example of a fluorescence dye is tetrakis(4-sulfophenyl)porphine (TSPP)—shown below. TSPP may not work optimally in blood, where the porphyrin ring may react with certain metal ions, like ferric, and become non-fluorescent. However, it may work better when included in the indicator system of a bench top analyte measurement apparatus.

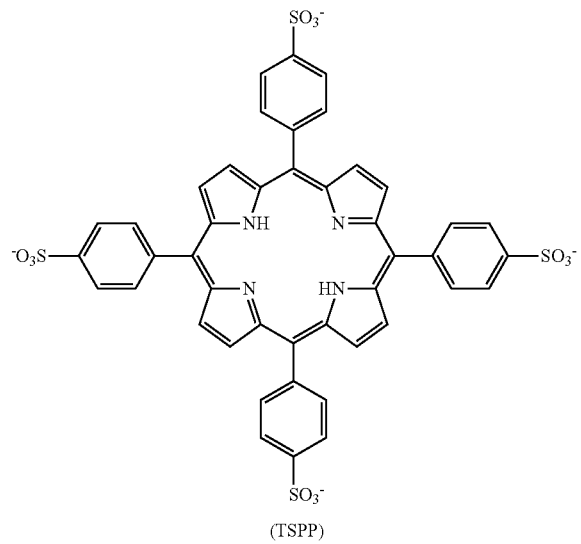

(TSPP)

Other examples of fluorescent indicators that may be useful for determination of glucose concentration are described in US 2005/0233465 and US 2005/0090014; each of which is incorporated herein by reference in its entirety.

Analyte Binding Moieties—Quenchers

In accordance with broad aspects of the present invention, the analyte binding moiety provides the at least dual functionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

In one example, the binding moiety that provides glucose recognition in the embodiments is an aromatic boronic acid. In some embodiments, the binding moiety may be a quencher comprising a boronic acid functionalized to either a pyridinium cation (or salt) as disclosed in U.S. Patent Application Publication No. 2008/0305009 or a polyviologen as disclosed in US. Patent Application Publication No. 2009/0081803; each of which is hereby incorporated herein in its entirety by reference thereto. In some embodiments, the boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N' bis-(benzyl) bipyridium dihalide (i.e., dichloride, bromide chloride), etc. Viologen also includes the substituted phenanthroline compounds. In some embodiments, the boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorophore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

In some embodiments, a binding moiety may comprise an analyte binding protein operably coupled to a fluorophore, such as the glucose binding proteins disclosed in U.S. Pat. Nos. 6,197,534, 6,227,627, 6,521,447, 6,855,556, 7,064,103, 7,316,909, 7,326,538, 7,345,160, and 7,496,392, U.S. Patent Application Publication Nos. 2003/0232383, 2005/0059097, 2005/0282225, 2009/0104714, 2008/0311675, 2008/0261255, 2007/0136825, 2007/0207498, and 2009/0048430, and PCT International Publication Nos. WO 2009/021052, WO 2009/036070, WO 2009/021026, WO 2009/021039, WO 2003/060464, and WO 2008/072338 which are hereby incorporated by reference herein in their entireties.

Bis-onium salts in the embodiments of this invention are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this invention. In one embodiment, the quencher may be one of the bis-onium salts derived from 3,3'-dipyridyl, 4,4'-dipyridyl and 4,7-phenanthroline.

In some embodiments, the viologen-boronic acid adduct may be a discrete compound having a molecular weight of about 400 Daltons or greater. In other embodiments, it may also be a pendant group or a chain unit of a water-soluble or water-dispersible polymer with a molecular weight greater than about 10,000 Daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the viologen-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix $M^2$, which can be represented by the structure $M^2$-$L^2$-Q. $L^2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

For the polymeric quencher precursors, multiple options are available for attaching the boronic acid moiety and a reactive group which may be a polymerizable group or a coupling group to two different nitrogens in the heteroaromatic centrally located group. These are:

a) a reactive group on a first aromatic moiety is attached to one nitrogen and a second aromatic group containing at least one —B(OH)2 group is attached to the second nitrogen;

b) one or more boronic acid groups are attached to a first aromatic moiety which is attached to one nitrogen and one boronic acid and a reactive group are attached to a second aromatic group which second aromatic group is attached to the second nitrogen;

c) one boronic acid group and a reactive group are attached to a first aromatic moiety which first aromatic group is attached to one nitrogen, and a boronic acid group and a reactive group are attached to a second aromatic moiety which is attached to the second nitrogen; and d) one boronic acid is attached to each nitrogen and a reactive group is attached to the heteroaromatic ring.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho- meta or para-positions.

In some embodiments, the boronic acid substituted viologen as a discrete compound useful for in vitro sensing may be represented by one of the following formulas:

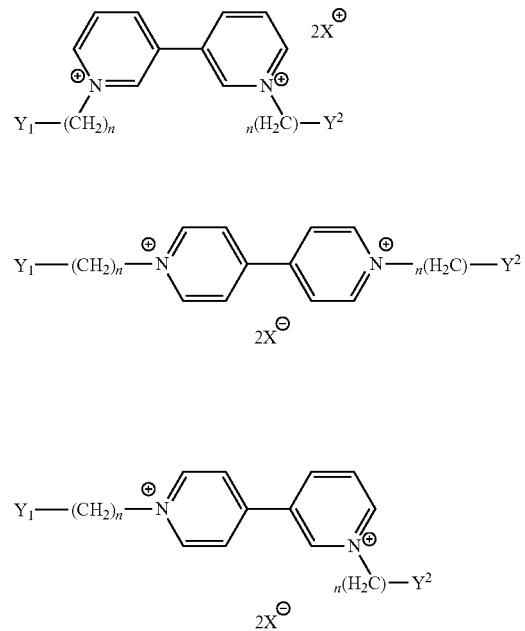

where n=1-3, X is halogen, and $Y^1$ and $Y^2$ are independently selected from phenyl boronic acid (o- m- or p-isomers) and naphthyl boronic acid. In other embodiments, the quencher may comprise a boronic acid group as a substituent on the heterocyclic ring of a viologen.

A specific example used with TSPP is m-BBV:

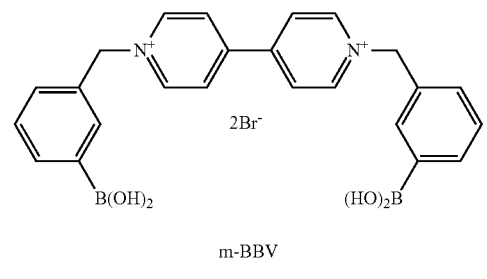 [SMILES: OB(O)c1cccc(C[n+]2ccc(-c3cc[n+](Cc4cccc(B(O)O)c4)cc3)cc2)c1]

m-BBV

The quencher precursors suitable for making sensors may be selected from the following:
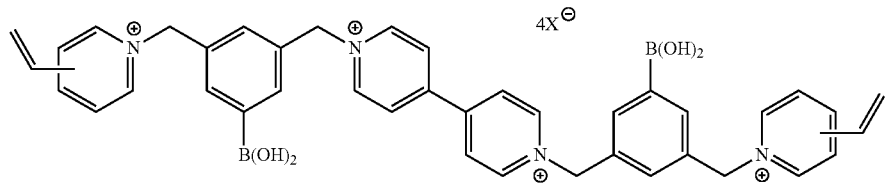
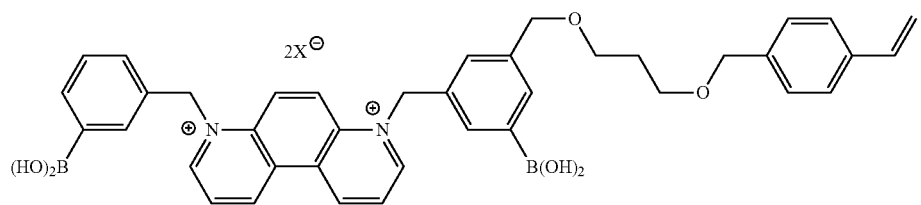
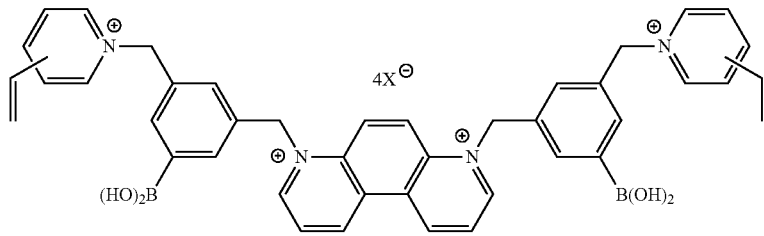
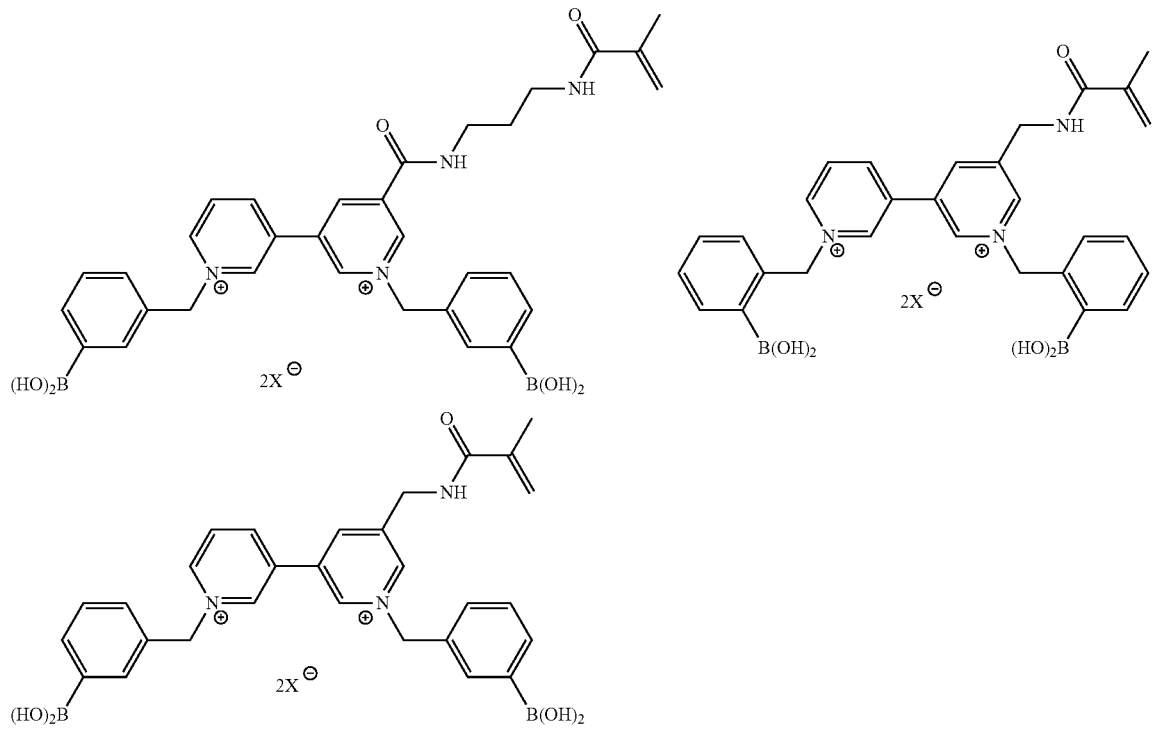

-continued
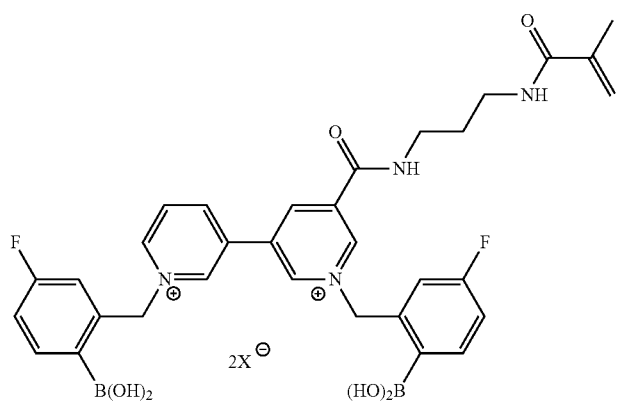
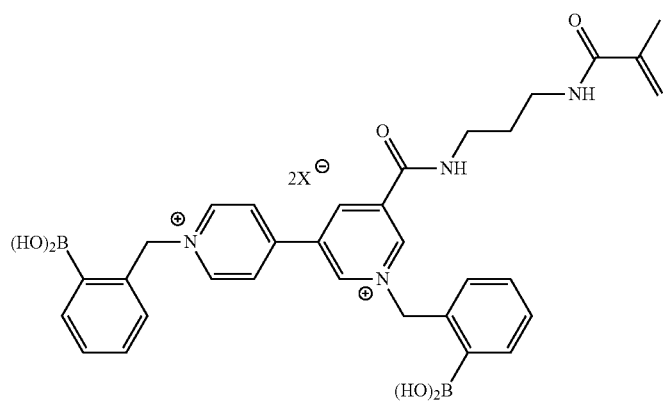
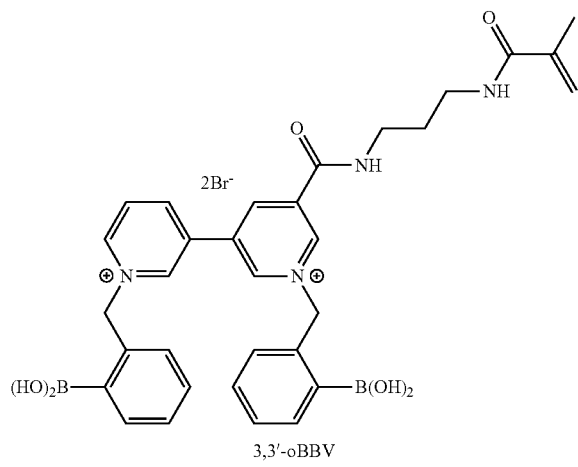
3,3'-oBBV

The quencher precursor 3,3'-oBBV may be used with HPTS-LysMA or HPTS-CysMA to make hydrogels in accordance with preferred aspects of the invention.

Preferred quenchers are prepared from precursors comprising viologens derived from 3,3'-dipyridyl substituted on the nitrogens with benzylboronic acid groups and at other positions on the dipyridyl rings with a polymerizable group or a coupling group. Representative viologens include:

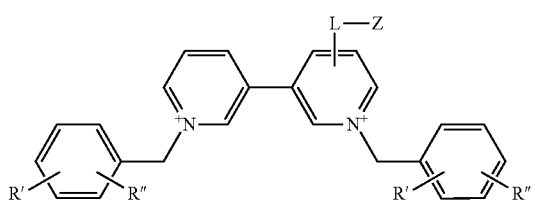

where L is L1 or L2 and is a linking group

Z is a reactive group; and

R' is —B(OH)$_2$ in the ortho- meta- or para-positions on the benzyl ring and R" is H—; or optionally R" is a coupling group as is defined herein or a substituent specifically used to modify the acidity of the boronic acid such as fluoro- or methoxy- L is a divalent moiety that covalently connects the sensing moiety to a reactive group that is used to bind the viologen to a polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like.

Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$.

Boronic acid substituted polyviologens are another class of preferred quenchers. The term polyviologen includes: a discrete compound comprised of two or more viologens covalently bonded together by a linking group, a polymer comprised of viologen repeat units in the chain, a polymer with viologen groups pendant to the chain, a dendrimer comprised of viologen units, preferably including viologen terminal groups, an oligomer comprised of viologen units, preferably including viologen endgroups, and combinations thereof. Polymers in which mono-viologen groups form a minor component are not included. The preferred quenchers are water soluble or dispersible polymers, or crosslinked, hydrophilic polymers or hydrogels sufficiently permeable to glucose to function as part of a sensor. Alternatively the polyviologen boronic acid may be directly bonded to an inert substrate.

A polyviologen quencher as a polymer comprised of viologen repeat units has the formula:

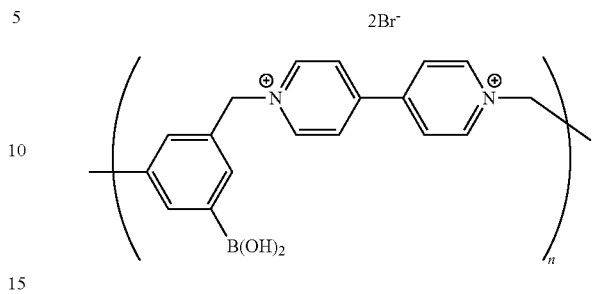

In another embodiment, the polyviologen boronic acid adducts are formed by covalently linking two or more viologen/boronic acid intermediates. The bridging group is typically a small divalent radical bonded to one nitrogen in each viologen, or to a carbon in the aromatic ring of each viologen, or one bond may be to a ring carbon in one viologen and to a nitrogen in the other. Two or more boronic acid groups are attached to the polyviologen. Optionally, the polyviologen boronic acid adduct is substituted with a polymerizable group or coupling group attached directly to the viologen or to the bridging group. Preferably the polyviologen moiety includes only one such group. Preferably, the bridging group is selected to enhance cooperative binding of the boronic acids to glucose.

The coupling moiety is a linking group as defined previously with the proviso that the linking group is optionally further substituted with a boronic acid, a polymerizable group, an additional coupling group, or is a segment in a polymer chain in which the viologen is a chain unit, a pendant group, or any combination thereof.

Immobilizing Medium

The indicator system comprising some embodiments of the measurement devices disclosed herein may include an immobilizing medium whose presence may prevent some of the fluorophores and/or some of the binding moieties from freely diffusing through the sample. For instance, in certain such embodiments, the immobilizing medium may limit the mobility of the sensing moieties (including one or more types of fluorophores and one or more types of binding moieties) such that they remain physically close enough to one another to react (quenching). Where in vivo sensing is desired, the immobilizing medium is preferably insoluble in an aqueous environment (e.g., intravascular), permeable to the target analytes, and impermeable to the sensing moieties. Where in vitro analyte measurement is desired, the immobilizing medium is preferably insoluble in the sample's solvent, permeable to the target analytes, and, again, impermeable to the sensing moieties. For example, a bench top glucose meter for measuring glucose activity in aqueous solution may comprise a water-insoluble organic polymer matrix that is permeable to the target analytes and impermeable to the sensing moieties. More specifically, the HPTS-triLysMA dye and 3,3'-oBBV quencher may be effectively immobilized within a DMAA (N,N-dimethylacrylamide) hydrogel matrix (described in detail below). Such an embodiment may be useful for devices configured for in vitro or in vivo sensing.

In some embodiments for use in vitro, and not involving a moving stream, the sensing moieties (including one or more types of fluorophores and one or more types of binding moieties) may be used as individual (discrete) components. For example, in some embodiments, the concentration of analyte in a liquid sample may be measured by adding and mixing into the sample the one or more types of fluorophores and binding moieties, exciting the one or more types of fluorophores with light of the appropriate wavelengths, and detecting the intensity of the fluorescence emitted by the fluorophores. Analyte concentration may then be calculated from the measured intensity. Afterwards, the sample has been contaminated with the one or more fluorophores and binding moieties and may need to be discarded. Of course, if the sample is taken from a larger solution, the amount of discarded solution may be insignificant.

In other embodiments for use in vitro, polymeric matrices may be used to trap the sensing moieties so that the sensing moieties do not permanently contaminate the sample, and so that the sensing moieties may be reused to determine analyte concentration in another sample. In certain such embodiments, the sensing moieties may be immobilized allowing their use to measure analytes in a moving stream.

For in vivo applications, some embodiments of the indicator system may be used in a moving stream of physiological fluid which contains one or more analytes, such as polyhydroxyl organic compounds, whose concentration is to be measured. Other embodiments for in vivo applications may be implanted in tissue such as muscle which contains the aforementioned analytes. Thus, for in vivo applications, it is often preferred that the sensing moieties do not escape from the sensor assembly. In some embodiments, this is accomplished by making the sensing moieties a part of an organic polymer sensing assembly. Soluble fluorophores and binding moieties may be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained. Note, however, that these embodiments will also find substantial utility in in vitro applications where it is desirable to immobilize or constrain the sensing moieties so that they do not freely mix with the sample in a way that they cannot be easily extracted. As stated above, such configurations reduce contamination of the sample and to some extent allow the fluorophores and binding moieties to be reused for multiple samples and analyte measurements.

Irrespective of whether analyte concentration is to be determined in vivo or in vitro, if glucose is the analyte of interest, it is often advantageous that the sensing moieties be immobilized. In some embodiments, the glucose sensing moieties may be immobilized in an insoluble polymer matrix, which is freely permeable to glucose. The polymer matrix may include of organic, inorganic or combinations of polymers thereof. For in vivo measurements, it may be advantageous for the matrix to be composed of biocompatible materials. Alternatively or additionally, the matrix may be coated with a second biocompatible polymer that is permeable to the analytes of interest. For in vitro measurements, the use of biocompatible materials may not be necessary or even advantageous.

In some embodiments where the indicator system includes a polymer matrix, the function of the polymer matrix is to hold together and immobilize the one or more fluorophores and one or more binding moieties while at the same time allowing contact and binding between the analyte and the one or more binding moieties. To achieve this effect, the matrix must be insoluble in the solution containing the analyte, but also be in close association with it through the establishment of a high surface area interface between matrix and analyte solution. For example, in some embodiments, an ultra-thin film or microporous support matrix may be used. In some embodiments, the matrix may be swellable in the analyte solution. For some embodiments used to measure analyte concentrations is aqueous solutions, a hydrogel matrix may be used. In some instances, the sensing polymers are bonded to a surface such as the surface of a light conduit, or impregnated in a microporous membrane. Preferably, the matrix does not substantially interfere with transport of the analyte to the binding sites so that equilibrium may be established between the two phases. Techniques for preparing ultra-thin films, microporous polymers, microporous sol-gels, and hydrogels are established in the art. Useful matrices are typically substantially permeable to the analyte being examined.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these embodiments, the one or more fluorophores and one or more binding moieties may be incorporated into the polymer by copolymerization using monomeric derivatives in combination with network-forming monomers. Alternatively, the one or more fluorophores and one or more binding moieties may be coupled to an already prepared matrix using a post polymerization reaction. In either case, the one or more fluorophores and one or more binding moieties can be viewed as units in the polymer chain, or as pendant groups attached to the chain.

The hydrogels useful in this invention are also monolithic polymers, such as a single network to which both sensing moieties are covalently bonded, or as multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium, chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the fluorophore is derived from an ethylenically unsaturated derivative of a dye molecule, such as 8-acetoxypyrene-1,3,6-N,N',N"-tris(methacrylamidopropyl-sulfonamide), the binding moiety is derived from an ethylenically unsaturated viologen such as 4-N-(benzyl-3-boronic acid)-4'-N'-(benzyl-4-ethenyl)-dipyridinium dihalide (m-SBBV) and the matrix is made from HEMA and PEGDMA. The concentration of fluorophore is chosen to optimize emission intensity. The ratio of binding moiety to fluorophore is adjusted to provide sufficient binding to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the fluorophore is incorporated in one component and the binding moiety in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the binding moiety is formed. The network is then swollen with a mixture of monomers including the fluorophore monomer and a second polymerization is carried out to obtain the IPN hydrogel.

The semi-IPN hydrogel is formed by dissolving a soluble polymer containing a fluorophore in a mixture of monomers including a binding moiety monomer and polymerizing the mixture. In some embodiments, the sensing components are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorophore and binding moieties while at the same time allowing contact with the analytes (e.g., polyhydroxyl compounds, $H^+$ and $OH^-$), and binding of the polyhydroxyl compounds to the boronic acid. Therefore, the matrix is insoluble in the medium and in close association with it by establishing a high surface area interface between matrix and analyte solution. The matrix also does not interfere with transport of the analyte to the binding sites so that equilibrium can be established between the two phases. In one embodiment, an ultra-thin film or microporous support matrix may be used. In another embodiment, the matrix that is swellable in the analyte solution (e.g. a hydrogel matrix) can be used for aqueous systems. In some embodiments, the sensing polymers are bonded to a surface such as the surface of a light conduit, or impregnated in a microporous membrane. Techniques for preparing ultra-thin films, microporous polymers, microporous sol-gels, and hydrogels have been established in the prior art.

In one preferred embodiment, the boronic acid substituted viologen may be covalently bonded to a fluorophore. The adduct may be a polymerizable compound or a unit in a polymer. One such adduct for example may be prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxypyrene-1,3,6-trisulfonyl chloride in a 1:1 mole ratio followed by reaction with excess PEG diamine to obtain a prepolymer mixture. An acid acceptor is included in both steps to scavenge the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups may be reacted with methacrylol chloride. After purification, the dye/viologen monomer may be copolymerized with HEMA and PEGDMA to obtain a hydrogel.

For example U.S. Pat. No. 5,114,676 (incorporated by reference herein in its entirety) provides a fluorescent indicator which may be covalently attached to a particle or to a microcrystalline cellulose fiber. A sensor utilizing the indicator may comprise an optically transparent substrate, a thermoplastic layer and a hydrogel. Part of the particle with the indicator attached thereto is imbedded in a thermoplastic layer that is coated on the substrate and mechanically adhered using heat and pressure. The majority of the particle/indicator is imbedded within a hydrogel layer that is applied over the thermoplastic layer. Such a sensor may be applied to the tip of an optical waveguide. Furthermore, with the recent availability of low cost UV LEDs, the dye can be measured with relatively inexpensive instrumentation that combines UV and blue LEDs and a photodiode module. In one embodiment of the present invention, the preferred sensing device comprises at least one light source, a detector, and a sensor comprising a fluorescent reporter dye system. In one embodiment, the fluorescent reporter dye system comprises a fluorescent dye operably coupled to an analyte-binding quencher. The dye may be covalently bound to the quencher or merely associated with the quencher. The dye and quencher are preferably operably coupled, which means that in operation, the quencher is in close enough proximity to the dye to interact with and modulate its fluorescence. In one embodiment, the dye and quencher may be constrained together within an analyte-permeable hydrogel or other polymeric matrix. When excited by light of appropriate wavelength, the fluorescent dye emits light (e.g., fluoresces). The intensity of the light is dependent on the extent of quenching which varies with the amount of analyte binding. In other embodiments, the fluorescent dye and the quencher may be covalently attached to hydrogel or other polymeric matrix, instead of to one another.

Protective Housing

In some embodiments, the sensor probe 200 of the measurement device includes a protective housing 500 which provides protection to the indicator system 307. In embodiments wherein the indicator system 307 comprises an immobilizing medium, the protective housing 500 may further protect the immobilizing medium. In certain such embodiments, the protective housing 500 may be appropriately sized for in vitro bench top laboratory use. In some embodiments, a protective housing 500 may provide a protective benefit to a sensor probe 200 that is designed for in vivo analyte measurement, and in some embodiments, more specifically, for a sensor probe 200 that is designed for intravascular analyte measurement. In certain such embodiments, the protective housing 500 may be constructed of physiologically compatible materials and may be sized for intravascular deployment. In embodiments wherein the sensor probe 200 includes a temperature sensing element, the temperature sensing element may be contained within the protective housing 500.

In some embodiments, such as the embodiments schematically depicted in FIGS. 7A and 7B, the protective housing 500 may be constructed of a hollow tube comprising a first material 501, and a second material 502 coating the first material 501. In some embodiments, the second material 502 may coat the first material 501 so as to form a continuous substantially impermeable outer wall of the hollow tube, except in a region where a portion of the second material 502 has been selectively removed in order to generate at least one opening in the outer wall, while retaining the first material 501 in that region. Three square cutouts 503 in the outer wall of the tube arranged in a line can be seen in FIGS. 7A and 7B, but cutouts of other shapes, positioned in other arrangements, are clearly feasible, depending on the embodiments. In some embodiments, such as the embodiment schematically illustrated in FIG. 7A, the first material 501 may form a tubular mesh 501A. In some embodiments, such as the embodiment schematically illustrated in FIG. 7B, the first material 501 may form a coil 501B. For each of the embodiments schematically illustrated in these figures, the first material 501 (whether in the form of a tubular mesh 501A or a coil 501B) is visible in the figures through the cutouts 503 in outer wall formed by the second material 502.

Examples of materials suitable for use as the coil or tubular mesh (i.e. the first material 501) include both metallic and non-metallic materials. Suitable metallic materials include stainless steel, gold, titanium and silver, and alloys such as nitinol, beryllium copper and MP-35-N alloys comprising cobalt, nickel, chromium, and molybdenum. In some embodiments, stainless steel is preferred. Suitable non-metallic materials include synthetic polymers such as polyamides, polyesters, polyurethanes, polyolefins, nylon and fluoropolymers, for example polytetrafluoroethylene (PTFE). The first material 501 must, however, be chosen so that it is possible to selectively remove a region of the second material 502 which coats the first material, without the first material itself being removed in that region.

As mentioned above, the first material 501 can be in the form of a coil 501B, see FIG. 7B, or a tubular mesh 501A, see FIG. 7A. When in the form of a coil 501B, the coil can be made from wires of the first material 501 which preferably have either a round or flat cross-section. When in the form of a tubular mesh 501A, the mesh structure advantageously comprises a number of filaments. The term "filament" is used to refer to any elongated strand irrespective of its cross-sectional configuration and structure. For example, the filaments may be round or flat in cross-section. In one embodiment, the mesh can comprise a number of helically wound filaments, for example comprising a first group of filaments wound in an anticlockwise direction and a second group of filaments wound in an opposite, clockwise direction. The tubular mesh 501A of FIG. 7A displays this configuration. Suitable mesh structures are described in International publication No. WO/2004/054438 which is incorporated by reference herein in its entirety.

In some embodiments wherein the first material 501 is in the form of a tubular mesh 501A, the density of filament crossovers may be varied in order to control the properties of the resulting hollow tube. For example, a high density mesh may engender the hollow tube with greater strength while a low density mesh provide the hollow tube with greater flexibility. Variation in the tightness of a coil can provide a similar effect.

Variation in mesh density and/or coil tightness may also vary the porosity of the mesh. This variation may be significant at the location of the opening in the outer wall formed by the second material since the porosity of the mesh in this region will control the speed of diffusion of the analyte into the sensor. Porosity is also important for embodiments employing an immobilizing medium because, in certain such embodiments, the mesh may need to be sufficiently dense (or the coil winding sufficiently tight) to prevent seepage or leakage of the immobilizing medium out of the sensor's protective housing. Thus, in some embodiments, coil tightness and/or mesh density must be chosen simultaneously to give the protective housing sufficient strength and flexibility to protect against impacts and abrasions, to allow sufficient diffusion of analytes into the protective housing, and to contain the immobilizing medium so that it does not leak out of the protective housing. Obviously, in embodiments lacking an immobilizing medium, leakage of an immobilizing medium out of the protective housing need not be considered.

Suitable materials for use as the second material generally include polymeric materials. Examples include polyesters, polyolefins such as polyethylene (PE), e.g. low density polyethylene (LDPE), fluoropolymers such as fluorinated ethylene propylene (FEP), polytetrafluoroethylene (PTFE) and perfluoroalkoxy polymer (PFA), polyvinylchloride (PVC), polyamides such as polyether block amide (PEBA), Pebax®, nylon and polyurethane. Polyesters and polyolefins are preferred due to their suitability for extrusion over the coil or tubular mesh. The selective removal of a portion of a polyester or polyolefin coating, e.g. by laser ablation, is also straightforward. Polyolefins are particularly preferred due to the ease of laser ablating these materials.

In order to form a continuous substantially impermeable tube prior to selective removal of a portion of the second material, the second material is first used to coat the coil or tubular mesh formed by the first material. The second material can either coat the outer surfaces of the first material, and in effect form a continuous substantially impermeable tube around the coil or tubular mesh formed by the first material, or the second material can entirely encapsulate the first material, effectively forming a tube of the second material in which is embedded the coil or tubular mesh formed by the first material. In one embodiment the second material can be applied to the first material by dip coating the coil or tubular mesh formed by the first material. In this embodiment, the second material may be a polyamide, which results in a very stiff tube. In another embodiment a tube of the second material can be provided, around which is formed the coil or tubular mesh of the first material. A further layer of the second material is then applied over the first material, resulting in the first material being sandwiched between two layers of the second material.

As mentioned above, it is necessary that it be possible to selectively remove a region of the second material while retaining the first material in that region. Accordingly, it is a requirement that the second material is different from the first material. In this context, "different from" means that the first and second materials have some difference in physical properties such that it is possible to selectively remove a region of the second material. This difference may be achieved by using an entirely different material, or by using the same material but using different forms which have different physical properties. For example, in one embodiment the first material is metallic and the second material is polymeric.

In addition to the first and second materials, it is possible to include further materials. For example, for some applications it may be useful to include a radio opaque additive to enable the sensor incorporating the tube to be visible in vivo. For example, radio opaque additives such as barium sulfate, bismuth subcarbonate, bismuth trioxide and tungsten can be added. Where present, these are preferably doped within the second material.

When constructing the protective housings described above, a portion of the second material is selectively removed in order to generate at least one opening in a region of the outer wall of the protective housing, while retaining the first material in that region. As the first material is present in the form of a coil or a tubular mesh, the first material does not form a completely closed tube. Accordingly, when the second material is removed in said region, this effectively forms a break in the continuous substantially impermeable wall of the tube. Where the second material simply coats the first material, it is necessary simply to remove the coating provided by this second material in the region where the opening is to be formed. Where the second material effectively encapsulates the first material, it is necessary to remove all of the second material which surrounds and encapsulates the first material in the region of the protective housing where the opening is to be formed.

Preferably the indicator system 307 used to generate a signal indicative of the concentration of the analyte of interest is located adjacent to the opening 503 formed by selective removal of the second material. This allows the indicator system to measure analyte concentration near the region of the opening in the wall of the tube. Presumably, the environment of the fluid in this region is substantially similar to the environment of the fluid further away from the sensor probe's protective housing 500, and therefore the analyte concentration determined in this region will likely accurately represent the analyte concentration elsewhere in the fluid. For example, where the measurement device is an intravascular glucose sensor, the sensor probe 200 and protective housing 500 may be inserted into a blood vessel, for example, and glucose in the blood will preferably migrate through the opening in the second material, and into the hollow tube, where its concentration can be determined by the indicator system in conjunction with the other components of the measurement device. Where the measurement device is a bench top glucose meter, the sensor probe 200 and protective housing 500 may be dipped into a solution contained in a beaker or test tube, for example, such that the opening in the second material is submerged. The solution will then pass through the opening in the second material, into the hollow tube, and the glucose concentration of the solution may be determined by the indicator system in conjunction with the other components of the glucose sensor.

In some embodiments, the size of the opening in the second material will generally be between 1 and 400 mm$^2$, for example between 25 and 225 mm$^2$. The size of the opening is preferably not too small or the solution into which the sensor is introduced will not be able to pass through the opening or will pass through in insufficient quantities for an accurate measurement to be made. Yet, the opening is preferably not too large or else the immobilizing medium constraining the free diffusion of the sensing moieties may be able to seep out. In some embodiments, it is advantageous that the opening be large enough to allow positioning of the indicator system such that it is adjacent to the opening.

In some embodiments, the second material forming the outer wall of the protective housing 500 possesses only a single opening 503 allowing passing of the analyte. In other embodiments, a plurality of openings 503 may be generated in the outer wall of the protective housing 500—i.e. more than one region of the second material has been removed. For example, the protective housings 500 of the sensor probes 200 displayed in FIGS. 7A and 7B each possess three regions where the second material 502 has been removed, exposing the first material 501A, 501B, and creating three openings 503 for the passage of analytes. Generally speaking, configurations of multiple openings in the protective housing allow for indicator systems, or portions of indicator systems, to be located at a number of points along the length of the protective housing, and for multiple measurements to be taken. Thus, it is possible for a number of indicator systems to be located within a single protective housing, each measuring the analyte in a portion of the fluid containing the analyte which enters the protective housing through a different opening in the housing. It is also possible that a single indicator system may comprise multiple sub-systems, each of which is spatially separated within the protective housing, and each of which measures the analyte in a portion of the fluid containing the analyte which enters the protective housing through a different opening in the housing.

Many embodiments of the protective housings 500 disclosed above may, in many instances, provide a robust and durable enclosure for protecting the sensitive components of the sensor probe 200. Such protective housings may protect an in vitro sensor probe from impacts and abrasions occurring during bench top laboratory use. Alternatively, such protective housings may provide the durability and maneuverability necessary for intravascular use. However, it should be understood that many types of protective housings may be suitable for protecting the indicator systems disclosed herein, beyond those particular types of protective housings that have been disclosed above.

Methods of Estimating Analyte Concentration Incorporating Temperature Correction Some embodiments of the measurement devices disclosed herein generate a signal indicative of analyte concentration which exhibits a temperature dependence. For example, if two solutions of precisely the same analyte concentration are measured at two different temperatures with the same measurement device, in some embodiments, the measurement device may generate differing signals indicative of the two analyte concentrations. Thus, the accuracy of determining a solution's true analyte concentration based on such as signal may be improved by taking the temperature of the solution into account.

It has been discovered that for some embodiments of the measurement devices disclosed herein, and in particular, for glucose measurement devices employing a quencher binding moiety operably coupled to a fluorophore, the temperature dependence of the fluorescent signal approximately follows a modified version of the classic Michaelis-Menten equation from enzyme kinetics:

$$[Glu] = \frac{c_T * [G_i - a_T]}{a_T + b_T - G_i} \quad \text{(Equation 1)}$$

where
- [Glu] is the estimated glucose concentration,
- $a_T$ is the first Michaelis-Menten parameter "a", at a temperature T,
- $b_T$ is the second Michaelis-Menten parameter "b", at the same temperature T,
- $c_T$ is the third Michaelis-Menten parameter "c", at the same temperature T, and
- $G_i$ is the fluorescent signal (i=1,2), either referenced or unreferenced, where $G_1$ is the fluorescence emission at 550 nm when the fluorophore is excited at 470 nm (which is the absorption maximum of the fluorophore's base-form), and $G_2$ is the fluorescence emission at 550 nm when the fluorophore is excited at 420 nm (which is the absorption maximum of the fluorophore's acid-form). Note, however, that other combinations of excitation and emission wavelengths are also feasible for use in Equation 1. In the Examples below, $G_2$ has been used, unless indicated otherwise.

In itself, this is an interesting and surprising result. Various embodiments of the measurement devices disclosed herein employ a quencher-fluorophore indicator system which measures analyte concentration through the establishment of an equilibrium between the analyte of interest, the binding moiety (e.g. quencher), and the fluorophore. In such a system, analyte concentration is not measured by enzymatic consumption or conversion of the analyte. In contrast, the classic Michaelis-Menten equation specifically describes enzyme kinetics, a non-equilibrium phenomena involving the consumption/conversion of the enzyme's substrate by the enzyme. Therefore, it is not to be expected, indeed it is surprising, that an equation closely related to the classic Michaelis-Menten equation would effectively describe the temperature dependence of these types of quencher-fluorophore-based measurement devices and analyte sensing elements (or other measurement devices and analyte sensing elements functioning through analogous equilibrium mechanisms). In any event, knowledge that these devices (and similar devices) exhibit a temperature dependence which follows a modified Michaelis-Menten equation allows the use of temperature correction methods and algorithms to improve the accuracy of analyte concentration measurements. Such methods and algorithms are disclosed herein, along with measurement devices which implement such methods and algorithms.

Accordingly, some embodiment methods of estimating an analyte concentration include generating a signal indicative of analyte concentration and a signal indicative of temperature. Since, in some embodiments, the signal indicative of analyte concentration exhibits the temperature dependence just described, in some embodiments, the signal indicative of temperature may be used to adjust the signal indicative of analyte concentration to correct for temperature dependence. Thus, in certain such embodiments, the methods further include transforming the signal indicative of the analyte concentration utilizing an equation of the form of a modified Michaelis-Menten equation, such as Equation 1 above, depending on Michaelis-Menten parameters, such as the parameters "a", "b", and "c", as described above with reference to Equation 1.

The temperature dependence of Equation 1 is exhibited through the Michaelis-Menten parameters $a_T$, $b_T$, and $c_T$, as indicated by the subscript "T" labeling these parameters. In some embodiments, the temperature dependence may need to be determined through a temperature calibration. Thus, in certain embodiment methods, the values of one or more of the Michaelis-Menten parameters may be set based on data which includes temperature calibration data and the signal indicative of a temperature.

For example, in some embodiment methods, the temperature calibration data may be generated by a temperature calibration method. The temperature calibration method may include selecting a first test analyte sensing element, and creating and/or providing a set of at least three solutions of differing known analyte concentrations. In certain such embodiments, a first temperature is selected (T1), three solutions of the set of at least three solutions are heated and/or cooled to a temperature substantially similar to the selected first temperature, and a first set of at least three signals is generated using the first test analyte sensing element, each signal indicative of the concentration of analyte in a different one of the three solutions at the first temperature. Measurements are then made at a second temperature. Thus, in certain embodiments, a second temperature is selected (T2), three solutions of the set of at least three solutions (each of the three may be the same or different than a solution chosen for the first temperature) are heated and/or cooled to a temperature substantially similar to the selected second temperature, and a second set of at least three signals is generated using the first test analyte sensing element, each signal indicative of the concentration of analyte in a different one of the three solutions at the second temperature. Of course, more than three solutions may be used in either of these steps. And more than two temperatures may also be employed. Generally, the more solutions of differing concentration and the greater number of different temperatures that are employed, the greater the accuracy of the resulting calibration data.

Once the solutions having known analyte concentrations have been measured, and the first and second sets of at least three signals have been generated, in some embodiments, the sets of signals are used to determine (usually approximately) the relationship between one or more of the Michaelis-Menten parameters and temperature. For example, in some embodiments, the temperature calibration method may further include computing values of each of a first, second, and third Michaelis-Menten parameter at the first temperature ($a_{T1}$, $b_{T1}$, and $c_{T1}$) by an algorithm comprising fitting a modified Michaelis-Menten equation to a first fit dataset comprising the first set of at least three signals. In certain such embodiments, the temperature calibration method may further include computing values of each of a first, second, and third Michaelis-Menten parameter at the second temperature ($a_{T2}$, $b_{T2}$, and $c_{T2}$) by an algorithm comprising fitting a modified Michaelis-Menten equation to a second fit dataset comprising the second set of at least three signals. Thus, in methods such as these, each of the three Michaelis-Menten parameters has been determined at least two temperatures, providing data which may be used to create a model of the temperature dependence of each of the three Michaelis-Menten parameters.

To model the temperature dependence of the Michaelis-Menten parameters, in some embodiments, the temperature calibration method may further include selecting an equation relating the first Michaelis-Menten parameter ($a_T$) to temperature, the equation depending on a first set of temperature calibration parameters; and setting a value for each calibration parameter of the first set of calibration parameters based on the value of the first Michaelis-Menten parameter at the first temperature ($a_{T1}$) and the value of the first Michaelis-Menten parameter at the second temperature ($a_{T2}$). In some embodiments, similar steps are performed with respect to the second and third Michaelis-Menten parameters ($b_T$ and $c_T$). Thus, for example, the temperature calibration method may further include selecting an equation relating the second Michaelis-Menten parameter ($b_T$) to temperature, the equation depending on a second set of temperature calibration parameters; and setting a value for each calibration parameter of the second set of calibration parameters based on the value of the second Michaelis-Menten parameter at the first temperature ($b_{T1}$) and the value of the second Michaelis-Menten parameter at the second temperature ($b_{T2}$). Similarly, in some embodiments, the temperature calibration method may further include selecting an equation relating the third Michaelis-Menten parameter ($c_T$) to temperature, the equation depending on a third set of temperature calibration parameters; and setting a value for each calibration parameter of the third set of calibration parameters based on the value of the third Michaelis-Menten parameter at the first temperature ($c_{T1}$) and the value of the third Michaelis-Menten parameter at the second temperature ($c_{T2}$).

Furthermore, in some embodiments, equations linear in temperature may be selected to relate the first, second, and third Michaelis-Menten parameters to temperature. For instance, in some embodiments, the first, second, and third Michaelis-Menten parameters may be written as $$a_T = a_{37} * \tau_{a_T}(T),$$

$$b_T = b_{37} * \tau_{b_T}(T), \text{ and}$$

$$c_T = c_{37} * \tau_{c_T}(T) \quad \text{(Equation 2)}$$

where $\tau_{a_T}(T)$, $\tau_{b_T}(T)$, and $\tau_{c_T}(T)$ are "temperature correction factors" which approximately account for the temperature dependence of $a_T$, $b_T$, and $c_T$. When the relationship between Michaelis-Menten parameter and temperature is written as such, each Michaelis-Menten parameter $a_T$, $b_T$, and $c_T$, is determined by multiplying the 37° C. Michaelis-Menten parameter $a_{37}$, $b_{37}$, and $c_{37}$, by its corresponding "temperature correction factor," $\tau_{a_T}(T)$, $\tau_{b_T}(T)$, or $\tau_{c_T}(T)$ respectively. The 37° C. Michaelis-Menten parameters may be determined by fitting a modified Michaelis-Menten equation to a set of signals indicative of the analyte concentration of a plurality of solutions of differing analyte concentrations held at a temperature of 37° C., as described above with respect to, for example, T1 and T2. Alternatively, the parameters $a_{37}$, $b_{37}$, and $c_{37}$ may be supplied by a factory calibration as described in provisional U.S. patent application No. 61/184,747, "Algorithms for Calibrating an Analyte Sensor," filed Jun. 5, 2009, which is hereby incorporated herein by reference in its entirety. As yet another alternative, $a_{37}$, $b_{37}$, and $c_{37}$ may be determine via a one-point in vivo calibration as also disclosed in the same application.

To determine the "temperature correction factors," $\tau_{a_T}(T)$, $\tau_{b_T}(T)$, and $\tau_{c_T}(T)$, some embodiment methods may employ a linear approximation. For instance, the temperature correction factors may be written as $$\tau_{a_T}(T) = m_{a_T} * T + \beta_{a_T},$$

$$\tau_{b_T}(T) = m_{b_T} * T + \beta_{b_T}, \text{ and}$$

$$\tau_{c_T}(T) = m_{c_T} * T + \beta_{c_T} \quad \text{(Equation 3)}$$

where the slopes, $m_{a_T}$, $m_{b_T}$, $m_{c_T}$, and intercepts, $\beta_{a_T}$, $\beta_{b_T}$, $\beta_{c_T}$, are collectively referred to as "temperature calibration coefficients" ("TempCos").

In some embodiments, a temperature calibration method used to determine values of these TempCos may require that values of the Michaelis-Menten parameters be determined at a second temperature (T2), different than 37° C. Values of the parameters at the second temperature ($a_{T2}$, $b_{T2}$, and $c_{T2}$) may be determined by fitting a modified Michaelis-Menten equation to a set of signals indicative of the analyte concentration of a plurality of solutions of differing analyte concentrations held at the second temperature, as described above with respect to, for example, T1 and T2. Once this is done, the temperature calibration coefficients $m_a$ and $b_a$ may be determined by normalizing to $a_{37}$ both $a_{T2}$ and $a_{37}$, yielding $a_{T2}/a_{37}$ and 1, and fitting a line to the normalized values versus the two temperatures, T2 and 37° C. The fit may be determined using linear least squares or any other method of fitting a line to a set of points. The temperature calibration coefficient $m_{a_T}$ is set equal to the slope of the resulting line and the temperature calibration coefficient $\beta_{a_T}$ is set equal to the intercept. The other temperature calibration coefficients, $m_{b_T}$ and $\beta_{b_T}$, may be determined similarly from values of $b_{T2}$ and $b_{37}$, and $m_{c_T}$ and $\beta_{c_T}$ be determined from values of $c_{T2}$ and $c_{37}$. Once the calibration is complete, a temperature corrected estimated glucose concentration ([Glu]) may be computed from a fluorescent signal ($G_i$) measured at temperature (T), by using the TempCos ($m_{a_T}$, $\beta_{a_T}$, $m_{b_T}$, $\beta_{b_T}$, $m_{c_T}$, and $\beta_{c_T}$), the 37° C. Michaelis-Menten parameters 37° C. ($a_{37}$, $b_{37}$, and $c_{37}$), and the temperature (T) in Equations 2 and 3 to compute $a_T$, $b_T$, and $c_T$, and then plugging $a_T$, $b_T$, $c_T$ and the measured fluorescent signal ($G_i$) into Equation 1.

Thus, in some embodiments the first, second, and third sets of temperature calibration parameters may include a slope and an intercept relating temperature to the value of either the first, second, or third Michaelis-Menten parameter. However, equations of other forms may be selected to relate the first, second, or third Michaelis-Menten equation to temperature. In some embodiments, a quadratic or higher-order polynomial in temperature may be suitable and/or desirable.

When measurement devices are mass produced, it may not be feasible or practical to individually calibrate each measurement device—i.e. use each individual measurement device to generate individual calibration data. It may be more cost effective to select one or more test devices from a batch of mass produced devices, generate calibration data using the one or more test devices, and provide that calibration data to each individual devices produced in the batch. In some embodiments, variability between measurement devices from the same production batch may be, to a large extent, attributable to a particular part of the measurement device. In particular, variability between devices may be attributable to the part of the measurement device which generates a signal indicative of analyte concentration—e.g. the analyte sensing element—and/or the part of the measurement device that generates a signal indicative of temperature—e.g. the temperature sensing element. In these circumstances, as well as others, it may be advantageous to use a calibration method employing multiple test measurement devices, and/or multiple test sensing elements, because calibration over multiple test devices and/or sensing elements may yield more accurate calibration data than calibration methods which only utilize a single test device and/or sensing element. Accordingly, in some embodiments, the calibration method may further include selecting a second test analyte sensing element; generating a third set of at least three signals using the second test analyte sensing element, each signal indicative of the concentration of analyte in a different solution of known analyte concentration at the first temperature (T1); and generating a fourth set of at least three signals using the second test analyte sensing element, each signal indicative of the concentration of analyte in a different solution of known analyte concentration at the second temperature (T2). Obviously, calibration methods may similarly employ more than two test devices, or more particularly, for instance, more than two test analyte sensing elements.

In a manner similar to methods utilizing a single test analyte sensing element, after the solutions having known analyte concentrations have been measured and the first, second, third, and fourth sets of at least three signals have been generated, in some embodiments, the sets of signals are used to determine (usually approximately) the relationship between one or more of the Michaelis-Menten parameters and temperature. For example, in some embodiments, the temperature calibration method may further include (1) computing values of each of a first, second, and third Michaelis-Menten parameter at the first temperature ($a_{T1}$, $b_{T1}$, and $c_{T7}$) by an algorithm comprising fitting a modified Michaelis-Menten equation to a first fit dataset comprising both the first set of at least three signals (which was generated with the first test analyte sensing element at T1) and the third set of at least three signals (which was generated with the second test analyte sensing element at T1); and (2) computing values of each of a first, second, and third Michaelis-Menten parameter at the second temperature ($a_{T2}$, $b_{T2}$, and $c_{T2}$) by an algorithm comprising fitting a modified Michaelis-Menten equation to a second fit dataset comprising both the second set of at least three signals (which was generated with the first test analyte sensing element at T2) and fourth set of at least three signals (which was generated with the second test analyte sensing element at T2). Essentially, in these types of methods, the signals generated with the second test analyte sensing element are used in a combined fit with the signals generated with the first test analyte sensing element, which results in values for each of the first, second, and third Michaelis-Menten parameters which take both test analyte sensing elements into account. Alternatively, in some embodiments, a temperature calibration method may take both test analyte sensing elements into account by fitting the signals generated from each test analyte sensing element separately, and then averaging the results to obtain better estimates of the Michaelis-Menten parameters. Thus, in some embodiments, the step of computing values of each of a first, second, and third Michaelis-Menten parameter at the first temperature ($a_{T1}$, $b_{T1}$, and $c_{T1}$) by an algorithm may further include fitting a modified Michaelis-Menten equation to a third fit dataset comprising the third set of at least three signals, and averaging the results of fitting the third fit dataset with the results of fitting the first fit dataset. In addition, the step of computing values of each of a first, second, and third Michaelis-Menten parameter at the second temperature ($a_{T2}$, $b_{T2}$, and $c_{T2}$) by an algorithm may further include fitting a modified Michaelis-Menten equation to a fourth fit dataset comprising the fourth set of at least three signals, and averaging the results of fitting the fourth fit dataset with the results of fitting the second fit dataset.

Other methods for estimating analyte concentration which incorporate temperature correction features and temperature calibration steps are also disclosed herein. In some embodiments, these methods are similar to those already described above and incorporate similar features, however, additional features may also be disclosed and, in some embodiments, the disclosed methods may be more general and described in more general terms. Since there are many ways to feasibly implement the discoveries disclosed herein for use in estimating analyte concentration, the following additional methods are described in order to illustrate the breadth of implementations that are possible.

In some embodiments, for instance, a method of estimating an analyte concentration from a signal indicative of the analyte concentration may include transforming the signal using an equation of the form of a modified Michaelis-Menten equation wherein the values of one or more Michaelis-Menten parameters have been adjusted for temperature.

In some embodiments, for instance, a method of estimating an analyte concentration may include generating a signal indicative of the analyte concentration and generating a signal indicative of a temperature, and transforming the signal indicative of the analyte concentration utilizing an equation of the form of a modified Michaelis-Menten equation wherein at least one of the Michaelis-Menten parameters has been substituted with a calibration equation functionally depending on a set of one or more temperature calibration parameters and the signal indicative of temperature. One could refer to such an equation as a "substituted" modified Michaelis-Menten equation since the Michaelis-Menten parameters have been explicitly substituted with equations depending on one or more other variables—temperature and the temperature calibration parameters. However, although such a "substituted" equation exhibits a more complicated analytic form, it nevertheless will still express the basic functional relationships of the modified Michaelis-Menten equation.

In some embodiments, the step of transforming the signal indicative of analyte concentration may utilize a "substituted" modified Michaelis-Menten equation in which each of the first, second, and third Michaelis-Menten parameters have been substituted with first, second, and third calibration equations (respectively), each of the equations depending on sets of first, second, and third temperature calibration parameters (respectively), and each also depending on the signal indicative of temperature. In certain embodiments, at least one of the first, second, and third calibration equations is a polynomial in the signal indicative of temperature. In certain such embodiments, each of the first, second, and third calibration equations is a polynomial in the signal indicative of temperature. In certain embodiments, at least one of the first, second, and third calibration equations is a linear equation in the signal indicative of temperature. In certain such embodiments, each of the first, second, and third calibration equations is a linear equation in the signal indicative of temperature. Thus, for example, if each Michaelis-Menten parameter of Equation 1 above is assumed to exhibit a linear relationship with temperature, then the "substituted" modified Michaelis-Menten equation might appear as $$[Glu] = \frac{(\chi_{c_T,1} \cdot T + \chi_{c_T,0}) * [G_i - (\chi_{a_T,1} \cdot T + \chi_{a_T,0})]}{(\chi_{a_T,1} \cdot T + \chi_{a_T,0}) + (\chi_{b_T,1} \cdot T + \chi_{b_T,0}) - G_i} \quad \text{(Equation 4)}$$

and, similarly, if each Michaelis-Menten parameter is assumed to exhibit a quadratic relationship with temperature then the "substituted" modified Michaelis-Menten equation might appear as $$[Glu] = \frac{(\chi_{c_T,2} \cdot T^2 + \chi_{c_T,1} \cdot T + \chi_{c_T,0}) * [G_i - (\chi_{a_T,2} \cdot T^2 + \chi_{a_T,1} \cdot T + \chi_{a_T,0})]}{(\chi_{a_T,2} \cdot T^2 + \chi_{a_T,1} \cdot T + \chi_{a_T,0}) + (\chi_{b_T,2} \cdot T^2 + \chi_{b_T,1} \cdot T + \chi_{b_T,0}) - G_i} \quad \text{(Equation 5)}$$

where:

[Glu] is the estimated glucose concentration, $\chi_{a_T,2}$, $\chi_{a_T,1}$, and $\chi_{a_T,0}$ are polynomial coefficients parameterizing $a_T$'s dependence on the temperature T, $\chi_{b_T,2}$, $\chi_{b_T,1}$, and $\chi_{b_T,0}$ are polynomial coefficients parameterizing $b_T$'s dependence on the temperature T, $\chi_{c_T,2}$, $\chi_{c_T,1}$, and $\chi_{c_T,0}$ are polynomial coefficients parameterizing $c_T$'s dependence on the temperature T, and $G_i$ is the fluorescent signal (i=1,2), either referenced or unreferenced, where $G_1$ is the fluorescence emission at 550 nm when the fluorophore is excited at 470 nm (which is the absorption maximum of the fluorophore's base-form), and $G_2$ is the fluorescence emission at 550 nm when the fluorophore is excited at 420 nm (which is the absorption maximum of the fluorophore's acid-form). Note, however, that other combinations of excitation and emission wavelengths are also feasible for use in Equations 4 and 5.

As stated above, although, the "substituted" equations (Equations 4 and 5) exhibit a more complicated analytic form, they nevertheless still exhibit the basic functional relationships of the modified Michaelis-Menten equation (Equation 1). In other embodiments, the calibration equations substituted into the modified Michaelis-Menten equation may have a functional form other than a polynomial in temperature.

Thus, as described above, the calibration equations substituted into the modified Michaelis-Menten equation for the Michaelis-Menten parameters may take a variety of functional forms and each may have varying numbers of temperature calibration parameters. Obviously, more complicated equations may have a greater numbers of temperature calibration parameters. In any event, depending on the embodiment, various temperature calibration methods may be used to determine the values of the first, second, and third sets of the one or more temperature calibration parameters. In certain such embodiments, each set of temperature calibration parameters may be determined by fitting the "substituted" modified Michaelis-Menten equation to a plurality of signals, the plurality of signals indicative of analyte concentration in a plurality of solutions at a plurality of temperatures. Once values of the various temperature calibration parameters are determined, temperature corrected estimates of analyte concentrations may be generated from signals indicative of analyte concentration and temperature.

EXAMPLE 1

This example concerns the temperature calibration of an equilibrium fluorescence glucose sensor—referred to herein as a GluCath sensor—employing an HPTS-Cys-MA dye operably coupled to a 3,3'-oBBV quencher. The dye and quencher are immobilized within a hydrogel disposed along the distal region of an optical fiber, while the proximal end of the optical fiber is coupled to a light source. The temperature dependence of this sensor's fluorescence response to glucose was assumed to be described by the modified Michaelis-Menten equation of Equation 1 as described above. The Michaelis-Menten parameters were assumed to bear a linear relationship to temperature as set forth in Equations 2 and 3 above. Using this model of the glucose sensor's temperature dependence, the TempCos ($m_{a_T}$, $\beta_{a_T}$, $m_{b_T}$, $\beta_{b_T}$, $m_{c_T}$, and $\beta_{c_T}$) were determined by the methodology described above in reference to Equations 2 and 3. Specifically, the effect of temperature on the fluorescent signal was determined experimentally by measuring the signal at four temperatures (15° C., 25° C., 37° C., and 45° C.) and four glucose concentrations (50 mg/dL, 100 mg/dL, 200 mg/dL, and 400 mg/dL). At each temperature and glucose level the stable signal, $G_2$, was recorded.

Figure 8:
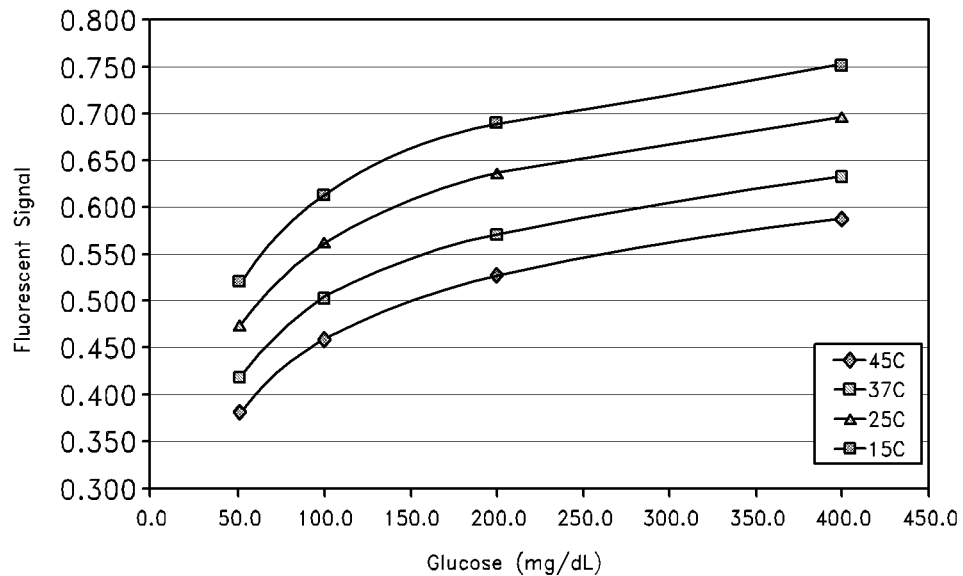
FIG. 8 displays four plots of fluorescent signal versus glucose concentration at four different temperatures generated by one embodiment of a measurement device disclosed herein.
Figure 9:
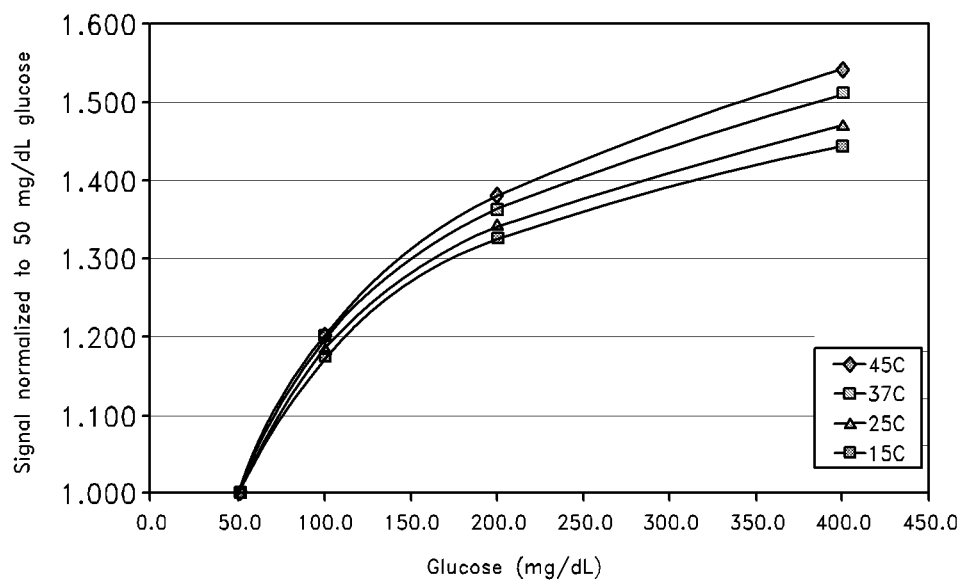
FIG. 9 displays the four plots of FIG. 8 with each constant temperature plot normalized to the value of its fluorescent signal at 50 mg/dL.
Figure 10:
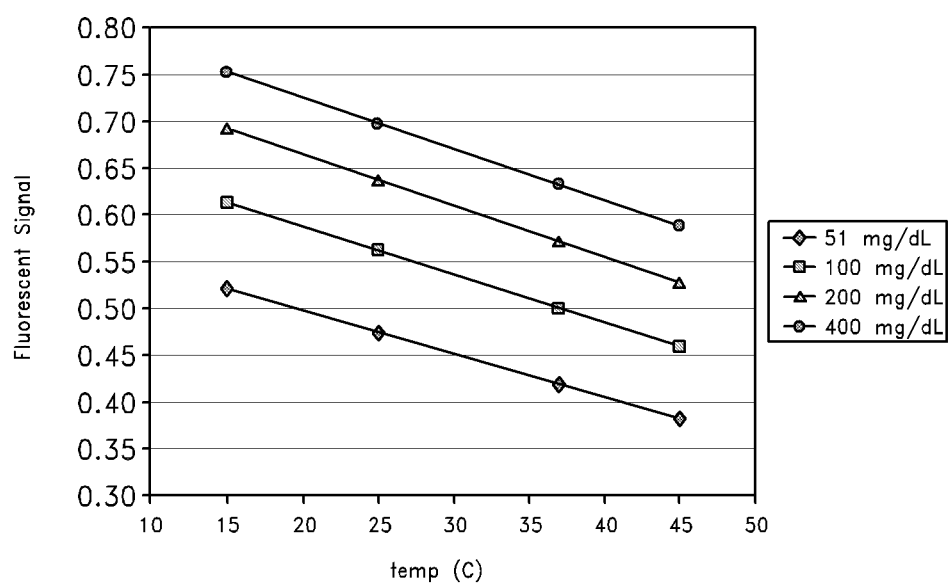
FIG. 10 displays essentially the same raw data as FIG. 8, but instead displays four plots of fluorescent signal versus temperature at four different glucose concentrations.

This data is displayed in FIGS. 8-10. FIG. 8 displays four plots of fluorescent signal versus glucose concentration—one plot for each of these four temperatures. FIG. 9 displays the same data with each constant temperature plot normalized to the value of its fluorescent signal at 50 mg/dL. FIG. 10 displays essentially the same raw data as FIG. 8, but instead displays four plots of fluorescent signal versus temperature—one plot for each of the four glucose concentrations. Apparent from FIG. 10, is that the fluorescent signal's temperature dependence—at constant glucose concentration—is approximately linear.

Using the data plotted in FIG. 8, values of the Michaelis-Menten parameters at 15° C., $a_{15}$, $b_{15}$, and $c_{15}$, were determined by fitting (using linear least squares) the modified Michaelis-Menten equation of Equation 1 to the fluorescence data generated at 15° C. Similarly, values of $a_{25}$, $b_{25}$, and $c_{25}$ were determined by fitting Equation 1 to the fluorescence data generated at 25° C.; values of $a_{37}$, $b_{37}$, and $c_{37}$ were determined by fitting Equation 1 to the fluorescence data generated at 37° C.; and finally, values of $a_{45}$, $b_{45}$, and $c_{45}$ were determined by fitting Equation 1 to the fluorescence data generated at 45° C.

The process was repeated over four additional glucose sensors of the same design as the first to improve the accuracy of the calibration. Thus, fluorescent signals were generated with each of the four additional glucose sensors, at each of the same four temperatures (15° C., 25° C., 37° C., and 45° C.), and at each of the same four glucose concentrations (50 mg/dL, 100 mg/dL, 200 mg/dL, and 400 mg/dL). This data corresponding to each of the four sensors was fit with Equation 1 (as was done with the initial sensor) in order to generate values of $a_{15}$, $a_{25}$, $a_{37}$, $a_{45}$, $b_{15}$, $b_{25}$, $b_{37}$, $b_{45}$, $c_{15}$, $c_{25}$, $c_{37}$, and $c_{45}$ for each additional glucose sensor. The data was averaged over all five sensors for each of these quantities to generate $\bar{a}_{15}$, $\bar{a}_{25}$, $\bar{a}_{37}$, $\bar{a}_{45}$, $\bar{b}_{15}$, $\bar{b}_{25}$, $\bar{b}_{37}$, $\bar{b}_{45}$, $\bar{c}_{15}$, $\bar{c}_{25}$, $\bar{c}_{37}$, and $\bar{c}_{45}$.

Determination of the temperature calibration parameters (TempCos) corresponding to Equations 2 and 3 was done using these averaged values. Thus, the temperature calibration parameters corresponding to the "a" Michaelis-Menten parameter—i.e. $m_{a_T}$ and $\beta_{a_T}$—were determined by normalizing each of the "a" parameters to $\bar{a}_{37}$ and fitting a line (again using linear least squares) to a plot of these values—i.e. $\bar{a}_{15}/\bar{a}_{37}$, $\bar{a}_{25}/\bar{a}_{37}$, 1, $\bar{a}_{45}/\bar{a}_{37}$ versus temperature—the slope and intercept being $m_{a_T}$ and $\beta_{b_T}$, respectively. The same was done with the temperature calibration parameters $m_{b_T}$ and $\beta_{b_T}$, corresponding to the "b" Michaelis-Menten parameter, and $m_{c_T}$, and $\beta_{c_T}$, corresponding to the "c" Michaelis-Menten parameter. The resulting values for these TempCos are summarized in the Table 1, below.

TABLE 1

| | |
|---|---|
| $m_{a_T} = -0.009924$ | $\beta_{a_T} = 1.367206$ |
| $m_{b_T} = -0.006467$ | $\beta_{b_T} = 1.239281$ |
| $m_{c_T} = 0.007856$ | $\beta_{c_T} = 0.709328$ |

An equation for computing a temperature corrected glucose concentration from a fluorescent signal and these temperature calibration parameters may be derived by substituting Equation 2 into Equation 1 which yields $$[Glu] = \frac{c_{37} * \tau_c(T) * [G_i - a_{37} * \tau_a(T)]}{a_{37} * \tau_a(T) + b_{37} * \tau_b(T) - G_i} \quad \text{(Equation 6)}$$

and then, using Equation 3, further substituting for $\tau_a(T)$, $\tau_b(T)$, and $\tau_c(T)$ in Equation (6), which yields $$[Glu] = \frac{c_{37} * (m_c * T + b_c) * [G_i - a_{37} * (m_a * T + b_a)]}{a_{37} * (m_a * T + b_a) + b_{37} * (m_b * T + b_b) - G_i} \quad \text{(Equation 7)}$$

EXAMPLE 2

Figure 11:
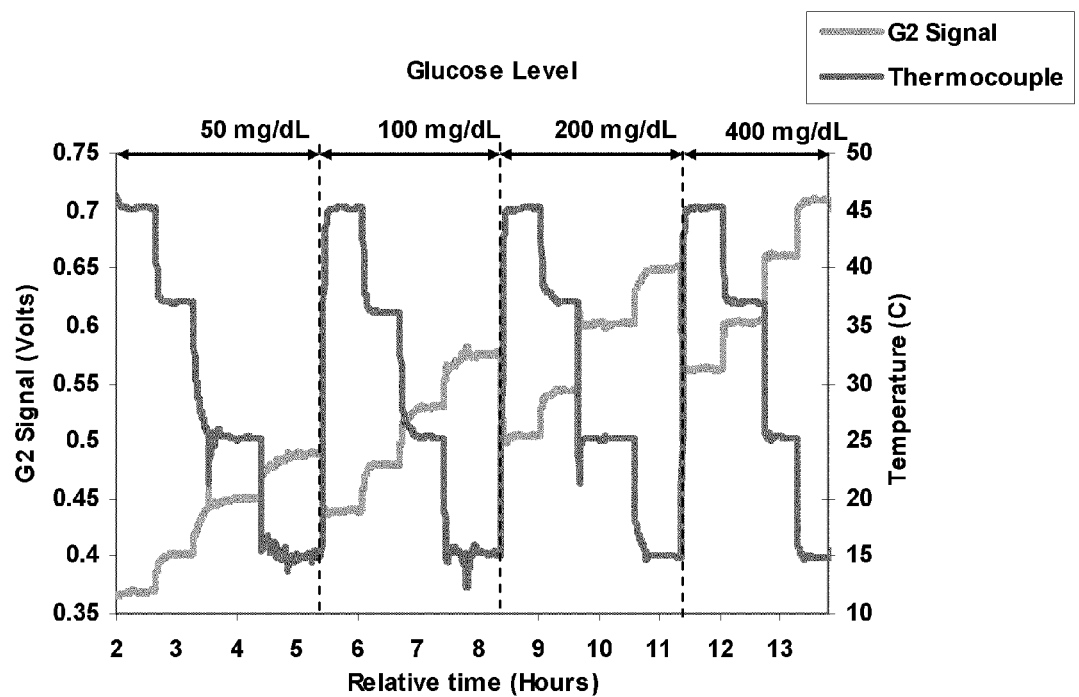
FIG. 11 displays the fluorescent signal generated by one embodiment of an analyte measuring device disclosed herein at four temperatures and four glucose concentrations.

This example also concerns the temperature calibration of an equilibrium fluorescence glucose GluCath sensor. Again, the GluCath sensor employs an HPTS-Cys-MA dye operably coupled to a 3,3'-oBBV quencher, with the dye and quencher immobilized within a hydrogel disposed along the distal region of an optical fiber, while the proximal end of the optical fiber is coupled to a light source. The temperature dependence of this sensor's fluorescence response to glucose was assumed to be described by the modified Michaelis-Menten equation of Equation 1 as described above. The Michaelis-Menten parameters were assumed to bear a linear relationship to temperature as set forth in Equations 2 and 3 above. Using this model of the glucose sensor's temperature dependence, the TempCos, $m_{a_T}$, $\beta_{a_T}$, $m_{b_T}$, $\beta_{b_T}$, $m_{c_T}$, and $\beta_{c_T}$, were determined by the methodology described above in reference to Equations 2 and 3. Specifically, the effect of temperature on the fluorescent signal was determined experimentally by measuring the signal at four temperatures (15° C., 25° C., 37° C., and 45° C.) and four glucose concentrations (50 mg/dL, 100 mg/dL, 200 mg/dL, and 400 mg/dL). At each temperature and glucose level the stable signal, $G_2$, was recorded. The raw data from this experiment is plotted in FIG. 11.

Figure 12:
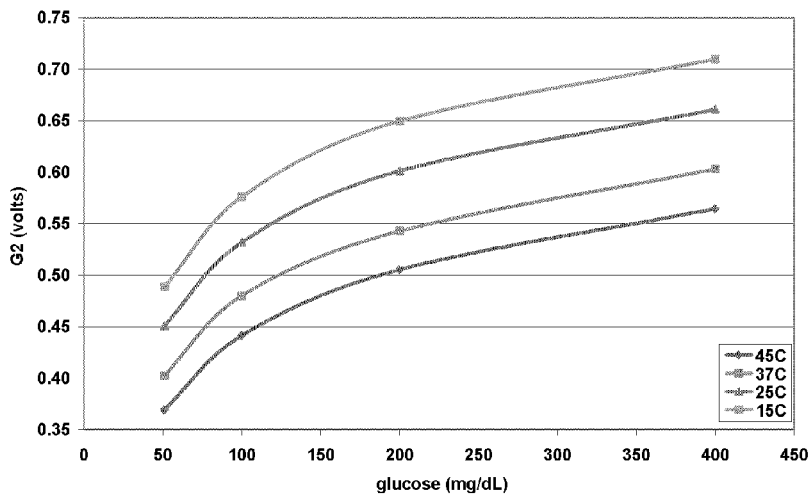
FIG. 12 displays a plot of fluorescent signal versus glucose concentration at four temperatures as generated by one embodiment of an analyte measuring device disclosed herein.

FIG. 12 plots glucose response—$G_2$ versus glucose concentration—for each of the four temperatures. This figure illustrates that the fluorescent signal $G_2$ is inversely related to temperature and also that there are large differences in the fluorescent signal $G_2$ at all glucose levels over the range of temperatures likely to be encountered in the intensive care unit—i.e. 15° C. to 45° C. At each fixed temperature, the modified Michaelis-Menten equation (equation 1) was fit to the fluorescent signal $G_2$ versus glucose concentration to determine best-fit values of the Michaelis-Menten parameters $a_T$, $b_T$, and $c_T$ at each temperature. The four best-fit modified Michaelis-Menten equations are overlaid on the data in FIG. 12. The quality of the fits is evident from the figure.

Figure 13:
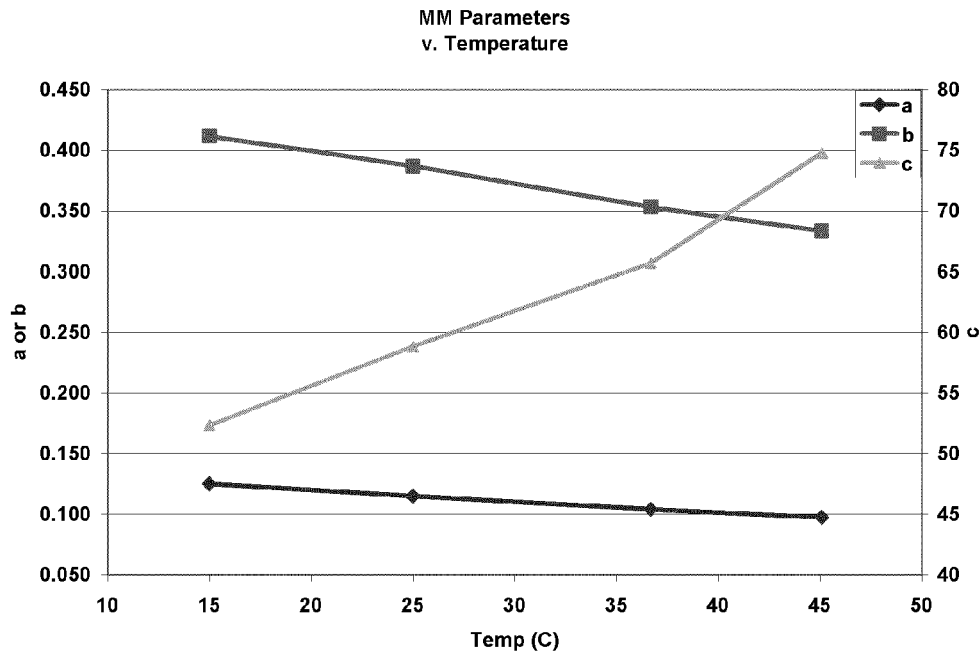
FIG. 13 displays plots of the values of the three Michaelis-Menten parameters versus temperature.

FIG. 13 plots each of $a_T$, $b_T$, and $c_T$ versus temperature, the values of the Michaelis-Menten parameters corresponding to the best-fits displayed in FIG. 12. The plots of each of $a_T$, $b_T$, and $c_T$ versus temperature illustrate that, in some embodiments, best-fit values of the Michaelis-Menten parameters change approximately linearly with temperature. The best-fit values of the Michaelis-Menten parameters at each temperature were normalized to their values at 37° C. and the normalized values were fit using linear regression to compute slopes and intercepts as shown in FIG. 14.

Figure 14:
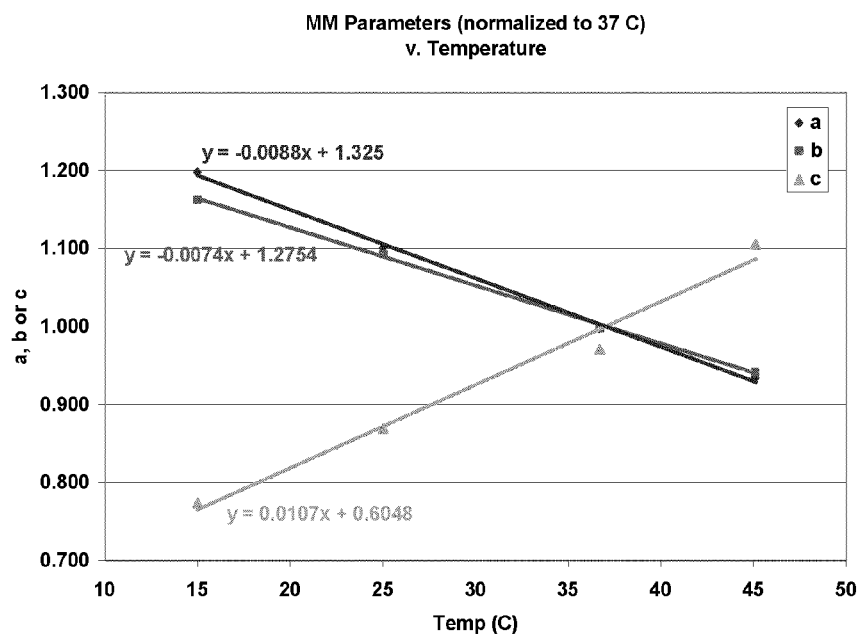
FIG. 14 displays plots of normalized values of the three Michaelis-Menten parameters versus temperature and displays a best fit line associated with each normalized parameter.

The slopes and intercepts displayed in FIG. 14 correspond to the "temperature calibration coefficients" $m_{a_T}$, $m_{b_T}$, $m_{c_T}$, $\beta_{a_T}$, $\beta_{b_T}$, and $\beta_{c_T}$, i.e. "TempCos," as described above. The particular values computed from the data in this example are listed in Table 2, below.

TABLE 2

| | |
|---|---|
| $m_{a_T} = -0.008785$ | $\beta_{a_T} = 1.32509$ |
| $m_{b_T} = -0.007444$ | $\beta_{b_T} = 1.275413$ |
| $m_{c_T} = 0.010681$ | $\beta_{c_T} = 0.604815$ |

The TempCos can then be used to predict the temperature dependent Michaelis-Menten parameters $a_T$, $b_T$, and $c_T$ by multiplying the 37° C. Michaelis-Menten parameters $a_{37}$, $b_{37}$, and $c_{37}$, by a temperature correction factor, $\tau_{a_T}(T)$, $\tau_{b_T}(T)$, or $\tau_{c_T}(T)$ respectively, as indicated by Equation 3. Again, the 37° C. Michaelis-Menten parameters $a_{37}$, $b_{37}$, and $c_{37}$ may be measured at calibration, determined by a factory calibration, or potentially supplied by any other appropriate method.

Figure 15:
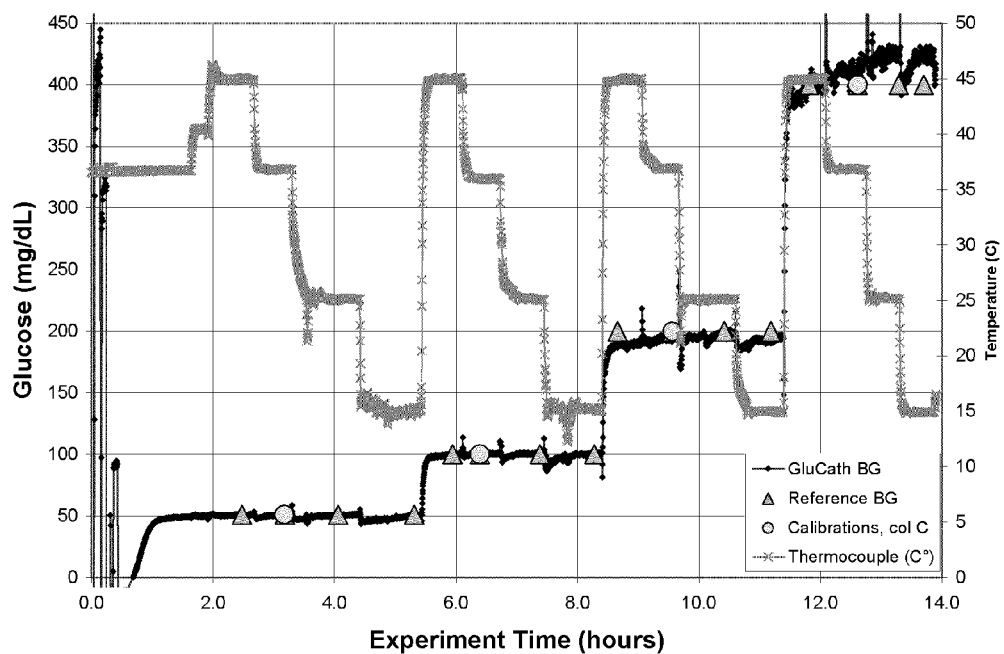
FIG. 15 compares a plot of glucose concentration as determined by reference measurements with a plot of glucose concentration as determined by one embodiment of an analyte measuring device disclosed herein.

In order to illustrate the accuracy of employing the above-described temperature correction methodology, these TempCos were used to perform temperature correction on an independent data set, as illustrated in FIG. 15. In the independent data set, the $G_2$ fluorescent signal versus plasma glucose concentration was measured at four reference plasma glucose levels (50 mg/dL, 100 mg/dL, 200 mg/dL, and 400 mg/dL) and at four temperatures (15° C., 25° C., 37° C., and 45° C.). The reference measurements of plasma glucose level are indicated as single points (small and medium sized circles) in FIG. 15. Temperature measurements as determined by thermocouple are also displayed.

The other curve displayed in FIG. 15 is the temperature corrected plasma glucose concentration. To compute this curve, the four reference plasma glucose levels at 37° C. (indicated by medium sized circles in FIG. 15) were fit to a modified Michaelis-Menten equation (Equation 1, as previously described) to generate values of the 37° C. Michaelis-Menten parameters ($a_{37}$, $b_{37}$, and $c_{37}$). The temperature corrected plasma glucose concentration curve in FIG. 15 was then computed at each temperature read by the thermocouple by inputting into Equations 2 and 3 these 37° C. Michaelis-Menten parameters ($a_{37}$, $b_{37}$, and $c_{37}$), the TempCos ($m_{a_T}$, $m_{b_T}$, $m_{c_T}$, $\beta_{a_T}$, $\beta_{b_T}$, and $\beta_{c_T}$, as determined in the table above), and the corresponding temperature read by the thermocouple. The temperature corrected plasma glucose concentration curve matches closely the reference plasma glucose levels (indicated by the small and medium sized circles) in FIG. 15. In fact, the mean absolute relative deviation ("MARD") between the computed temperature corrected plasma glucose concentrations and the reference plasma glucose levels was only 2.46% (excluding the 37° C. reference values used for calibration). The MARD for the same data set without temperature correction was 170%.

Methods of Measuring pH

Figure 16:
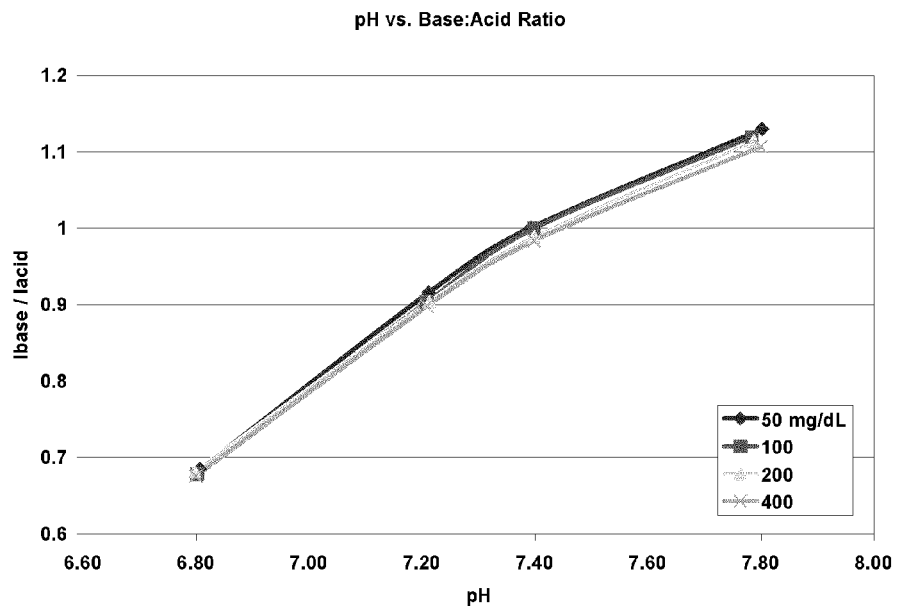
FIG. 16 displays plots of the ratio of two fluorescent signals versus pH at four glucose concentrations.

If a solution's measured analyte concentration is to be corrected for pH effects, the pH of the solution must be measured or estimated in some manner. In some embodiments a separate pH sensor may be used to measure pH. In other embodiments, the same indicator system which is used to generate a signal indicative of analyte concentration may be used to measure pH. For instance, the ratio of two green signals generated by the indicator system may be used to compute pH through the following relationship:

$$pH = m_{pH} * \frac{G_1}{G_2} + \beta_{pH} \quad \text{(Equation 8)}$$

where $m_{pH}$ is the slope and $\beta_{pH}$ is the intercept of pH versus $G_1/G_2$. The ratio, $G_1/G_2$, is calculated from $G_1$ which is the fluorescence emission at 550 nm when the fluorophore is excited at 470 nm, and $G_2$ which is the fluorescence emission at 550 nm when the fluorophore is excited at 420 nm. The approximate linearity of the relationship between $G_1/G_2$ and pH is illustrated in FIG. 16 over a range of glucose concentrations (50 mg/dL, 100 mg/dL, 200 mg/dL, and 400 mg/dL) and pH levels (6.8, 7.2, 7.4, and 7.8), although some greater deviation from linearity occurs between pH 7.4 and pH 7.8. Note, that $G_1/G_2$ is represented in FIG. 16 as Ibase/Iacid since, as indicated above, 470 nm is the absorption maximum of the fluorophore's base-form, and 420 nm is the absorption maximum of the fluorophore's acid-form. Also, note that the values of $G_1/G_2$ plotted in FIG. 16 have been normalized to the 100 mg/dL, pH 7.4 value of $G_1/G_2$. Thus, Equation 8 may be used to predict pH level from the $G_1/G_2$, ratio once the constants $m_{pH}$ and $\beta_{pH}$ have been determined. In some embodiments, each analyte measurement device may be individually calibrated to determine the constants $m_{pH}$ and $\beta_{pH}$ appropriate for that individual device. In other embodiments, an entire batch of measurement devices may be calibrated by selecting several devices from the batch, determining values of $m_{pH}$ and $\beta_{pH}$ for each selected device, and averaging the values of $m_{pH}$ and $\beta_{pH}$ obtained for each selected devices to produce averaged values of $m_{pH}$ and $\beta_{pH}$ valid for the entire batch of measurement devices for use with Equation 8. In still other embodiments, averaged values of $m_{pH}$ and $\beta_{pH}$ may be determined as just described, but a one-point calibration is performed to individually calibrate each sensor in the batch while taking advantage of the averaged values of $m_{pH}$ and $\beta_{pH}$ obtained for the entire batch. For instance, in some embodiments, the one point calibration performed on each individual measuring device may involve using the individual device to measure $G_1$ and $G_2$ for a standard solution having a glucose concentration of 100 mg/dL at pH 7.4. These values may then be used in Equation 9

$$\text{pH} = m_{pH} * \frac{\frac{G_1}{G_2}}{\frac{G_{1,7.4}}{G_{2,7.4}}} + \beta_{pH} \quad \text{(Equation 9)}$$

where:
- $G_1$ is the fluorescent emission, either referenced or unreferenced, at 550 nm when the fluorophore is excited at 470 nm, which is the absorption maximum of the fluorophore's base-form (although other combinations of excitation and emission wavelengths are also feasible for use as the numerator of the $G_1/G_2$ ratio in Equation 9),
- $G_2$ is the fluorescence emission, either referenced or unreferenced, at 550 nm when the fluorophore is excited at 420 nm, which is the absorption maximum of the fluorophore's acid-form (although other combinations of excitation and emission wavelengths are also feasible for use as the denominator of the $G_1/G_2$ ratio in Equation 9),
- $G_{1,7.4}$=$G_1$ signal at pH 7.4 and 100 mg/dL glucose concentration,
- $G_{2,7.4}$=$G_2$ signal at pH 7.4 and 100 mg/dL glucose concentration,
- $m_{pH}$=pH slope, and
- $\beta_{pH}$=pH intercept.

Thus, once universal values of $m_{pH}$ and $\beta_{pH}$ are determined for the batch of measurement devices, and $G_{1,7.4}$ and $G_{2,7.4}$ are determined via one-point calibration for the individual measurement device, a measured ratio $G_1/G_2$ may be used in Equation 9 to compute the pH level of the solution of analyte. It was also discovered that the determination of pH from $G_1/G_2$ is effected by the temperature of the solution—see for instance, Example 3, below. Moreover, for purposes of estimating pH from the measured ratio $G_1/G_2$, the temperature dependence may be taken into account by allowing $m_{pH}$ and $\beta_{pH}$ to vary with temperature. In particular, the temperature dependence of $m_{pH}$ and $\beta_{pH}$ may be modeled using Equations 10 and 11:

$$m_{pH} = \frac{h}{T} + i \quad \text{(Equation 10)}$$

$$\beta_{pH} = j * \sqrt{T} + k \quad \text{(Equation 11)}$$

where h, i, j, and k are empirically determined constants—see, for instance, Example 3, below. Substituting Equations 10 and 11 into Equation 9 gives an expression for computing pH from the ratio $G_1/G_2$ which accurately, albeit approximately, takes temperature into account.

$$\text{pH} = \left(\frac{h}{T} + i\right) * \frac{\left(\frac{G_1}{G_2}\right)}{\left(\frac{G_{1,7.4}}{G_{2,7.4}}\right)} + j * \sqrt{T} + k \quad \text{(Equation 12)}$$

EXAMPLE 3

Figure 17:
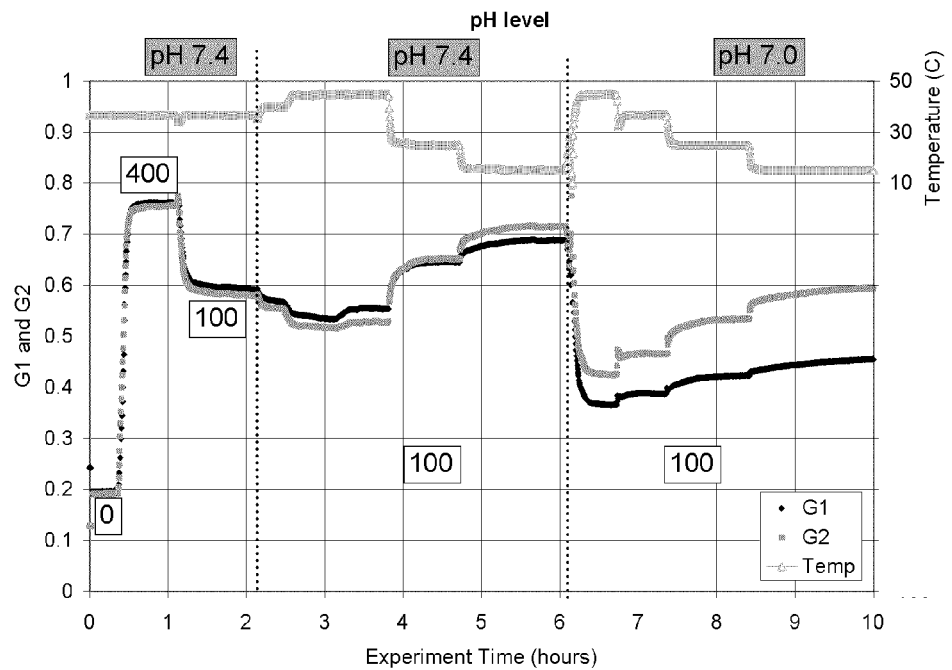
FIG. 17 displays plots of two fluorescent signals at four temperatures and four pH levels.
Figure 18:
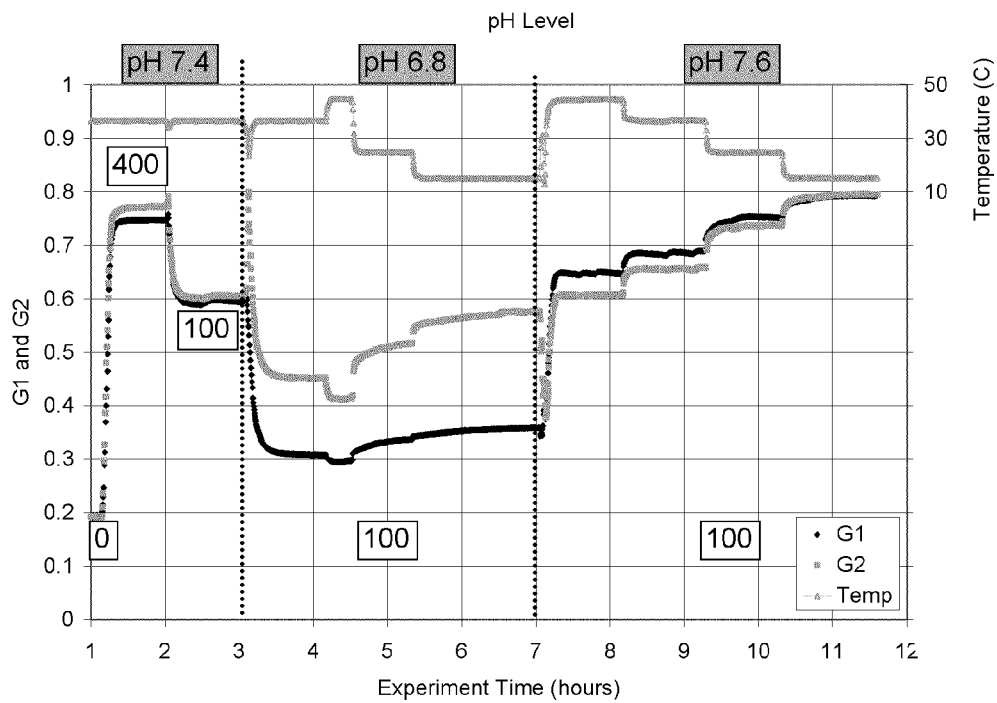
FIG. 18 displays plots of two fluorescent signals at four temperatures and four pH levels.
Figure 19:
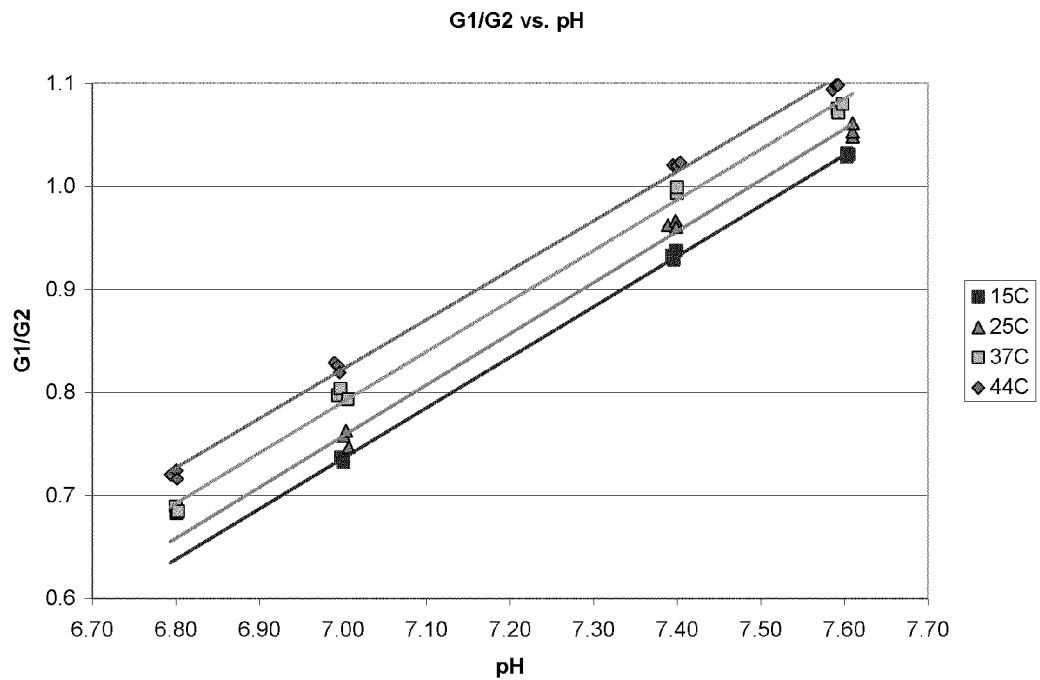
FIG. 19 displays plots of the ratio of two fluorescent signals versus pH at four temperatures, along with best fit lines corresponding to each temperature.
Figure 20:
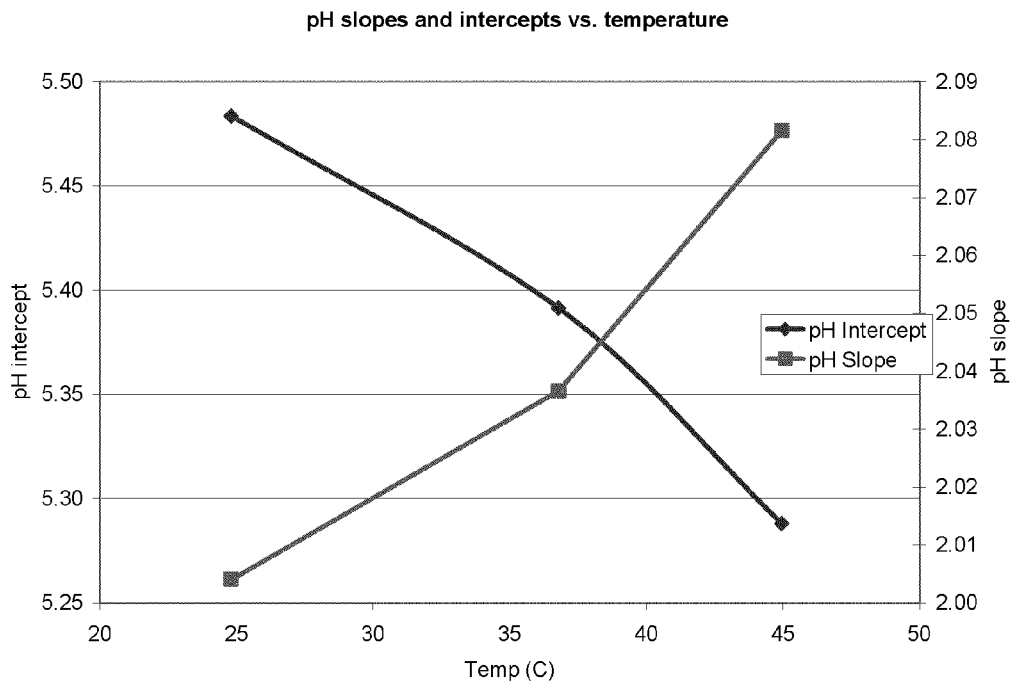
FIG. 20 displays plots of the slopes and intercepts of the best fit lines of FIG. 19 at each of the temperatures from that figure.

In order to accurately determine pH from the measured $G_1/G_2$ ratio using Equation 12, so as to take temperature into account, testing was conducted to empirically determine the constants, h, i, j, and k. In the experiment displayed in FIGS. 17 and 18, $G_1$ and $G_2$ were measured with a GluCath sensor at four temperatures (15° C., 25° C., 37° C., and 45° C.) and four pH levels (6.8, 7.0, 7.4, 7.6), all at a glucose concentration of 100 mg/dL. Note that FIGS. 17 and 18 demonstrate, among other things, that the $G_1$ and $G_2$ fluorescent signals are effected by temperature change, even when the pH level is held constant. FIG. 19 shows the ratio of the measured values of $G_1$ and $G_2$ from FIGS. 17 and 18 plotted versus pH at each of the four temperatures. A line was fit (using linear regression) to each series of $G_1/G_2$ values corresponding to the same temperature. FIG. 19 illustrates that the intercepts of these lines, and to a lesser extent the slopes of these lines, vary with temperature. To model this temperature dependence, the associated slopes and intercepts are plotted as functions of temperature in FIG. 20. Equation 10 was used to model the temperature dependence of the slope $m_{pH}$, and based on the data displayed in FIG. 20 best fit values of the constants h, and i were determined. Similarly, Equation 11 was used to model the temperature dependence of the intercept $\beta_{pH}$, and based on the data displayed in FIG. 20 best fit values of the constants j, and k were determined. The best fit values of h, i, j, and k to be used in Equation 12 are listed in Table 3.

TABLE 3

| |
| --- |
| h = −10.9415 |
| i = 2.3264 |
| j = −0.16908 |
| k = 6.3983 |

Figure 21:
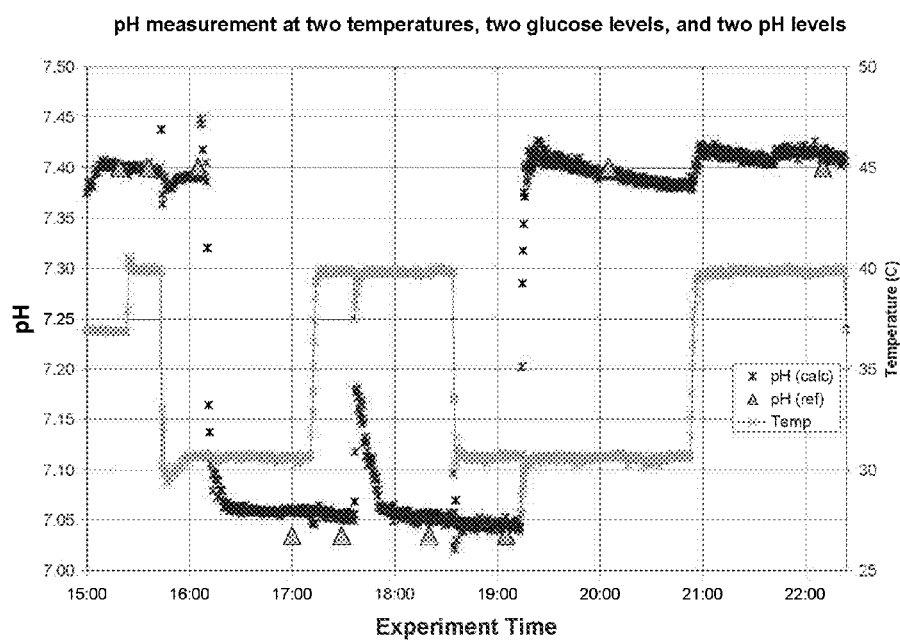
FIG. 21 compares a plot of pH as determined by reference measurements with a plot of pH as determined by one embodiment of an analyte measuring device disclosed herein.

An independent data set was generated to test the accuracy of using Equation 12 to compute pH level from measured $G_1/G_2$ ratio, using these values of h, i, j, and k. FIG. 21 displays both measured reference pH values (small and medium sized dots) and values of pH computed from $G_1/G_2$ with Equation 12 (sequence of 'x' marks)—at two temperatures (30° C., and 40° C.) and two glucose levels (50 mg/dL and 100 mg/dL). Note that the medium sized dot (corresponding to a glucose concentration of 100 mg/dL and pH 7.4) served as the reference point for the one-point calibration as described above. The results are displayed in the following table. As indicated in Table 4, the average pH offset for this data set was +0.008.

TABLE 4

| Glucose (mg/dL) | Temp (° C.) | Reference pH | pH Calculated from $G_1/G_2$ | Difference |
|---|---|---|---|---|
| 100 | 40 | 7.400 | 7.405 | 0.005 |
| 100 | 30 | 7.400 | 7.394 | −0.006 |
| 100 | 30 | 7.035 | 7.060 | 0.025 |
| 100 | 40 | 7.035 | 7.056 | 0.021 |
| 50 | 40 | 7.035 | 7.047 | 0.012 |
| 50 | 30 | 7.035 | 7.043 | 0.008 |
| 50 | 30 | 7.400 | 7.395 | −0.005 |
| 50 | 40 | 7.400 | 7.407 | 0.007 |
| | | | Avg | 0.008 |

Methods of Estimating Analyte Concentration Incorporating pH Correction

Some embodiments of the measurement devices disclosed herein generate a signal indicative of analyte concentration which exhibits a pH dependence. For example, if two solutions of precisely the same analyte concentration are measured at two different pH levels with the same measurement device, in some embodiments, the measurement device may generate differing signals indicative of the two analyte concentrations. Thus, the accuracy of determining a solution's true analyte concentration based on such as signal may be improved by taking the pH of the solution into account.

It has been discovered that for some embodiments of the measurement devices disclosed herein, and in particular, for glucose measurement devices employing a quencher binding moiety operably coupled to a fluorophore, the pH dependence of the fluorescent signal approximately follows a modified version of the classic Michaelis-Menten equation from enzyme kinetics:

$$[Glu] = \frac{c_{pH} * [G_i - a_{pH}]}{a_{pH} + b_{pH} - G_i} \quad \text{(Equation 13)}$$

where:
[Glu] is the estimated glucose concentration,
$a_{pH}$ is the first Michaelis-Menten parameter "a", at a particular pH,
$b_{pH}$ is the second Michaelis-Menten parameter "b", at the same particular pH,
$c_{pH}$ is the third Michaelis-Menten parameter "c", at the same particular pH, and
$G_i$ is the fluorescent signal (i=1,2), either referenced or unreferenced, where $G_1$ is the fluorescence emission at 550 nm when the fluorophore is excited at 470 nm (which is the absorption maximum of the fluorophore's base-form), and $G_2$ is the fluorescence emission at 550 nm when the fluorophore is excited at 420 nm (which is the absorption maximum of the fluorophore's acid-form). Note, however, that other combinations of excitation and emission wavelengths are also feasible for use in Equation 13. In the Examples below, $G_2$ has been used, unless indicated otherwise.

As with temperature dependence, the fact that pH dependence may be described by a modified Michaelis-Menten equation is an interesting and surprising result. Various embodiments of the measurement devices disclosed herein employ a quencher-fluorophore indicator system which measures analyte concentration through the establishment of an equilibrium between the analyte of interest, the binding moiety (e.g. quencher), and the fluorophore. In such a system, analyte concentration is not measured by enzymatic consumption or conversion of the analyte. In contrast, the classic Michaelis-Menten equation specifically describes enzyme kinetics, a non-equilibrium phenomena involving the consumption/conversion of the enzyme's substrate by the enzyme. Therefore, it is not to be expected that an equation closely related to the classic Michaelis-Menten equation would effectively describe the pH dependence of these types of quencher-fluorophore-based measurement devices and analyte sensing elements (or other measurement devices and analyte sensing elements functioning through analogous equilibrium mechanisms). In any event, knowledge that these devices (and similar devices) exhibit a pH dependence which follows a modified Michaelis-Menten equation allows the use of pH correction methods and algorithms to improve the accuracy of analyte concentration measurements. Such methods and algorithms are disclosed herein, along with measurement devices which implement such methods and algorithms.

Accordingly, some embodiment methods of estimating an analyte concentration include generating a signal indicative of analyte concentration and a signal indicative of pH. In some embodiments, the signal indicative of the analyte concentration and the signal indicative of the pH are both generated from a set of at least two signals each of which is indicative of both the pH and the analyte concentration. For instance, these could be the $G_1$ and $G_2$ fluorescent signals described above, both of which are indicative of both analyte concentration and pH. In some embodiments, the $G_2$ fluorescent signal itself may be treated as the signal indicative of analyte concentration, while $G_1$ and $G_2$ are used as signals indicative of pH, for example, in the pH determination algorithm described above. Since, in some embodiments, the signal indicative of analyte concentration exhibits a pH dependence, in some embodiments, the signal indicative of pH may be used to adjust the signal indicative of analyte concentration to correct for pH dependence. Thus, in certain such embodiments, the methods further include transforming the signal indicative of the analyte concentration utilizing an equation of the form of a modified Michaelis-Menten equation, such as Equation 1 above, depending on Michaelis-Menten parameters, such as the parameters "a", "b", and "c", as described above as first, second, and third Michaelis-Menten parameters with reference to Equation 13.

Of course, it is to be understood that when a signal is described herein as being indicative of one physical quantity, such description is not meant to necessarily preclude that signal from also being indicative of another physical quantity. For instance, a computed analyte concentration that may be improved through pH correction, was likely computed from a signal indicative of analyte concentration which contained some pH dependency. Therefore, to a certain extent, such a signal indicative of analyte concentration may also be considered a signal indicative of pH, as will be readily appreciated by one of skill in the art.

The pH dependence of Equation 13 is exhibited through the Michaelis-Menten parameters $a_{pH}$, $b_{pH}$, and $c_{pH}$, as indicated by the subscript "pH" labeling these parameters. In some embodiments, the pH dependence may need to be determined through a pH calibration. Thus, in certain embodiment methods, the values of one or more of the Michaelis-Menten parameters may be set based on data which includes pH calibration data and the signal indicative of a pH.

For example, in some embodiment methods, the pH calibration data may be generated by a pH calibration method. The pH calibration method may include selecting a first test analyte sensing element, and creating and/or providing a set of at least three solutions of differing known analyte concentrations. In certain such embodiments, a first pH is selected (pH1), three solutions of the set of at least three solutions are adjusted to a pH substantially similar to the selected first pH, and a first set of at least three signals is generated using the first test analyte sensing element, each signal indicative of the concentration of analyte in a different one of the three solutions at the first pH. Measurements are then made at a second pH. Thus, in certain embodiments, a second pH is selected (pH2), three solutions of the set of at least three solutions (each of the three may be the same or different than a solution chosen for the first pH) are adjusted to a pH substantially similar to the selected second pH, and a second set of at least three signals is generated using the first test analyte sensing element, each signal indicative of the concentration of analyte in a different one of the three solutions at the second pH. Of course, more than three solutions may be used in either of these steps. And more than two pHs may also be employed. Generally, the more solutions of differing concentration and the greater number of different pHs that are employed, the greater the accuracy of the resulting calibration data.

Once the solutions having known analyte concentrations have been measured, and the first and second sets of at least three signals have been generated, in some embodiments, the sets of signals are used to determine (usually approximately) the relationship between one or more of the Michaelis-Menten parameters and pH. For example, in some embodiments, the pH calibration method may further include computing values of each of a first, second, and third Michaelis-Menten parameter at the first pH ($a_{pH1}$, $b_{pH1}$, and $c_{pH1}$) by an algorithm comprising fitting a modified Michaelis-Menten equation to a first fit dataset comprising the first set of at least three signals. In certain such embodiments, the pH calibration method may further include computing values of each of a first, second, and third Michaelis-Menten parameter at the second pH ($a_{pH2}$, $b_{pH2}$, and $c_{pH2}$) by an algorithm comprising fitting a modified Michaelis-Menten equation to a second fit dataset comprising the second set of at least three signals. Thus, in methods such as these, each of the three Michaelis-Menten parameters has been determined at least two pHs, providing data which may be used to create a model of the pH dependence of each of the three Michaelis-Menten parameters.

To model the pH dependence of the Michaelis-Menten parameters, in some embodiments, the pH calibration method may further include selecting an equation relating the first Michaelis-Menten parameter ($a_{pH}$) to pH, the equation depending on a first set of pH calibration parameters; and setting a value for each calibration parameter of the first set of calibration parameters based on the value of the first Michaelis-Menten parameter at the first pH ($a_{pH1}$) and the value of the first Michaelis-Menten parameter at the second pH ($a_{pH2}$). In some embodiments, similar steps are performed with respect to the second and third Michaelis-Menten parameters ($b_{pH}$ and $c_{pH}$). Thus, for example, the pH calibration method may further include selecting an equation relating the second Michaelis-Menten parameter ($b_{pH}$) to pH, the equation depending on a second set of pH calibration parameters; and setting a value for each calibration parameter of the second set of calibration parameters based on the value of the second Michaelis-Menten parameter at the first pH ($b_{pH1}$) and the value of the second Michaelis-Menten parameter at the second pH ($b_{pH2}$). Similarly, in some embodiments, the pH calibration method may further include selecting an equation relating the third Michaelis-Menten parameter ($c_{pH}$) to pH, the equation depending on a third set of pH calibration parameters; and setting a value for each calibration parameter of the third set of calibration parameters based on the value of the third Michaelis-Menten parameter at the first pH ($c_{pH1}$) and the value of the third Michaelis-Menten parameter at the second pH ($c_{pH2}$).

Furthermore, in some embodiments, equations linear in pH may be selected to relate the first and second Michaelis-Menten parameters to pH, while a more complicated equation may be selected to relate the third Michaelis-Menten parameter to pH. For instance, in some embodiments, the first, second, and third Michaelis-Menten parameters may be written as $$a_{pH}=a_{7.4}*\rho_{a_{pH}}(pH),$$

$$b_{pH}=b_{7.4}*\rho_{b_{pH}}(pH), \text{ and}$$

$$c_{pH}=c_{7.4}*\rho_{c_{pH}}(pH) \quad \text{(Equation 14)}$$

where $\rho_{a_{pH}}(pH)$, $\rho_{b_{pH}}(pH)$, and $\rho_{c_{pH}}(pH)$ are "pH correction factors" which approximately account for the pH dependence of $a_{pH}$, $b_{pH}$, and $c_{pH}$. When the relationship between Michaelis-Menten parameter and pH is written as such, each Michaelis-Menten parameter $a_{pH}$, $b_{pH}$, and $c_{pH}$, is determined by multiplying the pH 7.4 Michaelis-Menten parameter $a_{7.4}$, $b_{7.4}$, and $c_{7.4}$, by its corresponding "pH correction factor," $\rho\rho_{a_{pH}}(pH)$, $\rho_{b_{pH}}(pH)$, or $\rho_{c_{pH}}(pH)$, respectively. The pH 7.4 Michaelis-Menten parameters may be determined by fitting a modified Michaelis-Menten equation to a set of signals indicative of the analyte concentration of a plurality of solutions of differing analyte concentrations held at pH 7.4, as described above with respect to, for example, pH1 and pH2. Alternatively, the parameters $a_{7.4}$, $b_{7.4}$, and $c_{7.4}$ may be supplied by a factory calibration as described in provisional U.S. patent application No. 61/184,747, "Algorithms for Calibrating an Analyte Sensor," filed Jun. 5, 2009, which is hereby incorporated herein by reference in its entirety. As yet another alternative, $a_{7.4}$, $b_{7.4}$, and $c_{7.4}$ may be determine via a one-point in vivo calibration as also disclosed in the same application.

To determine the "pH correction factors," $\rho_{a_{pH}}(pH)$, $\rho_{b_{pH}}(pH)$, $\rho_{c_{pH}}(pH)$, some embodiment methods may select a first equation linear in pH to relate the first Michaelis-Menten parameter to pH, and select a second equation linear in pH to relate the second Michaelis-Menten parameter to pH. In certain such embodiment methods, an equation is selected to relate the third Michaelis-Menten parameter to pH which comprises a fraction wherein the numerator is equal to an exponential function of an equation linear in the inverse of pH, and the denominator is equal to an exponential function of the same linear function in the inverse of pH evaluated at pH 7.4. If such equations in pH are selected, then the pH correction factors may be written as $$\rho_{a_{pH}}(pH) = m_{a_{pH}} *pH + \beta_{a_{pH}}, \quad \text{(Equation 15)}$$

$$\rho_{b_{pH}}(pH) = m_{b_{pH}} *pH + \beta_{b_{pH}}, \text{ and}$$

-continued
$$\rho_{c_{pH}}(\text{pH}) = \frac{e^{\left(\frac{m_{c_{pH}}}{\text{pH}}+\beta_{c_{pH}}\right)}}{e^{\left(\frac{m_{c_{pH}}}{7.4}+\beta_{c_{pH}}\right)}}.$$

where the slopes, $m_{a_{pH}}$, $m_{b_{pH}}$, $m_{c_{pH}}$, and intercepts $\beta_{a_{pH}}$, $\beta_{b_{pH}}$, $\beta_{c_{pH}}$, are collectively referred to as pH calibration coefficients ("pHCos"). However, analytic functional forms other than linear equations may be chosen to relate the pH correction factors and/or Michaelis-Menten parameters to pH (or to inverses of pH as indicated by Equation 15's expression for $\rho_{c_{pH}}(\text{pH})$). For instance, in some embodiments, quadratic or higher-order polynomials in pH may be appropriate and/or desirable.

In various embodiments, a pH calibration method used to determine values of these pHCos may require that values of the Michaelis-Menten parameters be determined at a second pH (pH2), different than pH 7.4. Values of the parameters at the second pH ($a_{pH2}$, $b_{pH2}$, and $c_{pH2}$) may be determined by fitting a modified Michaelis-Menten equation to a set of signals indicative of the analyte concentration of a plurality of solutions of differing analyte concentrations held at the second pH, as described above with respect to, for example, pH1 and pH2. Once this is done, the pH calibration coefficients $m_{a_{pH}}$ and $\beta_{a_{pH}}$ may be determined by normalizing to $a_{7.4}$ both $a_{pH2}$ and $a_{7.4}$, yielding $a_{pH2}/a_{7.4}$ and 1, and fitting a line to the normalized values versus the two pHs, pH2 and pH 7.4. The fit may be determined using linear least squares or any other method of fitting a line to a set of points. The pH calibration coefficient, $m_{a_{pH}}$, is set equal to the slope of the resulting line and the pH calibration coefficient, $\beta_{a_{pH}}$, is set equal to the intercept. The pH calibration coefficients $m_{b_{pH}}$ and $\beta_{b_{pH}}$ may be determined the same way from values of $b_{pH2}$ and $b_{7.4}$. Finally, in a manner analogous to the determination of $m_{a_{pH}}$, $\beta_{a_{pH}}$, $m_{b_{pH}}$, and $\beta_{b_{pH}}$, the pH calibration coefficients $m_{c_{pH}}$ and $\beta_{c_{pH}}$ may be determined from values of $c_{pH2}$ and $c_{7.4}$, however an additional step of linearizing Equation 15's expression for $\rho_{c_{pH}}(\text{pH})$ must first be performed. Once the calibration is complete, a pH corrected estimated glucose concentration ([Glu]) may be computed from a fluorescent signal ($G_i$) measured at a particular pH, by using the pHCos ($m_{a_{pH}}$, $\beta_{b_{pH}}$, $m_{b_{pH}}$, $\beta_{b_{pH}}$, $m_{c_{pH}}$, and $\beta_{c_{pH}}$), the pH 7.4 Michaelis-Menten parameters ($a_{7.4}$, $b_{7.4}$, and $c_{7.4}$), and the measured pH (pH) in Equations 14 and 15 to compute $a_{pH}$, $b_{pH}$, and $c_{pH}$, and then plugging $a_{pH}$, $b_{pH}$, $c_{pH}$ and the measured fluorescent signal ($G_i$) into Equation 13.

Thus, in some embodiments, the first set of pH calibration parameters comprises the slope and intercept of a first equation linear in pH, and in some embodiments, the second set of pH calibration parameters comprises the slope and intercept of a second equation linear in pH. In certain such embodiments, the third set of pH calibration parameters may comprise the slope and intercept of an equation linear in the inverse of pH which is related to the third Michaelis-Menten parameter through an exponential function divided by a constant—wherein the constant is equal to the result of evaluating the exponential function of the same equation linear in the inverse of pH evaluated at a fixed pH level. However, the pH calibration parameters (pHCos) may comprise constants associated with analytic functional forms other than linear equations which may be suitable and/or desirable. For instance, in some embodiments, the pHCos may include the coefficients of quadratic or higher-order polynomials in pH.

When measurement devices are mass produced, it may not be feasible or practical to individually calibrate each measurement device—i.e. use each individual measurement device to generate individual calibration data. It may be more cost effective to select one or more test devices from a batch of mass produced devices, generate calibration data using the one or more test devices, and provide that calibration data to each individual devices produced in the batch. In some embodiments, variability between measurement devices from the same production batch may be, to a large extent, attributable to a particular part of the measurement device. In particular, variability between devices may be attributable to the part of the measurement device which generates a signal indicative of analyte concentration—e.g. the analyte sensing element—and/or the part of the measurement device that generates a signal indicative of pH—e.g. the pH sensing element. In these circumstances, as well as others, it may be advantageous to use a calibration method employing multiple test measurement devices, and/or multiple test sensing elements, because calibration over multiple test devices and/or sensing elements may yield more accurate calibration data than calibration methods which only utilize a single test device and/or sensing element. Accordingly, in some embodiments, the calibration method may further include selecting a second test analyte sensing element; generating a third set of at least three signals using the second test analyte sensing element, each signal indicative of the concentration of analyte in a different solution of known analyte concentration at the first pH (pH1); and generating a fourth set of at least three signals using the second test analyte sensing element, each signal indicative of the concentration of analyte in a different solution of known analyte concentration at the second pH (pH2). Obviously, calibration methods may similarly employ more than two test devices, or more particularly, for instance, more than two test analyte sensing elements.

In a manner similar to methods utilizing a single test analyte sensing element, after the solutions having known analyte concentrations have been measured and the first, second, third, and fourth sets of at least three signals have been generated, in some embodiments, the sets of signals are used to determine (usually approximately) the relationship between one or more of the Michaelis-Menten parameters and pH. For example, in some embodiments, the pH calibration method may further include (1) computing values of each of a first, second, and third Michaelis-Menten parameter at the first pH ($a_{pH1}$, $b_{pH1}$, and $c_{pH1}$) by an algorithm comprising fitting a modified Michaelis-Menten equation to a first fit dataset comprising both the first set of at least three signals (which was generated with the first test analyte sensing element at pH1) and the third set of at least three signals (which was generated with the second test analyte sensing element at pH1); and (2) computing values of each of a first, second, and third Michaelis-Menten parameter at the second pH ($a_{pH2}$, $b_{pH2}$, and $c_{pH2}$) by an algorithm comprising fitting a modified Michaelis-Menten equation to a second fit dataset comprising both the second set of at least three signals (which was generated with the first test analyte sensing element at pH2) and fourth set of at least three signals (which was generated with the second test analyte sensing element at pH2). Essentially, in these types of methods, the signals generated with the second test analyte sensing element are used in a combined fit with the signals generated with the first test analyte sensing element, which results in values for each of the first, second, and third Michaelis-Menten parameters which take both test analyte sensing elements into account. Alternatively, in some embodiments, a pH calibration method may take both test analyte sensing elements into account by fitting the signals generated from each test analyte sensing element separately, and then averaging the results to obtain better estimates of the Michaelis-Menten parameters. Thus, in some embodiments, the step of computing values of each of a first, second, and third Michaelis-Menten parameter at the first pH ($a_{pH1}$, $b_{pH1}$, and $c_{pH1}$) by an algorithm may further include fitting a modified Michaelis-Menten equation to a third fit dataset comprising the third set of at least three signals, and averaging the results of fitting the third fit dataset with the results of fitting the first fit dataset. In addition, the step of computing values of each of a first, second, and third Michaelis-Menten parameter at the second pH ($a_{pH2}$, $b_{pH2}$, and $c_{pH2}$) by an algorithm may further include fitting a modified Michaelis-Menten equation to a fourth fit dataset comprising the fourth set of at least three signals, and averaging the results of fitting the fourth fit dataset with the results of fitting the second fit dataset.

Other methods for estimating analyte concentration which incorporate pH correction features and pH calibration steps are also disclosed herein. In some embodiments, these methods are similar to those already described above and incorporate similar features, however, additional features may also be disclosed and, in some embodiments, the disclosed methods may be more general and described in more general terms. Since there are many ways to feasibly implement the discoveries disclosed herein for use in estimating analyte concentration, the following additional methods are described in order to illustrate the breadth of implementations that are possible.

In some embodiments, for instance, a method of estimating an analyte concentration from a signal indicative of the analyte concentration may include transforming the signal using an equation of the form of a modified Michaelis-Menten equation wherein the values of one or more Michaelis-Menten parameters have been adjusted for pH.

In some embodiments, for instance, a method of estimating an analyte concentration may include generating a signal indicative of the analyte concentration and generating a signal indicative of a pH, and transforming the signal indicative of the analyte concentration utilizing an equation of the form of a modified Michaelis-Menten equation wherein at least one of the Michaelis-Menten parameters has been substituted with a calibration equation functionally depending on a set of one or more pH calibration parameters and the signal indicative of pH. One could refer to such an equation as a "substituted" modified Michaelis-Menten equation since the Michaelis-Menten parameters have been explicitly substituted with equations depending on one or more other variables—pH and the pH calibration parameters. However, although such a "substituted" equation exhibits a more complicated analytic form, it nevertheless will still express the basic functional relationships of the modified Michaelis-Menten equation.

In some embodiments, the step of transforming the signal indicative of analyte concentration may utilize a "substituted" modified Michaelis-Menten equation in which each of the first, second, and third Michaelis-Menten parameters have been substituted with first, second, and third calibration equations (respectively), each of the equations depending on sets of first, second, and third pH calibration parameters (respectively), and each also depending on the signal indicative of pH. In certain embodiments, at least one of the first, second, and third calibration equations is a polynomial in the signal indicative of pH. In certain such embodiments, each of the first, second, and third calibration equations is a polynomial in the signal indicative of pH. In certain embodiments, at least one of the first, second, and third calibration equations is a linear equation in the signal indicative of pH. In certain such embodiments, the first and second calibration equations are a linear equations in the signal indicative of pH, and the third calibration equation comprises a fraction wherein the numerator is equal to an exponential function of an equation linear in the inverse of the signal indicative of pH, and the denominator is equal to an exponential function of the same linear function in the inverse of the signal indicative of pH evaluated at fixed pH.

Thus, for example, if each Michaelis-Menten parameter of Equation 13 above is assumed to exhibit a linear relationship with pH, then the "substituted" modified Michaelis-Menten equation might appear as $$[Glu] = \frac{\lfloor G_i - (\chi_{a_{pH},1} \cdot \text{pH} + \chi_{a_{pH},0}) \rfloor (\chi_{c_{pH},1} \cdot \text{pH} + \chi_{c_{pH},0}) *}{(\chi_{a_{pH},1} \cdot \text{pH} + \chi_{a_{pH},0}) + (\chi_{b_{pH},1} \cdot \text{pH} + \chi_{b_{pH},0}) - G_i} \quad \text{(Equation 16)}$$

and, similarly, if each Michaelis-Menten parameter is assumed to exhibit a quadratic relationship with pH then the "substituted" modified Michaelis-Menten equation might appear as $$[Glu] = \frac{\lfloor G_i - (\chi_{a_{pH},2} \cdot \text{pH}^2 + \chi_{a_{pH},1} \cdot \text{pH} + \chi_{a_{pH},0}) \rfloor (\chi_{c_{pH},2} \cdot \text{pH}^2 + \chi_{c_{pH},1} \cdot \text{pH} + \chi_{c_{pH},0}) *}{(\chi_{a_{pH},2} \cdot \text{pH}^2 + \chi_{a_{pH},1} \cdot \text{pH} + \chi_{a_{pH},0}) + (\chi_{b_{pH},2} \cdot \text{pH}^2 + \chi_{b_{pH},1} \cdot \text{pH} + \chi_{b_{pH},0}) - G_i} \quad \text{(Equation 17)}$$

where:
[Glu] is the estimated glucose concentration, $\chi_{a_{pH},2}$, $\chi_{a_{pH},1}$, and $\chi_{a_{pH},0}$ are polynomial coefficients parameterizing $a_{pH}$'s dependence on the pH level, $\chi_{b_{pH},2}$, $\chi_{b_{pH},1}$, and $\chi_{b_{pH},0}$ are polynomial coefficients parameterizing $b_{pH}$'s dependence on the pH level, $\chi_{c_{pH},2}$, $\chi_{c_{pH},1}$, and $\chi_{c_{pH},0}$ are polynomial coefficients parameterizing $c_{pH}$'s dependence on the pH level, and $G_i$ is the fluorescent signal (i=1,2), either referenced or unreferenced, where $G_1$ is the fluorescence emission at 550 nm when the fluorophore is excited at 470 nm (which is the absorption maximum of the fluorophore's base-form), and $G_2$ is the fluorescence emission at 550 nm when the fluorophore is excited at 420 nm (which is the absorption maximum of the fluorophore's acid-form). Note, however, that other combinations of excitation and emission wavelengths are also feasible for use in Equations 16 and 17.

As stated above, although, the "substituted" equations (Equations 16 and 17) exhibit a more complicated analytic form, they nevertheless still exhibit the basic functional relationships of the modified Michaelis-Menten equation (Equation 13). In other embodiments, the calibration equations substituted into the modified Michaelis-Menten equation may have a functional form other than a polynomial in pH.

Thus, as described above, the calibration equations substituted into the modified Michaelis-Menten equation for the Michaelis-Menten parameters may take a variety of functional forms and each may have varying numbers of pH calibration parameters. Obviously, more complicated equations may have a greater numbers of pH calibration parameters. In any event, depending on the embodiment, various pH calibration methods may be used to determine the values of the first, second, and third sets of the one or more pH calibration parameters. In certain such embodiments, each set of pH calibration parameters may be determined by fitting the "substituted" modified Michaelis-Menten equation to a plurality of signals, the plurality of signals indicative of analyte concentration in a plurality of solutions at a plurality of pHs. Once values of the various pH calibration parameters are determined, pH corrected estimates of analyte concentrations may be generated from signals indicative of analyte concentration and pH.

EXAMPLE 4

This example concerns the pH calibration of an equilibrium fluorescence glucose GluCath sensor. Again, the GluCath sensor employs an HPTS-Cys-MA dye operably coupled to a 3,3'-oBBV quencher, with the dye and quencher immobilized within a hydrogel disposed along the distal region of an optical fiber, while the proximal end of the optical fiber is coupled to a light source. The pH dependence of this sensor's fluorescence response to glucose was assumed to approximately follow the modified Michaelis-Menten equation labeled as Equation 13 and described above. The Michaelis-Menten $a_{pH}$, $b_{pH}$, and $c_{pH}$ parameters were assumed to bear the relationships to pH set forth in Equations 14 and 15 above. Thus, the $a_{pH}$ and $b_{pH}$ Michaelis-Menten parameters were assumed to depend linearly on pH, while the $c_{pH}$ Michaelis-Menten parameter was assumed to obey an exponential relationship to the inverse of pH as set forth in Equation 14's expression for $c_{pH}$ and Equation 15's expression for $\rho_{c_{pH}}(pH)$. Using this model of the glucose sensor's pH dependence, the pH calibration coefficients, $m_{a_{pH}}$, $\beta_{a_{pH}}$, $m_{b_{pH}}$, $\beta_{b_{pH}}$, $m_{c_{pH}}$, and $\beta_{c_{pH}}$, and $\beta_{c_{pH}}$, were determined by the methodology described above in reference to Equations 14 and 15.

Figure 22:
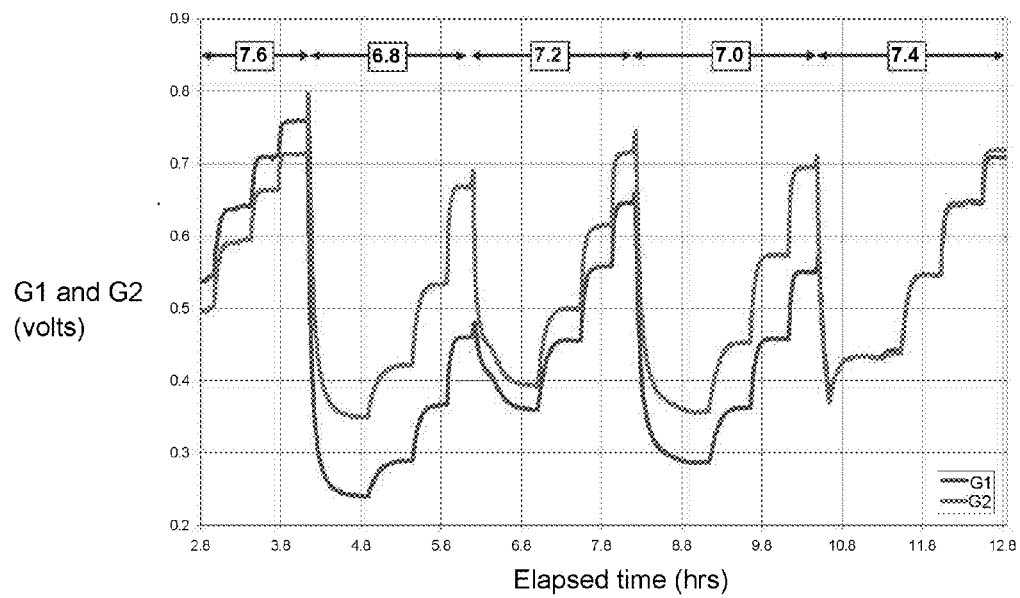
FIG. 22 displays plots of two fluorescent signals at five pH levels and four glucose concentrations.
Figure 23:
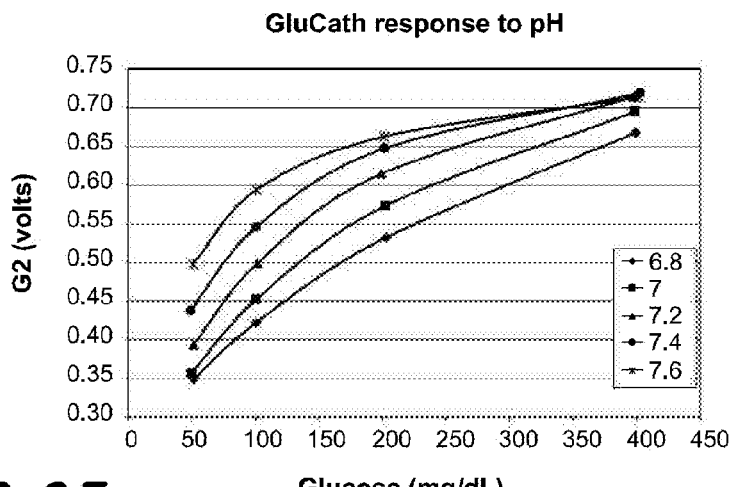
FIG. 23 displays plots of fluorescent signal versus glucose concentration at five pH levels.
Figure 24:
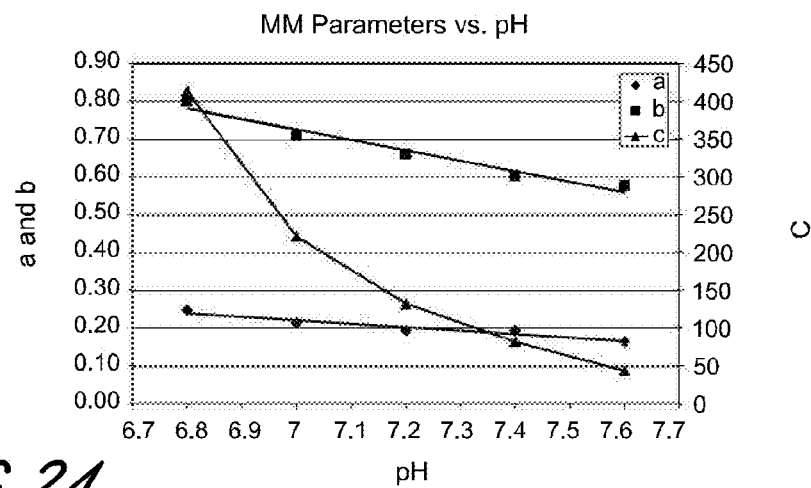
FIG. 24 displays plots of the values of the three Michaelis-Menten parameters versus pH.
Figure 25:
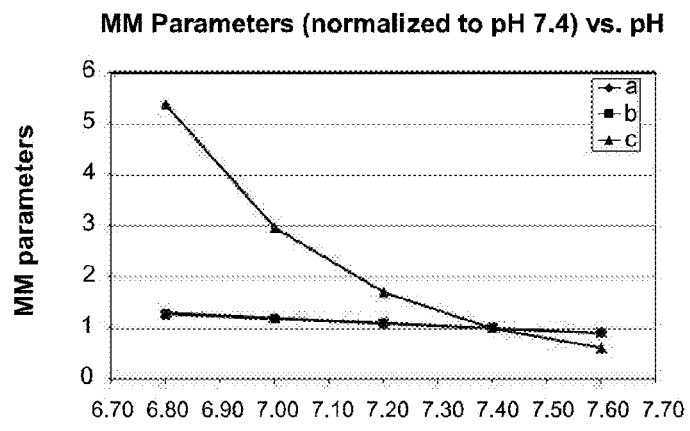
FIG. 25 displays plots of normalized values of the three Michaelis-Menten parameters versus pH.

Specifically, the effect of pH on the fluorescent signal was determined experimentally by measuring the signal at five pH levels (6.8, 7.0, 7.2, 7.4, and 7.6) and four glucose concentrations (50 mg/dL, 100 mg/dL, 200 mg/dL, and 400 mg/dL). At each pH and glucose level, the stable fluorescent signals $G_1$ and $G_2$ were recorded, as displayed in FIG. 22. FIG. 22 illustrates that the data corresponding to a fixed glucose concentration of 100 mg/dL exhibits the lowest fluorescent intensity at the lowest pH (pH 6.8), and the highest fluorescent intensity at the highest pH (pH 7.6)—and, more generally, that the intensity increases monotonically as a function of pH. However, the modulation due to glucose changes inversely with pH—that is, the modulation (the ratio of fluorescent intensity at high glucose concentration versus low glucose concentration) is lowest at high pH and highest at low pH. Values of the stable fluorescent signal G2 taken from FIG. 22 are replotted in FIG. 23 versus glucose concentration—each curve corresponding to a fixed pH level. Since the five constant-pH curves in FIG. 23 are generally non-overlapping, it is clear that changes in pH level have an effect on the G2 fluorescent signal. From this data, values of the Michaelis-Menten parameters, $a_{pH}$, and $c_{pH}$ (specifically, $a_{6.8}$, $a_{7.0}$, $a_{7.2}$, $a_{7.4}$, $a_{7.6}$, $b_{6.8}$, $b_{7.0}$, $b_{7.2}$, $b_{7.4}$, $b_{7.6}$, $c_{6.8}$, $c_{7.0}$, $c_{7.2}$, $c_{7.4}$, and $c_{7.6}$), were computed using Equation 13, see FIG. 24, and normalized to their values at pH 7.4, see FIG. 25. FIGS. 24 and 25 illustrate that values of the first and second Michaelis-Menten parameters, $a_{pH}$ and $b_{pH}$, respectively, vary approximately linearly with pH level, while the value of the third Michaelis-Menten parameter, $c_{pH}$, exhibits some degree of non-linear variation with pH. Hence, Equations 14 and 15 were chosen to model $a_{pH}$, $b_{pH}$, and $c_{pH}$, as described above.

This process for determining values of $a_{pH}$, $b_{pH}$, and $c_{pH}$ was repeated over two additional glucose sensors of the same design as the first to generate a calibration with improved accuracy. Thus, fluorescent signals were generated with each of the two additional glucose sensors, at each of the same five pH levels (6.8, 7.0, 7.2, 7.4, and 7.6) and four glucose concentrations (50 mg/dL, 100 mg/dL, 200 mg/dL, and 400 mg/dL). This data corresponding to each of the two additional glucose sensors was fit with Equations 14 and 15 (as was done with the initial sensor) in order to generate values of $a_{6.8}$, $a_{7.0}$, $a_{7.2}$, $a_{7.4}$, $a_{7.6}$, $b_{6.8}$, $b_{7.0}$, $b_{7.2}$, $b_{7.4}$, $b_{7.6}$, $c_{6.8}$, $c_{7.0}$, $c_{7.2}$, $c_{7.4}$, and $c_{7.6}$ for each additional glucose sensor. The data from the additional two glucose sensors was averaged together with the data from the first sensor to generate averaged values of the Michaelis-Menten parameters, $\bar{a}_{6.8}$, $\bar{a}_{7.0}$, $\bar{a}_{7.2}$, $\bar{a}_{7.4}$, $\bar{a}_{7.6}$, $\bar{b}_{6.8}$, $\bar{b}_{7.0}$, $\bar{b}_{7.2}$, $\bar{b}_{7.4}$, $\bar{b}_{7.6}$, $\bar{c}_{6.8}$, $\bar{c}_{7.0}$, $\bar{c}_{7.2}$, $\bar{c}_{7.4}$, and $\bar{c}_{7.6}$.

Determination of the pH calibration parameters corresponding to Equations 14 and 15 was done using these averaged values. Thus, the pH calibration parameters corresponding to the "a" Michaelis-Menten parameter—i.e. $m_{a_{pH}}$ and $\beta_{a_{pH}}$—were determined by normalizing each of the "a" parameters to $\bar{a}_{7.4}$, and fitting a line (again using linear least squares) to a plot of these values—i.e. $\bar{a}_{6.8}/\bar{a}_{7.4}$, $\bar{a}_{7.0}/\bar{a}_{7.4}$, $\bar{a}_{7.2}/\bar{a}_{7.4}$, 1, $\bar{a}_{7.6}/\bar{a}_{7.4}$ versus pH—the slope and intercept being $m_a$ and $\beta_a$, respectively. The same was done with the pH calibration parameters $m_{b_{pH}}$ and $\beta_{b_{pH}}$, corresponding to the "b" Michaelis-Menten parameter, and $m_{c_{pH}}$ and $\beta_{c_{pH}}$, corresponding to the "c" Michaelis-Menten parameter. The resulting empirically derived values for these pH calibration coefficients (pHCos) are summarized in Table 5 below:

TABLE 5

| | |
|---|---|
| $m_{a_{pH}} = -0.49736$ | $\beta_{a_{pH}} = 4.6805$ |
| $m_{b_{pH}} = -0.45178$ | $\beta_{b_{pH}} = 4.3432$ |
| $m_{c_{pH}} = 141.06$ | $\beta_{c_{pH}} = -14.7229$ |

Methods of Estimating Analyte Concentration Incorporating Temperature and pH Correction In the preceding disclosure, various methods and/or algorithms are described for correcting a signal indicative of analyte concentration, independently for the effects of temperature, and independently for the effects of pH. It has also been discovered that various aspects of these methods and/or algorithms may be incorporated into combination algorithms and/or methods which correct for both the pH and temperature dependence of signals indicative of analyte concentration. Similarly to what was discovered with respect to correction for temperature and pH level, it has been found that a modified Michaelis-Menten equation can also be used as an analytical model to take both temperature and pH dependence into account simultaneously. Thus, temperature and pH dependence may be modeled in combination with an equation analogous to Equations 1 and 13 described above:

$$[Glu] = \frac{c_{T,pH} * \lfloor G_i - a_{T,pH} \rfloor}{a_{T,pH} + b_{T,pH} - G_i} \quad \text{(Equation 18)}$$

where:
[Glu] is the estimated glucose concentration,
$a_{T,pH}$ is the first Michaelis-Menten parameter "a", at a particular temperature and pH,
$b_{T,pH}$ is the second Michaelis-Menten parameter "b", at the same particular temperature and pH,
$c_{T,pH}$ is the third Michaelis-Menten parameter "c", at the same particular temperature and pH, and
$G_i$ is the fluorescent signal (i=1,2), either referenced or unreferenced, where $G_1$ is the fluorescence emission at 550 nm when the fluorophore is excited at 470 nm (which is the absorption maximum of the fluorophore's base-form), and $G_2$ is the fluorescence emission at 550 nm when the fluorophore is excited at 420 nm (which is the absorption maximum of the fluorophore's acid-form). Note, however, that other combinations of excitation and emission wavelengths are also feasible for use in Equation 18. In the Examples below, $G_2$ has been used, unless indicated otherwise.

Accordingly, some embodiment methods of estimating an analyte concentration include generating a signal indicative of the analyte concentration, a signal indicative of a temperature, and a signal indicative of a pH. In some embodiments, the signal indicative of the analyte concentration and the signal indicative of the pH are both generated from a set of at least two signals each of which is indicative of both the pH and the analyte concentration. For instance, these could be the $G_1$ and $G_2$ fluorescent signals described above, both of which are indicative of both analyte concentration and pH. In some embodiments, the $G_2$ fluorescent signal itself may be treated as the signal indicative of analyte concentration, while $G_1$ and $G_2$ are used as signals indicative of pH, for example, in the pH determination algorithm described above. Furthermore, in some embodiments, the signal indicative of the analyte concentration, the signal indicative of the temperature, and the signal indicative of the pH are each generated from a set of at least three signals each of which is indicative of the temperature, the pH, and the analyte concentration. Since, in some embodiments, the signal indicative of the analyte concentration exhibits a temperature dependence and a pH dependence which may be quantitatively characterized by a modified Michaelis-Menten equation (as described above), methods accomplishing temperature and pH correction may further include transforming the signal indicative of the analyte concentration utilizing an equation of the form of a modified Michaelis-Menten equation, such as Equation 18 above, depending on Michaelis-Menten parameters, such as the parameters "a", "b", and "c", as described above as first, second, and third Michaelis-Menten parameters with reference to Equation 18.

The temperature and pH dependence of Equation 18 is exhibited through the Michaelis-Menten parameters $a_{T,pH}$, $b_{T,pH}$, and $c_{T,pH}$, as indicated by the subscripts "T" and "pH" labeling these parameters. In some embodiments, the temperature and pH dependence may need to be determined through a calibration method. Thus, in certain embodiment methods, the values of one or more of the Michaelis-Menten parameters may be set based on data which includes temperature and pH calibration parameters, the signal indicative of temperature, and the signal indicative of a pH.

In some embodiment methods, the temperature and pH calibration parameters may be determined by a calibration method. The calibration method may include selecting a first test analyte sensing element, selecting three differing concentrations of analyte, selecting a first temperature (T1) and a second temperature (T2) (the second differing from the first), and selecting a first pH (pH1) and a second pH (pH2) (the second differing from the first). Once these selections are made, the calibration method may include computing values of each of a first, second, and third Michaelis-Menten parameter at the selected first temperature (T1). This computation may employ an algorithm which includes fitting a modified Michaelis-Menten equation to at least three signals indicative of the selected three differing concentrations of analyte in solution at the selected first temperature (T1). The three signals may be generated, for example, by using the first test analyte sensing element to measure the concentration of analyte in each solution of a set of three solutions, each of which has been prepared so as to contain one of the three selected concentrations of analyte adjusted to the first selected temperature (T1).

Calculations are then performed with respect to the selected second temperature (T2), analogously to those employed with respect to the selected first temperature (T1). Thus, the calibration method may include computing values of each of a first, second, and third Michaelis-Menten parameter at the selected second temperature (T2). This computation may employ an algorithm which includes fitting a modified Michaelis-Menten equation to at least three signals indicative of the selected three differing concentrations of analyte in solution at the selected second temperature (T2). The three signals may be generated, for example, by using the first test analyte sensing element to measure the concentration of analyte in each solution of a set of three solutions, each of which has been prepared so as to contain one of the three selected concentrations of analyte adjusted to the second selected temperature (T2).

To account for pH effects, the calibration method may include computing values of each of a first, second, and third Michaelis-Menten parameter at the selected first pH level (pH1) and the selected second pH level (pH2). The computation with respect to the selected first pH level (pH1) may employ an algorithm which includes fitting a modified Michaelis-Menten equation to at least three signals indicative of the selected three differing concentrations of analyte in solution at the selected first pH level (pH1). The three signals may be generated, for example, by using the first test analyte sensing element to measure the concentration of analyte in each solution of a set of three solutions, each of which has been prepared so as to contain one of the three selected concentrations of analyte adjusted to the first selected pH level (pH1). Similarly, the computation with respect to the selected second pH level (pH2) may employ an algorithm which includes fitting a modified Michaelis-Menten equation to at least three signals indicative of the selected three differing concentrations of analyte in solution at the selected second pH level (pH2). The three signals may be generated, for example, by using the second test analyte sensing element to measure the concentration of analyte in each solution of a set of three solutions, each of which has been prepared so as to contain one of the three selected concentrations of analyte adjusted to the second selected pH level (pH2).

Note that though the above described computation uses three selected analyte concentrations to compute values of the first, second, and third Michaelis-Menten parameters at two temperatures and two pH levels, one of ordinary skill in the art will readily appreciate that more than three selected concentrations may be also be used. Generally, employing greater numbers of selected analyte concentrations will produce more accurate values of the Michaelis-Menten parameters at the various temperatures and pH levels. Furthermore, in some embodiments, it may be advantageous to compute the first, second, and third Michaelis-Menten parameters at more than two temperatures and more than two pH levels, as will become apparent to one of ordinary skill in the art from the discussion that follows.

From values of the first, second, and third Michaelis-Menten parameters at two or more temperatures ($a_{T1}$, $b_{T1}$, $c_{T1}$, $a_{T2}$, $b_{T2}$, and $c_{T2}$) and two or more pH levels ($a_{pH1}$, $b_{pH1}$, $c_{pH1}$, $a_{pH2}$, $b_{pH2}$, and $c_{pH2}$), a relationship between each Michaelis-Menten parameter and temperature and pH may be determined. Thus, in some embodiments, a first calibration equation is selected to relate the first Michaelis-Menten parameter to temperature and pH. In some embodiments, the equation may depend on a first set of temperature and pH calibration parameters. In certain such embodiments, a value for each parameter is set based on the values of the first Michaelis-Menten parameter at the first temperature ($a_{T1}$), the second temperature ($a_{T2}$), the first pH ($a_{pH1}$), and the second pH ($a_{pH2}$). Similarly, in some embodiments, a second calibration equation is selected to relate the second Michaelis-Menten parameter to temperature and pH. In some embodiments, the equation may depend on a second set of temperature and pH calibration parameters. In certain such embodiments, a value for each parameter is set based on the values of the second Michaelis-Menten parameter at the first temperature ($b_{T1}$), the second temperature ($b_{T2}$), the first pH ($b_{pH1}$), and the second pH ($b_{pH2}$). Finally, in some embodiments, a third calibration equation is selected to relate the third Michaelis-Menten parameter to temperature and pH. In some embodiments, the equation may depend on a third set of temperature and pH calibration parameters. In certain such embodiments, a value for each parameter is set based on the values of the third Michaelis-Menten parameter at the first temperature ($c_{T1}$), the second temperature ($c_{T2}$), the first pH ($c_{pH1}$), and the second pH ($c_{pH2}$).

A calibration equation which is selected to relate one of the Michaelis-Menten parameters to temperature and pH may consist of any functional relationship which satisfactorily relates the parameter to temperature and pH once the equation's calibration parameters (if any) are determined. Suitable calibration equations include analytic functions such as polynomial functions in temperature and pH. However, the phrase "calibration equation" is used herein to generally denote any functional relationship between one of the Michaelis-Menten parameters and temperature and pH. Thus, for example, a lookup table specifying a value of any Michaelis-Menten parameter based on particular values of temperature and pH is considered a "calibration equation" as that phrase is used herein. A set of multiple analytic functions which individually apply over particular ranges of temperatures and pHs is also considered a "calibration equation" as that phrase is used herein.

In some calibration methods, the first calibration equation (i.e. selected to relate the first Michaelis-Menten parameter to temperature and pH) comprises a product of a first pH-independent function and a first temperature-independent function. One of ordinary skill in the art will readily appreciate that, in some embodiments, using functions which satisfy this criteria may simplify the analysis somewhat, however, such a person of ordinary skill would also appreciate that such a criteria is not essential to the operation of the general methods disclosed herein. The same criteria may also apply to the second and third calibration equations. Thus, in some embodiments, the second calibration equation is the product of a second pH-independent function and a second temperature-independent function, and the third calibration equation is the product of a third pH-independent function and a third temperature-independent function. In some embodiments, calibration equations meeting these criteria may be represented by the following expression:

$$a_{T,pH} = a_0 * \tau_{a_T}(T) * \rho_{a_{pH}}(\text{pH}),$$

$$b_{T,pH} = b_0 * \tau_{b_T}(T) * \rho_{b_{pH}}(\text{pH}),$$

$$c_{T,pH} = b_0 * \tau_{c_T}(T) * \rho_{c_{pH}}(\text{pH}), \quad \text{(Equation 19)}$$

where:

$\tau_{a_T}(T)$, $\tau_{b_T}(T)$, and $\tau_{c_T}(T)$ are "temperature correction factors" which approximately account for the temperature dependence of $a_{T,pH}$, $b_{T,pH}$, and $c_{T,pH}$;

$\rho_{a_{pH}}(\text{pH})$, $\rho_{b_{pH}}(\text{pH})$, and $\rho_{c_{pH}}(\text{pH})$ are "pH correction factors" which approximately account for the pH dependence of $a_{T,pH}$, $b_{T,pH}$, and $c_{T,pH}$; and $a_0$, $b_0$, $c_0$ are constants set equal to the value of $a_{T,pH}$, $b_{T,pH}$, and $c_{T,pH}$ determined at a particular selected standard temperature and pH level.

When the temperature and pH dependence of each Michaelis-Menten parameter is expressed in the form of Equation 19, each Michaelis-Menten parameter, $a_{T,pH}$, $b_{T,pH}$, $c_{T,pH}$, is determined by multiplying its value at the selected standard temperature and pH level, $a_0$, $b_0$, $c_0$, by its corresponding "temperature correction factor," $\tau_{a_T}(T)$, $\tau_{b_T}(T)$, $\tau_{c_T}(T)$, and by multiplying again by its corresponding "pH correction factor," $\rho_{a_{pH}}(\text{pH})$, $\rho_{b_{pH}}(\text{pH})$, $\rho_{c_{pH}}(\text{pH})$ (of course, the order of multiplication is irrelevant when the temperature and pH dependence are modeled in this manner). The standard temperature and pH Michaelis-Menten parameters, $a_0$, $b_0$, $c_0$, may be determined by fitting a modified Michaelis-Menten equation to a set of signals indicative of the analyte concentration of a plurality of solutions of differing analyte concentrations held at the selected standard temperature and pH level. Alternatively, the parameters $a_0$, $b_0$, and $c_0$ may be supplied by a factory calibration as described in provisional U.S. patent application No. 61/184,747, "Algorithms for Calibrating an Analyte Sensor," filed Jun. 5, 2009, which is hereby incorporated herein by reference in its entirety. As yet another alternative, $a_0$, $b_0$, and $c_0$ may be determine via a one-point in vivo calibration as also disclosed in the same application.

Furthermore, in some embodiments, the first, second, and third pH-independent functions may be selected so as to be linear in temperature; the first and second temperature-independent functions may be selected so as to be linear in pH; and the third temperature-independent function may be selected to be a fraction wherein the numerator is equal to an exponential function of a third function linear in the inverse of pH, and the denominator is equal to an exponential function of the same function linear in the inverse of pH evaluated at pH 7.4. Calibration equations satisfying these criteria may be written as:

$$\tau_{a_T}(T) = m_{a_T} * T + \beta_{a_T}, \quad \text{(Equation 3)}$$

$$\tau_{b_T}(T) = m_{b_T} * T + \beta_{b_T},$$

$$\tau_{c_T}(T) = m_{c_T} * T + \beta_{c_T},$$

$$\rho_{a_{pH}}(\text{pH}) = m_{a_{pH}} * \text{pH} + \beta_{a_{pH}}, \quad \text{(Equation 15)}$$

$$\rho_{b_{pH}}(\text{pH}) = m_{b_{pH}} * \text{pH} + \beta_{b_{pH}}, \text{ and}$$

$$\rho_{c_{pH}}(\text{pH}) = \frac{e^{\left(\frac{m_{c_{pH}}}{\text{pH}} + \beta_{c_{pH}}\right)}}{e^{\left(\frac{m_{c_{pH}}}{7.4} + \beta_{c_{pH}}\right)}}.$$

These equations, as indicated by their numbering, are identical to the equations discussed above with respect to separate temperature calibration and pH calibration. Thus, in methods employing these equations, the first set of temperature and pH calibration parameters comprise the slope and intercept of the first pH-independent function and the slope and intercept of the first temperature independent function. Similarly, the second set of temperature and pH calibration parameters comprise the slope and intercept of the second pH-independent function and the slope and intercept of the second temperature independent function, and the third set of temperature and pH calibration parameters comprise the slope and intercept of the third pH-independent function and the slope and intercept of the third function linear in the signal indicative of pH.

Since the calibration equations selected to represent the temperature and pH correction factors match those separately employed above with respect to temperature and pH correction, the TempCos ($m_{a_T}$, $\beta_{a_T}$, $m_{b_T}$, $\beta_{b_T}$, $m_{c_T}$, and $\beta_{c_T}$) and pHCos ($m_{a_{pH}}$, $\beta_{a_{pH}}$, $m_{b_{pH}}$, $\beta_{b_{pH}}$, $m_{c_{pH}}$, and $\beta_{c_{pH}}$) determined above separately with respect to temperature and pH may be used in Equation 19, provided that $a_0$, $b_0$, and $b_0$ are determined in a manner consistent with the determination of the 37° C. Michaelis-Menten parameters, $a_{37}$, $b_{37}$, $c_{37}$, and the pH 7.4 Michaelis-Menten parameters, $a_{7.4}$, $b_{7.4}$, $c_{7.4}$. For instance, if $a_0$, $b_0$, and $c_0$ are determined at 37° C. and pH 7.4, then these constants may be consistently relabeled $a_{37,7.4}$, $b_{37,7.4}$, and $c_{37,7.4}$, and the TempCos and pHCos determined above separately with respect to temperature and pH may be used in Equation 19. Therefore, an expression for computing a temperature and pH corrected glucose concentration may be given by $$[Glu] = \frac{\lfloor G_2 - a_{37,7.4} * \tau_{a_T}(T) * \rho_{a_{pH}}(\text{pH}) \rfloor}{a_{37,7.4} * \tau_{a_T}(T) * \rho_{a_{pH}}(\text{pH}) +} \quad \text{(Equation 20)}$$
$$b_{37,7.4} * \tau_{c_T}(T) * \rho_{c_{pH}}(\text{pH}) *$$
$$b_{37,7.4} * \tau_{b_T}(T) * \rho_{b_{pH}}(\text{pH}) - G_2$$

where:
[Glu] is the estimated glucose concentration,
$a_{T,pH}$, $b_{T,pH}$, and $c_{T,pH}$ are the Michaelis-Menten parameters, at a particular temperature and pH,
$a_{37,7.4}$, $b_{37,7.4}$ and $c_{37,7.4}$ are the Michaelis-Menten parameters determined at 37° C. and pH 7.4,
$\tau_{a_T}(T)$, $\tau_{b_T}(T)$, $\tau_{c_T}(T)$, $\rho_{a_{pH}}(\text{pH})$, $\rho_{b_{pH}}(\text{pH})$, and $\rho_{c_{pH}}(\text{pH})$ are given by Equations 3 and 15, and
$G_2$ is the fluorescent emission, either referenced or unreferenced, at 550 nm when the fluorophore is excited at 420 nm (which is the absorption maximum of the fluorophore's acid-form). Note, however, that other combinations of excitation and emission wavelengths are also feasible for use in Equation 20. In Example 5 below, $G_2$ has been used.

EXAMPLE 5

This example concerns the simultaneous temperature and pH calibration of an equilibrium fluorescence glucose GluCath sensor, and an assessment of the accuracy of the calibration by comparison with an independent data set. Again, the GluCath sensor employs an HPTS-Cys-MA dye operably coupled to a 3,3'-oBBV quencher, with the dye and quencher immobilized within a hydrogel disposed along the distal region of an optical fiber, while the proximal end of the optical fiber is coupled to a light source. The temperature and pH dependence of this sensor's fluorescence response to glucose was assumed to approximately follow Equation 20—using the TempCos from Table 2 and the pHCos from Table 5. The 37° C., pH 7.4 Michaelis-Menten parameters, $a_{37,7.4}$, $b_{37,7.4}$, $c_{37,7.4}$, appearing in Equation 20 were determined by averaging data over multiple sensors derived from fitting a modified Michaelis-Menten equation to three solutions having known glucose concentrations of 0 mg/dL, 100 mg/dL, and 400 mg/dL, followed by a single measurement at 100 mg/dL using the individual sensor to adjust the parameters to the individual sensor.

Figure 26:
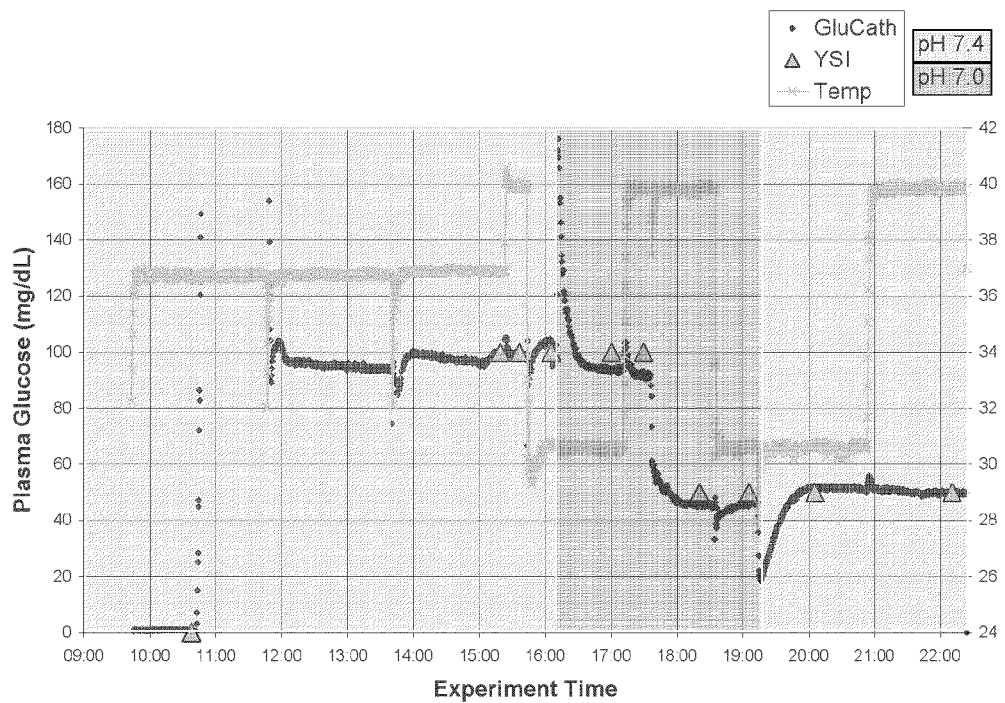
FIG. 26 compares a plot of glucose concentration as determined by reference measurements with a plot of glucose concentration as determined by one embodiment of an analyte measuring device ("GluCath") disclosed herein.
Figure 27:
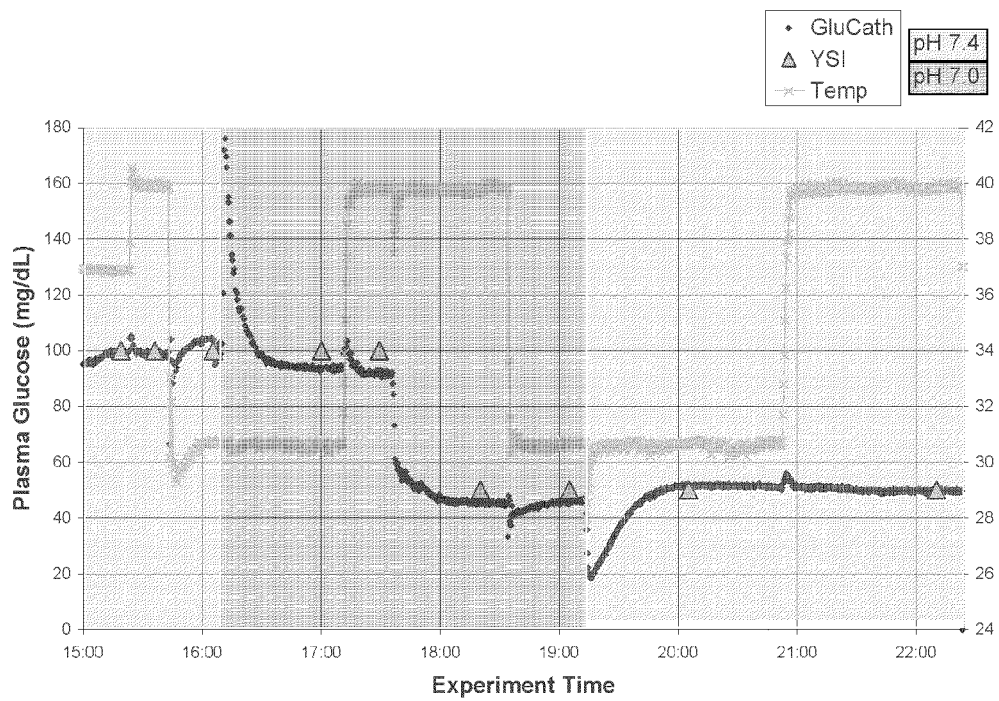
FIG. 27 displays a magnified portion of the plots of FIG. 26.

To test the calibration, measurements were made on two different glucose solution concentrations (50 mg/dL and 100 mg/dL), at two different temperatures (30° C. and 40° C.), and at two different pH levels (pH 7.400 and pH 7.035). Reference measurements were made using the Yellow Springs Instrument glucose oxidase lab analyzer ("YSI"), the gold standard of blood glucose measurements. The results are displayed in FIG. 26, FIG. 27 (which displays a zoomed-in portion of FIG. 26), and Table 6 below. In particular, Table 6 lists the predicted glucose concentration compared to the YSI reference measurements before correction, and after temperature and pH correction using Equation 20. The mean absolute relative deviation ("MARD") between the temperature and pH corrected glucose concentrations and the reference glucose concentration was only 5.0%, while the MARD for the same data set without temperature and pH correction was 29.6%.

TABLE 6

| | | | Uncorrected | | | Temp, pH-corrected | | |
|---|---|---|---|---|---|---|---|---|
| Temp | pH | Glucose | GluCath | Diff. | % Diff. | GluCath | Diff. | % Diff. |
| 40 | 7.400 | 100 | 87.7 | −12.3 | −12.3% | 97.8 | −2.2 | −2.2% |
| 30 | 7.400 | 100 | 133.1 | 33.1 | 33.1% | 103.7 | 3.7 | 3.7% |
| 30 | 7.035 | 100 | 72.2 | −27.8 | −27.8% | 93.5 | −6.5 | −6.5% |
| 40 | 7.035 | 100 | 50.4 | −49.6 | −49.6% | 91.3 | −8.7 | −8.7% |
| 40 | 7.035 | 50 | 25.7 | −24.3 | −48.7% | 46.1 | −3.9 | −7.8% |
| 30 | 7.035 | 50 | 34.7 | −15.3 | −30.7% | 46.4 | −3.6 | −7.2% |
| 30 | 7.400 | 50 | 63.6 | 13.6 | 27.2% | 51.5 | 1.5 | 2.9% |
| 40 | 7.400 | 50 | 46.2 | −3.8 | −7.7% | 50.7 | 0.7 | 1.4% |
| | | | | MARD | 29.6% | | MARD | 5.0% |

Other Related Methods of Incorporating Temperature and pH Correction

Other methods for estimating analyte concentration which incorporate temperature and pH correction features and temperature and pH calibration steps are also disclosed herein. In some embodiments, these methods are similar to those already described above and incorporate similar features, however, additional features may also be disclosed and, in some embodiments, the disclosed methods may be more general and described in more general terms. Since there are many ways to feasibly implement the discoveries disclosed herein for use in estimating analyte concentration, the following additional methods are described in order to illustrate the breadth of implementations that are possible.

In some embodiments, for instance, a method of estimating an analyte concentration from a signal indicative of the analyte concentration may include transforming the signal using an equation of the form of a modified Michaelis-Menten equation wherein the values of one or more Michaelis-Menten parameters have been adjusted for temperature and pH.

In some embodiments, for instance, a method of estimating an analyte concentration of a solution may include generating a signal indicative of the analyte concentration of the solution, generating a signal indicative of a temperature of the solution, generating a signal indicative of a pH of the solution, and transforming the signal indicative of the analyte concentration utilizing an equation of the form of a modified Michaelis-Menten equation wherein at least one of the Michaelis-Menten parameters has been substituted with a calibration equation functionally depending on a set of one or more temperature and pH calibration parameters, the signal indicative of the temperature, and the signal indicative of the pH. One could refer to such an equation as a "substituted" modified Michaelis-Menten equation since the Michaelis-Menten parameters have been explicitly substituted with equations depending on one or more other variables—temperature, pH level, and the temperature and pH calibration parameters. However, although such a "substituted" equation exhibits a more complicated analytic form, it nevertheless will still express the basic functional relationships of the modified Michaelis-Menten equation.

In some embodiments, the step of transforming the signal indicative of analyte concentration may utilize a "substituted" modified Michaelis-Menten equation in which each of the first, second, and third Michaelis-Menten parameters have been substituted with first, second, and third calibration equations (respectively), each of the equations depending on sets of first, second, and third temperature and pH calibration parameters (respectively), and each also depending on the signal indicative of temperature and the signal indicative of pH.

In certain embodiments, the first calibration equation is the product of a first pH-independent polynomial in the signal indicative of temperature and a first temperature-independent polynomial in the signal indicative of pH. Similarly, in certain embodiments, the second calibration equation is the product of a second pH-independent polynomial in the signal indicative of temperature and a second temperature-independent polynomial in the signal indicative of pH; and the third calibration equation is the product of a third pH-independent polynomial in the signal indicative of temperature and a third temperature-independent function of the signal indicative of pH. In certain such embodiments, one or more of the first, second, and third pH-independent polynomials are linear equations in the signal indicative of temperature, and one or more of the first and second temperature-independent polynomials are linear equations in the signal indicative of pH, while the third temperature-independent function is a fraction wherein the numerator is equal to an exponential function of a function linear in the inverse of the signal indicative of pH, and the denominator is equal to an exponential function of the same function linear in the inverse of the signal indicative of pH evaluated at pH 7.4.

Note, that in many if not all of the methods described herein, transforming the signal indicative of analyte concentration using an equation of the form of a modified Michaelis-Menten equation may utilize a look-up table. In some circumstances, function evaluation by use of a look-up table may be more computationally efficient than direct application of the same function as it is written. To illustrate, a function mapping a single input variable to a single output variable, e.g. $y=f(x)$, may be evaluated via a look-up table. In this simple case, the look-up table consists of a set of discrete matching input and output values, e.g. (x, y) pairs. Evaluating the function $f(x)$ or computing the output value y which corresponds to a given input value x, may be accomplished by looking up the input value x in the look-up table, and choosing the output value y in the table which corresponds to it. If the exact input value does not exist in the look-up table, the corresponding output value may be determined by interpolating from the output values in the table whose corresponding input values are similar to the original input value. Such methodology may be more efficient than evaluating a function, when looking up values in the look-up table and interpolating between values when necessary is quicker than applying the function as written to a given input value. However, use of a look-up table should be understood to simply be a potentially efficient way to approximate the application of a function in analytic form. Accordingly, when transformations using equations are described herein, it should be understood that such described transformations encompass the direct application of the equations as well as the use of a look-up table to approximate such transformations. More specifically, it is to be understood that reference herein to the transformation of one or more signals using an equation of the form of a modified Michaelis-Menten equation does encompass transformations utilizing a look-up table.

Thus, as described above, the calibration equations substituted into the modified Michaelis-Menten equation for the Michaelis-Menten parameters may take a variety of functional forms and each may have varying numbers of temperature and pH calibration parameters. Obviously, more complicated equations may have a greater numbers of temperature and pH calibration parameters. In any event, depending on the embodiment, various temperature and pH calibration methods may be used to determine the values of the first, second, and third sets of the one or more temperature and pH calibration parameters. In certain such embodiments, each set of temperature and pH calibration parameters may be determined by fitting the "substituted" modified Michaelis-Menten equation to a plurality of signals, the plurality of signals indicative of analyte concentration in a plurality of solutions having differing analyte concentrations, at a plurality of temperatures, and at a plurality of pH levels. Once values of the various temperature and pH calibration parameters are determined, temperature and pH corrected estimates of analyte concentrations may be generated from signals indicative of analyte concentration, temperature, and pH.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method of estimating glucose concentration in a physiologic fluid comprising:
contacting an optical sensor with the physiological fluid, wherein the optical sensor comprises a non-enzymatic, equilibrium fluorescence chemical indicator system disposed along a distal region of an optical fiber, the chemical indicator system comprising a fluorophore operably coupled to a glucose binding moiety, wherein the fluorophore is configured to generate a fluorescent emission signal upon excitation with light, and wherein glucose binding to the glucose binding moiety causes a change in the fluorescent emission signal related to the glucose concentration of the physiological fluid;

detecting the fluorescent emission signal indicative of the glucose concentration;

contacting a temperature sensing element with the physiological fluid, wherein the temperature sensing element is configured to generate a signal indicative of a temperature of the physiological fluid;

detecting the signal indicative of the physiological fluid temperature;

contacting a pH sensing element with the physiological fluid, wherein the pH sensing element is configured to generate a signal indicative of a pH of the physiological fluid;

detecting the signal indicative of the physiological fluid pH; and transforming the fluorescent emission signal indicative of the glucose concentration utilizing the equation:

$$[Glu] = \frac{c_{T,pH} * \lfloor G_i - a_{T,pH} \rfloor}{a_{T,pH} + b_{T,pH} - G_i},$$

wherein
[Glu] is the glucose concentration,
$G_i$ is the fluorescent emission signal intensity
$a_{T,pH}$ is the fluorescent emission signal intensity in the absence of glucose at a particular temperature and pH,
$b_{T,pH}$ is the asymptotic signal intensity at infinite glucose concentration, minus the fluorescent signal intensity in the absence of glucose ($a_{T,pH}$) at the same particular temperature and pH, and
$c_{T,pH}$ is the glucose concentration at which the fluorescent signal intensity is one-half the difference between the asymptotic ($b_{T,pH}$) and the background ($a_{T,pH}$) at the same particular temperature and pH,
wherein $a_{T,pH}$, $b_{T,pH}$, and $c_{T,pH}$ are set based on data comprising:
  temperature and pH calibration data;
  the detected signal indicative of temperature; and
  the detected signal indicative of pH.

2. The method of claim 1, wherein the chemical indicator system, the temperature sensing element and the pH sensing element are incorporated within a single sensor.

3. The method of claim 1, wherein the fluorescent emission signal indicative of the glucose concentration, the signal indicative of the temperature, and the signal indicative of the pH are each generated from a set of at least three signals each of which is indicative of the temperature, the pH, and the glucose concentration.

4. The method of claim 1, wherein the temperature and pH calibration parameters are determined by a calibration method comprising:
  selecting a first test glucose sensing element;
  selecting three differing concentrations of glucose;
  selecting a first temperature and a second temperature, the second differing from the first;
  selecting a first pH and a second pH, the second differing from the first;
  computing values of each of $a_{T,pH}$, $b_{T,pH}$, and $c_{T,pH}$ at the first temperature by an$_{pH}$ algorithm comprising fitting the equation to at least three signals indicative of the three differing concentrations of glucose in solution at the first temperature, the at least three signals generated using the first test glucose sensing element;
  computing values of each of $a_{T,pH}$, $b_{T,pH}$, and $c_{T,pH}$ at the second temperature by an algorithm comprising fitting the equation to at least three signals indicative of the three differing concentrations of glucose in solution at the second temperature, the at least three signals generated using the first test glucose sensing element;
  computing values of each of $a_{T,pH}$, $b_{T,pH}$, and $c_{T,pH}$ at the first pH by an algorithm comprising fitting the equation to at least three signals indicative of the three differing concentrations of glucose in solution at the first pH, the at least three signals generated using the first test glucose sensing element;
  computing values of each of $a_{T,pH}$, $b_{T,pH}$, and $c_{T,pH}$ at the second pH by an algorithm comprising fitting the equation to at least three signals indicative of the three differing concentrations of glucose in solution at the second pH, the at least three signals generated using the first test glucose sensing element;
  selecting a first calibration equation relating $a_{T,pH}$ to temperature and pH, the equation depending on a first set of the temperature and pH calibration parameters, and setting a value for each parameter based on the values of $a_{T,pH}$ at the first temperature, the second temperature, the first pH, and the second pH;
  selecting a second calibration equation relating $b_{T,pH}$ to temperature and pH, the equation depending on a second set of the temperature and pH calibration parameters, and setting a value for each parameter based on the values of $b_{T,pH}$ at the first temperature, the second temperature, the first pH, and the second pH; and
  selecting a third calibration equation relating $c_{T,pH}$ to temperature and pH, the equation depending on a third set of the temperature and pH calibration parameters, and setting a value for each parameter based on the values of $c_{T,pH}$ at the first temperature, the second temperature, the first pH, and the second pH.

5. The method of claim 4, wherein:
the first calibration equation is the product of a first pH-independent function and a first temperature-independent function;
the second calibration equation is the product of a second pH-independent function and a second temperature-independent function; and
the third calibration equation is the product of a third pH-independent function and a third temperature-independent function;
wherein the first, second, and third temperature-independent functions are $\tau_{a_T}(T) = m_{a_T} * T + \beta_{a_T}$, $\tau_{b_T}(T) = m_{b_T} * T + \beta_{b_T}$, and $\tau_{c_T}(T) = m_{c_T} * T + \beta_{c_T}$, and wherein the first, second, and third temperature-independent functions are $\rho_{a_{pH}}(pH) = m_{a_{pH}} * pH + \beta a_{pH}$, $\rho_{b_{pH}}(pH) = m_{b_{pH}} * pH + \beta b_{pH}$, and $$\rho_{c_{pH}}(pH) = \frac{e^{\left(\frac{m_{c_{pH}}}{pH} + \beta_{c_{pH}}\right)}}{e^{\left(\frac{m_{c_{pH}}}{7.4} + \beta_{c_{pH}}\right)}}.$$

6. The method of claim 5, wherein:
the first, second, and third pH-independent functions are linear in temperature;

the first, and second temperature-independent functions are linear in pH; and the third temperature-independent function is a fraction wherein the numerator is equal to an exponential function of a function linear in the inverse of pH, and the denominator is equal to an exponential function of the same function linear in the inverse of pH evaluated at fixed pH.

7. The method of claim 6, wherein transforming the signal indicative of the glucose concentration utilizing the equation comprises at least one of $a_{T,pH}$, $b_{T,pH}$, and $c_{T,pH}$ substituted with a calibration equation functionally that depends on a set of one or more temperature calibration parameters, pH calibration parameters, the signal indicative of the temperature, and the signal indicative of the pH.

8. The method of claim 7, wherein the step of transforming the signal indicative of the glucose concentration utilizes the equation wherein:

$a_{T,pH}$ has been substituted with a first calibration equation functionally depending on a first set of temperature and pH calibration parameters, the signal indicative of the temperature, and the signal indicative of the pH;

$b_{T,pH}$ has been substituted with a second calibration equation functionally depending on a second set of temperature and pH calibration parameters, the signal indicative of temperature, and the signal indicative of pH; and $c_{T,pH}$ has been substituted with a third calibration equation functionally depending on a third set of temperature and pH calibration parameters, the signal indicative of temperature, and the signal indicative of pH.

9. The method of claim 1, wherein $a_{T,pH}$ is defined by the equation $a_{T,pH}=a_0 * \tau_{a_T}(T) * \rho_{a_{pH}}(pH)$, wherein $b_{T,pH}$ is defined by the equation $b_{T,pH}=b_0 * \tau_{b_T}(T) * \rho_{b_{pH}}(pH)$, and wherein $c_{T,pH}$ is defined by the equation $c_{T,pH}=b_0 * \tau_{c_T}(T) * \rho_{c_{pH}}(pH)$.

10. The method of claim 1, wherein the temperature and pH calibration data are generated by a calibration method comprising:

providing at least three solutions of differing known glucose concentrations;

providing a first test glucose sensing element;

generating a first set of at least three signals using the first test glucose sensing element, each signal indicative of the concentration of glucose in a different solution of the at least three solutions at a first temperature and pH;

generating a second set of at least three signals using the first test glucose sensing element, each signal indicative of the concentration of analyte in a different solution of the at least three solutions at a second temperature and pH.

11. The method of claim 10, wherein the calibration method further comprises:

determining values of each of $a_{T,pH}$, $b_{T,pH}$, and $c_{T,pH}$ at the first temperature and pH by an algorithm comprising fitting the equation to a first fit dataset comprising the first set of at least three signals;

determining values of each of and $a_{T,pH}$, $b_{T,pH}$, and $c_{T,pH}$ at the second temperature and pH by an algorithm comprising fitting the equation to a second fit dataset comprising the second set of at least three signals;

selecting an equation relating $a_{T,pH}$, $b_{T,pH}$, and $c_{T,pH}$ to temperature and pH, the$_{pH}$, equation depending on a first set, second set, and third set of temperature and pH calibration parameters respectively;

determining a value for each calibration parameter of the first, second, and third set of calibration parameters based on the value of $a_{T,pH}$, $b_{T,pH}$, and $c_{T,pH}$ respectively at the first temperature and pH; and determining a value for each calibration parameter of the first, second, and third set of calibration parameters based on the value of $a_{T,pH}$, $b_{T,pH}$, and $c_{T,pH}$ respectively at the second temperature and pH.

12. The method of claim 11, wherein:

for the step of selecting an equation, equations linear in temperature and pH are selected to relate $a_{T,pH}$, $b_{T,pH}$, and $c_{T,pH}$ to temperature and pH; and wherein each of the first, second, and third sets of temperature and pH calibration parameters comprise a slope and an intercept relating temperature and pH to the value of either $a_{T,pH}$, $b_{T,pH}$, and $c_{T,pH}$.

13. The method of claim 11, wherein the calibration method further comprises:

providing a second test glucose sensing element;

generating a third set of at least three signals using the second test glucose sensing element, each signal indicative of the concentration of glucose in a different solution of the at least three solutions at the first temperature and pH;

generating a fourth set of at least three signals using the test glucose sensing element, each signal indicative of the concentration of glucose in a different solution of the at least three solutions at the second temperature and pH.

14. The method of claim 13, wherein generating values $a_{T,pH}$, $b_{T,pH}$, and $c_{T,pH}$ at the first temperature and pH by an algorithm further comprises:

fitting the equation to a third fit dataset comprising the third set of at least three signals;

averaging the results of fitting the third fit dataset with the results of fitting the first fit dataset; and determining each of $a_{T,pH}$, $b_{T,pH}$, and $c_{T,pH}$ at the second temperature and pH by:

fitting a the equation to a fourth fit dataset comprising the fourth set of at least three signals; and averaging the results of fitting the fourth fit dataset with the results of fitting the second fit dataset.

\* \* \* \* \*

UNITED STATES PATENT AND TRADEMARK OFFICE
CERTIFICATE OF CORRECTION

PATENT NO. : 8,473,222 B2  
APPLICATION NO. : 13/046571  
DATED : June 25, 2013  
INVENTOR(S) : Romey et al.

It is certified that error appears in the above-identified patent and that said Letters Patent is hereby corrected as shown below:

In the Specifications:

In column 20 at line 58, Change "ether." to --ether--.

In column 20 at line 58, Change "sulfone" to --sulfone (—$SO_2$—),--.

In column 22 at line 16, Change "$R^+$," to --$Rb^+$,--.

In the Claims:

In column 75 at line 60, In Claim 4, Change "anpH" to --an--.

In column 78 at line 3, In Claim 11, Change "of and" to --of--.

In column 78 at line 8 (approx.), In Claim 11, Change "the$_{pH}$," to --the--.

In column 78 at line 48 (approx.), In Claim 14, Change "a the" to --the--.

Signed and Sealed this  
Twenty-eighth Day of January, 2014

Michelle K. Lee  
*Deputy Director of the United States Patent and Trademark Office*